(12) United States Patent  (10) Patent No.: US 9,163,027 B2
Punnonen et al.  (45) Date of Patent: Oct. 20, 2015

(54) SUBSTITUTED TRIAZOLO-PYRIMIDINE COMPOUNDS FOR MODULATING CELL PROLIFERATION DIFFERENTIATION AND SURVIVAL

(71) Applicant: STATegics, Inc., Menlo Park, CA (US)

(72) Inventors: Juha Punnonen, Belmont, CA (US); Jeffrey R. Spencer, South San Francisco, CA (US); Timothy J. Church, San Mateo, CA (US); Connie S. Tettenborn, Belmont, CA (US); Karen Lariosa-Willingham, Mountain View, CA (US); Dimitri Leonoudakis, San Rafael, CA (US); James L. Miller, Los Altos, CA (US)

(73) Assignee: STATegics, Inc., South San Francisco, CA (US)

( * ) Notice: Subject to any disclaimer, the term of this patent is extended or adjusted under 35 U.S.C. 154(b) by 0 days.

(21) Appl. No.: 14/085,712

(22) Filed: Nov. 20, 2013

(65) Prior Publication Data

US 2014/0142122 A1 May 22, 2014

Related U.S. Application Data

(60) Provisional application No. 61/729,176, filed on Nov. 21, 2012.

(51) Int. Cl.
 A61K 31/519 (2006.01)
 C07D 487/04 (2006.01)

(52) U.S. Cl.
 CPC .................................. C07D 487/04 (2013.01)

(58) Field of Classification Search
 USPC ...................................... 514/259.31; 544/263
 See application file for complete search history.

(56) References Cited

U.S. PATENT DOCUMENTS

| | | | |
|---|---|---|---|
| 4,036,840 | A | 7/1977 | O'Brien et al. |
| 5,478,825 | A | 12/1995 | Reiter et al. |
| 5,571,813 | A | 11/1996 | Rühter et al. |
| 7,037,902 | B2 | 5/2006 | Olsson et al. |
| 7,799,782 | B2 * | 9/2010 | Munson et al. ............ 514/234.5 |
| 7,816,365 | B2 | 10/2010 | Schiemann et al. |
| 8,765,760 | B2 | 7/2014 | Campbell et al. |
| 2007/0129383 | A1 | 6/2007 | Kuramochi et al. |
| 2010/0196357 | A1 | 8/2010 | Huang et al. |
| 2012/0178748 | A1 | 7/2012 | Campbell et al. |

FOREIGN PATENT DOCUMENTS

| | | |
|---|---|---|
| CN | 101016301 A | 8/2007 |
| DE | 40 081 81 A1 | 9/1991 |
| DE | 43 05 279 A1 | 8/1994 |
| WO | WO 02/064211 A1 | 8/2002 |
| WO | WO 2006/018725 A1 | 2/2006 |

OTHER PUBLICATIONS

Xiong et al. CAS: 158: 389936, 2012.*
Fischer, Gunther, "Recent Progress in 1,2,4-Triazolo[1,5-a]pyrimidine Chemistry," *Advances in Heterocyclic Chemistry*, 95:143-219 (2007).
Goldberg et al., "Erythropoietin Mimetics Derived from Solution Phase Combinatorial Libraries," *J. Am. Chem. Soc.*, 124(4):544-555 (2002).
Krasovsky, et al., "Synthesis of New Fluorine Containing Triazolo- and Tetrazolopyrimidines," *Synthesis*, (7):901-905 (2002).
Qureshi et al., "Mimicry of erythropoietin by a nonpeptide molecule," *PNAS*, 96(21):12156-12161 (1999).
Reiter, et al., "On Triazoles. XXXV[1]. The Reaction of 5-Amino-1,2,4-Triazoles with Di- and Triketones," *J. Het. Chem.*, 32:407-417 (1995).
Zhai, et al., "Synthesis and Cytotoxicity Studies of Novel [1,2,4]Triazolo[1,5-α]pryimidine-7-amines," *Chem. Pharm. Bull.*, 56(7):941-945 (2008).

* cited by examiner

*Primary Examiner* — Rei-Tsang Shiao
(74) *Attorney, Agent, or Firm* — Morgan, Lewis & Bockius LLP

(57) ABSTRACT

Disclosed herein are erythropoietin-mimetic compounds of Formula I, which modulate the survival, function, or differentiation of, for example, kidney cells, neurons, erythroid cells, or other erythropoietin-responsive cells. The present invention also relates to compounds and methods that preferentially modulate cells expressing the tissue-protective erythropoietin receptor. The compounds of the invention are useful in preventing and treating diseases, such as anemia, organ injury, and diseases of the central nervous system, and as an adjunct to cellular treatments, such as stem cell therapies.

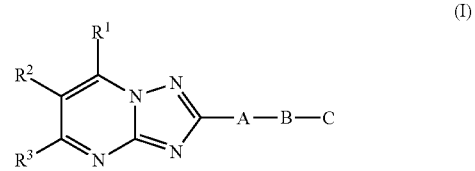

43 Claims, 4 Drawing Sheets

SUBSTITUTED TRIAZOLO-PYRIMIDINE COMPOUNDS FOR MODULATING CELL PROLIFERATION DIFFERENTIATION AND SURVIVAL

This application claims priority to U.S. Provisional Patent Application Ser. No. 61/729,176 filed on Nov. 21, 2012, which is herein incorporated by reference in its entirety for all purposes.

STATEMENT REGARDING FEDERALLY SPONSORED RESEARCH OR DEVELOPMENT

This invention was made with government support under contract number W81XWH-11-2-0009 awarded by the U.S. Army Medical Research and Materiel Command (USAMRMC). The government has certain rights in the invention.

FIELD OF THE INVENTION

The present invention relates to erythropoietin-mimetic compounds and methods in the fields of chemistry, biology and medicine. More specifically, the present invention relates to compounds and methods that are useful in modulating the survival, function and differentiation of kidney cells, neurons, erythroid cells, or other erythropoietin-responsive cells. The present invention also relates to compounds and methods that preferentially modulate cells expressing the tissue-protective erythropoietin receptor.

BACKGROUND

EPO and EPO Receptor (EPOR)

Erythropoietin (EPO) is the primary stimulator of erythroid progenitor cells. The role of recombinant human (rh) EPO in erythropoiesis is well characterized and has been known for more than 50 years (Jacobson et al., Trans. Assoc. Am. Physicians. (1957) 70:305; Muench and Namikawa, Blood Cells Mol. Dis. (2001) 27:377). The three-dimensional structure of EPO and the extracellular domain of the homodimeric EPOR has been determined (Syed et al., Nature (1998) 395:511). EPO binds to the conserved receptor homology (CRH) domain that shares structural features with a family of related cytokine receptors and includes two immunoglobulin-like beta-sheet domains. Upon binding to a predimerized receptor, EPO activates the JAK2-STAT5 signaling pathway resulting in activation of nuclear transcription (Witthuhn et al., Cell (1993) 74:227; Yoshimura and Misawa, Curr Opin Hematol. (1998) 5:171), and Jak2 phosphorylation is also critical for EPO's neuroprotective activities (Digicaylioglu and Lipton, Nature (2001) 412:641).

The GM-CSF/IL-3/IL-5 receptor common beta-chain (CD131) has been shown to functionally and physically associate with the extracellular portion of EPOR (Brines et al., PNAS (2004) 101:14907; Jubinsky et al., Blood (1997) 90:1867, and the tissue- and neuroprotective effects of EPO have been linked to the expression of CD131 (Brines et al., PNAS (2004) 101:14907; Leist et al., Science (2004) 305:239). No protective effects of EPO were observed in mice lacking CD131 (Brines et al., PNAS (2004) 101:14907). However, in vitro studies in rat cell line PC12 indicated that coexpression of CD 131 is not always a prerequisite for the cytoprotective activities of rhEPO (Um et al., Cell Signal. (2007) 19:634). CD131 was also shown to associate with EPOR on endothelial cells, and CD131 was crucial for the anti-apoptotic effects of rhEPO in these cells (Su et al., J. Cell Physiol. (2011) 226: 3330; Bennis et al., J Thromb Haemost (2012) 10:1914). These data suggest that CD131 association with the "classical" EPOR is critical for both neurons and endothelial cells.

In selected indications, such as in organ protection and CNS diseases, EPO Receptor Agonists and EPO mimetic compounds that demonstrate low erythropoietic activity, while exhibiting EPO-like cytoprotective effects, will likely provide optimal efficacy while avoiding hematopoietic adverse events. Variants of rhEPO and EPO mimetic peptides with tissue- and neuroprotective activity in vivo and little or no hematopoietic activity have been described, further indicating that these functionalities are independently regulated. For example, carbamylated and desialylated derivatives of EPO and EPO mimetic peptides with apparent tissue protective activities induced only minor effects on reticulocyte counts in mice and rats (Brines et al., PNAS (2004) 101:14907; Erbayraktar et al. (2003) 100:6741; Leist et al. Science. (2004) 305:239; Swartjes et al., Anesthesiology (2011) 115:1084; Patel et al., Mol. Med. (2012) 18:719; Robertson et al., J. Neurotrauma. (2012) 29:1156). While all these new EPO variants and mimetic peptides have been designed to provide benefits over rhEPO, they will likely have the same limitations as rhEPO when it comes to pharmacokinetic properties, crossing the BBB and risk of immunogenicity. Non-peptidic EPO mimetic compounds have been reported, which bind to EPOR in the cytokine binding domain (Qureshi et al., PNAS (1999) 96:12156, Goldberg et al. J. Am. Chem. Soc., (2002) 124:544). Another screen demonstrated the efficacy of small heterocyclic agonists, which appear to act as EPO mimetics and acted in synergy with EPO in cellular proliferation assays (Olsson and Naranda U.S. Pat. No. 7,037,902).

EPO and EPO Mimetics In Tissue- and Neuroprotection

A significant role of rhEPO and other EPOR Agonists in tissue- and neuroprotection and neurogenesis has emerged, suggesting therapeutic applications for organ protection, wound healing, transplantation and diverse neurological disorders, such as Friedreich's ataxia, stroke, multiple sclerosis, spinal cord injury, traumatic brain injury, schizophrenia, depression, Alzheimer's disease and Parkinson's disease (Brines et al., PNAS (2000) 97:10526; Erbayraktar et al., PNAS (2003) 100:6741; Gene et al., Neurosci. Lett. (2001) 298:139; Konishi et al., Brain Res. (1993) 609:29; Puskovic et al., Mol. Ther. (2006) 14:710; Sakanaka et al., PNAS (1998) 95:4635; Bartels et al., Ther Adv Neurol Disord. (2008) 1:193; Sargin et al, Best Pract Res Clin Anaesthesiol. (2010) 24:573; Juul, J Matern Fetal Neonatal Med. (2012) Suppl 4:97). Because of their broad protective activities, EPO and EPO mimetics are promising agents also for the treatment of diabetes mellitus (Choi et al., Curr Diabetes Rev. (2011) 7:284).

EPOR is abundantly expressed in the CNS, including neurons, astrocytes and choroid plexus epithelial cells (Bernaudin et al., J. Cereb. Blood Flow Metab. (1999) 19:643; Digicaylioglu et al., PNAS (1995) 92:3717; Siren et al., Acta Neuropathol. (2001) 101:271). The presence of EPOR is critical for early embryonic neural development as well as for adult neurogenesis and migration of regenerating neurons during post-stroke recovery (Tsai et al., J. Neurosci. (2006) 26:1269). While the expression of EPOR decreases in normal adult neural tissues (Liu et al., J. Biol. Chem. (1997) 272: 32395), the expression of both EPO and its receptor is upregulated following ischemia, supporting a critical role for the EPO/EPOR system in protection against ischemic brain injury (Bernaudin et al., J. Cereb. Blood Flow Metab. (1999) 19:643). EPO and EPO mimetics are also implicated to have beneficial protective effects in glaucoma, optic nerve injury, age-related macular degeneration, chronic diabetic macular edema, retinopathy, peripheral nerve injury and in peripheral neuropathy associated with for example diabetes or chemotherapy (Bianchi, Eur J. Cancer. (2007) 43:710; Tsai, J. Glaucoma. (2007) 16:567; Takagi, Diabetes Res Clin Pract. (2007) 77 Suppl 1:S62; Schmidt, Exp Neurol. (2008) 209:161; Wang et al., Chin Med J (Engl). (2009) 122:2008; Wang et al., Med. Hypotheses. (2009) 72:448; Li et al., (2010) Ophthalmic Surg Lasers Imaging. 41:18; Yin, et al., AJNR Am J. Neuroradiol. (2010) 31:509). However, pharmacokinetic properties of rhEPO are not well suited for CNS diseases. The concentrations of rhEPO in human cerebrospinal fluid were generally more than 1000-fold lower than in circulation following intravenous administration (Xenocostas et al., Eur. J. Clin. Pharmacol. (2005) 61:189).

EPO and EPO Mimetics in Ischemic Stroke and Brain Injury

Initial indications of EPO's cytoprotective effects in vivo were derived from studies in adult rats that had undergone fimbria-formix transections that indicated enhanced survival of septal cholinergic neurons following rhEPO treatment (Konishi et al., Brain Res. (1993) 609:29). In addition, infusion of EPO into the lateral ventricles of gerbils prevented ischemia-induced learning disability and rescued hippocampal CA1 neurons from ischemia-induced cell death (Sakanaka et al., PNAS (1998) 95:4635). These results were corroborated in hippocampally injured rats, in which rhEPO administration associated with a virtually complete elimination of the otherwise severe behavioral impairment caused by fimbria-formix transection (Maláet al., Neural Plast. (2005) 12:329).

Systemically administered rhEPO induces significant protective effects in preclinical models of focal brain ischemia and brain injury, albeit upon frequent administration of large doses of rhEPO. RhEPO reduced infarct volume by approximately 50-75% in a rat model of MCA occlusion (Brines et al., PNAS (2000) 97:10526). Dose-response studies determined that three doses of 5,000 and one dose of 30,000 U/kg rhEPO are protective in seven-day-old rats undergoing unilateral carotid ligation plus 90 minutes of 8% hypoxia (Kellert et al., Pediatr Res. (2007) 61:451). RhEPO treatment also promotes angiogenesis, improves the growth of microvessels, and restores local cerebral blood flow after embolic stroke or permanent focal cerebral ischemia in rats and mice (Li et al., J. Cereb. Blood Flow Metab. (2007) 27:1043). RhEPO treatment significantly reduced endothelial cell death and increased neuronal cell proliferation following focal ischemic stroke in neonatal rats (Keogh et al., J. Pharmacol. Exp. Ther. (2007) 322:521). Both rhEPO and carbamylated EPO had anti-inflammatory and anti-apoptotic effects and resulted in neurologic improvement when administered six hours following embolic MCA occlusion in rats (Wang et al., Br. J. Pharmacol. (2007) 151:1377. Mice treated with daily intraperitoneal injections of a 13-aa EPO peptide exhibited an improvement in neurologic score on day three following MCA occlusion when compared to mice treated with saline (Yuan et al., WO 2007/052154). The same peptide also appeared protective in a mouse model of contusive spinal cord injury.

The beneficial role of rhEPO and other EPOR Agonists has also been demonstrated in several models of traumatic brain injury. For example, rhEPO protected rats from closed head injury (Yatsiv, Faseb J (2005) 19, 1701), blunt trauma caused by a pneumatic piston (Brines, PNAS (2000) 97:10526, radiosurgery (Erbayraktar, Mol Med (2006) 12:74), controlled cortical impact injury induced by gas pressure (Cheman, J Pharmacol Exp Ther (2007) 322:789), and fluid percussion (FP) injury (Hartley, J Neurosurg (2008) 109:708).

RhEPO was also shown to induce neuroregeneration following traumatic brain injury, which was associated with enhanced expression of brain-derived neurotrophic factor (BDNF) in vivo (Mahmood et al., J. Neurosurg. (2007) 107: 392).

Systemic rhEPO was shown to reduce delayed cerebral ischemia and improve outcome scores following aneurysmal subarachnoid hemorrhage in an 80-patient Phase II randomized, doubled-blinded placebo-controlled trial (Tseng et al., J Neurosurg (2009) 111:171). Moreover, repeated low-dose rhEPO improved neurological outcome and reduced the risk of disability in a study of 153 infants with hypoxic-ischemic encephalopathy when compared to placebo (Zhu, Pediatrics (2009) 124:e218).

EPO and EPO Mimetics in Parkinson's Disease (PD)

Several studies have shown a direct benefit of neuroprotection from exogenous EPO receptor agonists on the motor behavior in rodent models of PD (Gene et al., Neurosci. Lett. (2001) 298:139; Kanaan et al., Brain Res. (2006) 1068:221). Direct neuroprotective effects of EPO have been shown using both primary dopaminergic neurons and dopaminergic cell lines. EPO induces neuroprotective effects through inhibition of apoptosis, which involves activation of the Jak2/STAT5 signaling pathway, upregulation of Bcl-2 and Bcl-xL, activation of Akt/GSK signaling, and downstream reduction of caspase-3 activity (Wu et al., Apoptosis. (2007) 12:1365; Silva et al., Blood (1996) 88:1576). Small molecule EPO mimetics are expected to provide significant benefits over protein- and peptide-based EPO receptor agonists through improved crossing of the BBB, oral dosing and lack of immunogenicity, and such compounds will have significant potential as disease modifying agents in PD.

EPO and EPO Mimetics in Cognitive Function and Alzheimer's Disease (AD)

EPO Receptor Agonists are promising in the treatment of AD. In 4-week old mice with unilateral parietal cortex injury, a model for early aging and neurodegeneration, EPO treatment given for 2 weeks immediately following injury prevented behavioral abnormality, cognitive dysfunction and brain atrophy seen in control mice. The results were independent of hematopoietic effects (Siren et al., Brain (2006) 129: 480). A related study in young mice without parietal injury showed that EPO treatment every other day for three weeks improved hippocampal dependent memory compared to untreated controls (Adamcio et al., BMC Biol. (2008) 6:37).

EPO's indirect neuroprotective effects have also been studied in animal models in vivo in the context of other neurotrophic factors. EPO and CEPO were shown to increase BDNF in rats in the dentate gyrus, part of the hippocampus related to spatial learning in traumatic brain injury (Mahmood et al., J. Neurosurg. (2007) 107:392). In addition, EPO increased BDNF mRNA expression in whole brain 1 hour following intracerebroventricular injection in mice (Viviani et al., J. Neurochem. (2005) 93:412). BDNF and its receptor TrkB are expressed in the entorhinal cortex, which is involved in neurodegeneration and short-term memory loss early in AD. BDNF also prevented lesion-induced death of cortical neurons and reduced cognitive impairment in primates (Nagahara et al., Nat. Med. (2009) 15:331), further suggesting that the effects of EPO on BDNF expression may have important beneficial effects in AD and other neurodegenerative diseases.

EPO and EPO Mimetics in Friedreich's Ataxia (FRDA)

Friedreich's ataxia (FRDA) is an inherited neurodegenerative disease primarily caused by a GAA-trinucleotide repeat expansion in the first intron of the frataxin gene (FXN), resulting in reduced frataxin protein expression (Campuzano et al., Science (1996) 271:1423). Frataxin protein levels in FRDA patients vary between 4% and 29% of healthy individuals, while carriers have a 50% reduction of frataxin expression and are asymptomatic. EPO and EPO mimetics are promising agents for the treatment of FRDA because of their neuro- and tissue-protective effects and because they enhance the levels of frataxin protein. In preclinical and clinical studies, rhEPO and other EPOR Agonists, such as carbamylated EPO, increased frataxin expression in both normal and patient cells in vitro and in vivo. RhEPO was shown to increase frataxin levels in vitro in several cells including P19 neurons, FRDA lymphocytes, primary human cardiac myocytes and fibroblasts (Sturm et al., Eur J Clin Invest. (2005) 35:711). In an open label pilot trial with 8 FRDA patients, rhEPO demonstrated an overall 24% increase in frataxin in lymphocytes with a significant improvement in ataxia rating scores (FARS and SARA) and indicators of oxidative stress that persisted during 6 months of treatment (Boesch et al., Mov Disord. (2008) 23:1940). In addition, in patients with chronic kidney disease, rhEPO infusion for anemia caused an increase in frataxin levels by 2-3-fold in peripheral blood mononuclear cells (Sturm et al., Eur J Clin Invest. (2005) 35:711; U.S. Pat. No. 7,790,675). Erythropoietic activity of rhEPO is not required for neuroprotection or frataxin increase, because EPO derivatives without hematopoietic activity enhance neuroprotection and frataxin levels both in vitro and in vivo (Brines et al., PNAS (2008) 105:10925; Sturm et al., Eur J Clin Invest. (2010) 40:561).

EPO and EPO Mimetics In Depression, Schizophrenia, Drug Abuse and Addiction

EPO mimetics have the potential for improvement of cognitive function, mood and overall quality of life. EPO mimetics also have potential in the treatment of addiction and substance abuse, in part due to EPO's ability to upregulate BDNF and GDNF levels. In addition, EPO has been implicated to have potential in the treatment of attention deficit hyperactivity disorder (McPherson, Int J Dev Neurosci. (2008) 26:103).

Low BDNF levels have been associated with depression, bipolar disorder, chronic heroin use and alcohol dependence (Joe, Alcohol Clin Exp Res. (2007) 31:1833; Angelucci, et al., J. Psychopharmacol. (2007) 21:820; Tseng et al., J Psychiatry Neurosci. (2008) 33:449; Umene-Nakano et al., Hum Psychopharmacol. (2009) 24:409). In addition, polymorphisms in the BDNF gene associates with bipolar disorder, schizophrenia, alcohol dependence and tobacco smoking (Neves-Pereira et al., Am J Hum Genet. (2002) 71:651; Neves-Pereira et al., Mol Psychiatry (2005) 10:208; Matsushita et al., Alcohol Clin Exp Res. (2004) 28:1609; Novak et al., Ann Hum Genet. (2010) 74:291). Given that EPO and EPO-R agonists have been shown to enhance BDNF expression in vitro and in vivo (Mahmood et al. J. Neurosurg. (2007) 107:392; Viviani et al., J. Neurochem. (2005) 93:412), EPO mimetic compounds have potential in the treatment of these disorders. Similarly, GDNF levels were elevated in the brain following EPO-treatment (Dzietko, Neurobiol Dis. (2004) 15:177), and GDNF signaling has been implicated in the treatment of drug and alcohol addiction (Ron, Rev Neurosci. (2005) 16:277). Transplantation of GDNF-expressing cells into the striatum and nucleus accumbens was shown to attenuate acquisition of cocaine self-administration in rats (Green-Sadan et al., Eur J. Neurosci. (2003) 18:2093).

The beneficial effects of EPO on cognitive function and mood, combined with enhanced expression of both BDNF and GDNF support the notion that EPO mimetic compounds have potential in the treatment of several psychological disorders, including conditions with reduced expression of BDNF and GDNF. Three-day treatment with rhEPO improved cognitive and neural processing of happy and fearful faces and improved self-reported mood for all three days following administration in healthy volunteers (Miskowiak, J. Neurosci. (2007) 27:2788; Miskowiak, Biol. Psychiatry (2007) 62:1244). In addition, rhEPO increased hippocampus response during picture retrieval, further suggesting potential in the treatment of psychiatric disorders (Ehrenreich, Mol. Psychiatry. (2004) 9:42; Miskowiak, Biol. Psychiatry (2007) 62:1244). Furthermore, schizophrenic patients treated with rhEPO demonstrated a significant improvement over placebo in schizophrenia-related cognitive performance (RBANS subtests, WCST-64) (Ehrenreich, Mol Psychiatry (2007) 12:206). RhEPO and other EPOR Agonists are also promising in the treatment of depression, which is frequently comorbid with for example alcohol dependence and pathological gambling (Umene-Nakano et al., Hum Psychopharmacol. (2009) 24:409; Rømer Thomsen et al., Behav Pharmacol. (2009) 20:527).

EPO and EPO Mimetics in Spinal Muscular Atrophy and Amyotrophic Lateral Sclerosis Spinal muscular atrophy is a recessively inherited neurodegenerative disease that is characterized by mutations in the survival motor neuron (SMN) gene, reduced levels of functional SMN protein, and resulting motor neuron death (Schrank et al., PNAS (1997) 94:9920). Clinical symptoms include progressive muscular atrophy and premature death. EPO mimetics have demonstrated significant neuroprotection, and therefore, would be expected to reduce neurodegeneration or increase neuroregeneration leading to an effective disease modifying treatment.

Amyotrophic lateral sclerosis (ALS) is an inherited neurodegenerative disease that is characterized by a progressive loss of motor neurons that control voluntary muscle movement. Recombinant EPO reduced symptoms and improved secondary survival signals in a mouse model of the disease and is being tested in patients (Koh et al., Eur J. Neurosci. (2007) 25:1923; Lauria et al., Amyotroph. Lateral Scler. (2009) 10:410). Therefore, EPO mimetics are also expected to reduce neurodegeneration or increase neuroregeneration leading to an effective treatment for ALS.

EPO and EPO Mimetics in Transplantation

The tissue- and neuroprotective effects of rhEPO and other EPOR Agonists are beneficial also when developing means to enhance engraftment and survival in tissue and organ transplants. EPO was shown to improve liver regeneration and survival in rat models of extended liver resection and living donor liver transplantation (Bockhorn et al., Transplantation. (2008) 86:1578). High dose recombinant EPO, nonerythropoietic EPO derivatives in particular, are promising in prevention of kidney damage and loss of renal function after successful kidney transplantation (van Rijt et al., Transpl Int. (2013) August 5 [Epub ahead of print]). The neuroprotective and neuroregenerative effects of EPO and EPO mimetics have the potential to further enhance the functionality of the transplanted tissue, for example in the case of skin transplantation to enhance the recovery of sensation in the transplanted tissue.

EPO and EPO Mimetics in Organ Protection and Tissue Repair

A significant role of rhEPO and other EPOR Agonists in tissue repair has emerged, suggesting therapeutic applications for indications such as wound healing (Galeano et al., Diabetes. (2004) 53:2509, Galeano et al., Crit. Care Med. (2006) 34:1139), cardioprotection following ischemia (Fiordaliso et al., PNAS (2005) 102:2046), kidney protection (Bahlmann et al., Circulation (2004) 110:1006; Tillmann et al., Kidney Int. (2006) 69:60) and liver protection and repair (Shawky et al 2012). In mice, EPO treatment enhances early endochondral ossification and transition from soft callus to hard callus, suggesting a role for EPO in bone repair and fracture healing (Holstein et al., Life Sci (2007) 80:893).

EPO and EPO Mimetics in Stem Cell Therapies

An EPO mimetic can also improve stem cell therapies due to its multiple activities on cellular functions in different tissues. The ability to generate pluripotent human stem cells from adult fibroblasts has significantly enhanced the potential of stem cell-based therapies as a practical approach for clinical indications (Takahashi et al., Cell (2007) 131:861; Yu et al., Science (2007) 318:1917). EPO receptor agonist compounds enhance oxygenation and expansion of stem cells, and, thereby, improve development of therapies for indications where stem cell-based approaches have demonstrated promising results, such as myocardial infarction, soft-tissue injury, heart failure, repair of atherosclerotic vessels and diseases of the central nervous system (Sylvester and Longaker, Arch. Surg. (2004) 139: 93; Urbich and Dimmeler, Circ. Res. (2004) 95: 343; Yoon et al. Biol Cell. (2005) 97: 253; Martino and Pluchino, Nat. Rev. Neurosci. (2006) 7: 395). EPO mimetic compounds with improved solubility and permeability would offer advantages in cell-based therapies, such as the improved distribution in wounded tissue and enhanced engraftment of transplanted cells.

EPO and EPO Mimetics in Production of Red Blood Cells (RBC) Ex Vivo

EPO and EPO mimetics play a significant role in expanding stem cells and RBC ex vivo for the benefit of cell transplantation and transfusion medicine. Neildez-Nguyen et al. described a protocol for the significant expansion of CB-derived CD34+ hematopoietic progenitor cells in a well-defined serum-free medium in the absence of feeder cells and stroma (Neildez-Nguyen et al., Nat. Biotechnol. (2002) 20: 467). Based on the sequential addition of growth factors, including TPO, FL, KL, EPO and IGF-1, this protocol allowed for a 200,000-fold amplification of pure erythroid progenitors. When administered to immunodeficient (NOD-SCID) mice, these progenitors continued to proliferate in vivo and differentiated within four days to the terminal stage of enucleated cells producing adult Hb (Neildez-Nguyen et al., Nat. Biotechnol. (2002) 20: 467). When stromal cell were included in the culture protocols, 100% terminal differentiation into mature RBC was observed and associated with >200,000-fold amplification of CD34+ progenitors (Giarratana et al., Nat. Biotechnol. (2005) 23: 69). Cultured RBC generated using this method demonstrated almost identical maturity, functionality, and half-life when compared to natural RBCs in vitro and in vivo, including in a clinical trial (Giarratana et al., Blood (2011) 118:5071).

One approach to improve the efficiency and reduce the cost of cultured RBC is to utilize small molecule cytokine mimetics. Small molecules have relatively longer shelf-life and do not require cold-chain infrastructure for storage, in contrast to most recombinant proteins.

SUMMARY OF THE INVENTION

In one aspect, the invention provides for a compound described herein. In an exemplary embodiment, the compound has a structure according to the formula described herein. In an exemplary embodiment, the invention is directed to a compound of formula (I) and/or pharmaceutically acceptable salts, solvates, and/or esters thereof:

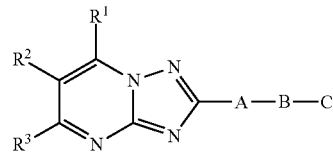

wherein:

A is S, SO, $SO_2$, O, $NR^4$, $C(R^5R^6)_n$, or bond;

B is a member selected from substituted or unsubstituted alkylene, substituted or unsubstituted alkyleneoxy, substituted or unsubstituted alkylenesulfanyl, substituted or unsubstituted alkylenesulfinyl, substituted or unsubstituted alkylenesulfonyl, substituted or unsubstituted alkyleneamino, substituted or unsubstituted cycloalkylene, and substituted or unsubstituted heterocycloalkylene, and substituted or unsubstituted alkylenecarbonylamino;

C is a member selected from substituted or unsubstituted alkyl, substituted or unsubstituted cycloalkyl, substituted or unsubstituted heterocycloalkyl, substituted or unsubstituted aryl, substituted or unsubstituted aralkyl, substituted or unsubstituted heteroaryl, and substituted or unsubstituted heteroaralkyl;

$R^1$ is a member selected from hydrogen, halo, substituted or unsubstituted alkyl, substituted or unsubstituted haloalkyl, substituted or unsubstituted alkoxy, substituted or unsubstituted cycloalkyl, substituted or unsubstituted aryl, and substituted or unsubstituted heterocycloalkyl;

$R^2$ is a member selected from hydrogen, halo, hydroxy, and substituted or unsubstituted alkyl;

$R^3$ is a member selected from hydrogen, halo, substituted or unsubstituted alkyl, substituted or unsubstituted haloalkyl, substituted or unsubstituted alkoxy, substituted or unsubstituted cycloalkyl, substituted or unsubstituted aryl, and substituted or unsubstituted heterocycloalkyl;

Each $R^4$, $R^5$, and $R^6$ is independently selected from hydrogen, substituted or unsubstituted alkyl, substituted or unsubstituted haloalkyl, substituted or unsubstituted hydroxylakyl, substituted or unsubstituted alkoxyalkyl, substituted or unsubstituted aminoalkyl, substituted or unsubstituted alkylaminoalkyl, and substituted or unsubstituted dialkylaminoalkyl; and n is 0 to 3.

In another aspect, the invention is directed to a compound of formula (I) and/or pharmaceutically acceptable salts, solvates, and/or esters thereof, wherein:

A is O, NH, $N(CH_3)$, $N(CH_2CH_3)$, or $N(CH_2CH_2OH)$;

B is a member selected from substituted or unsubstituted $C_2$-$C_8$ alkylene, substituted or unsubstituted $C_2$-$C_8$ alkyleneoxy, substituted or unsubstituted $C_2$-$C_8$ alkylenesulfanyl, substituted or unsubstituted $C_2$-$C_8$ alkylenesulfinyl, substituted or unsubstituted $C_2$-$C_8$ alkylenesulfonyl, substituted or unsubstituted $C_2$-$C_8$ alkyleneamino, substituted or unsubstituted $C_3$-$C_{12}$ cycloalkylene, and substituted or unsubstituted $C_3$-$C_{12}$ heterocycloalkylene;

C is a member selected from substituted or unsubstituted $C_3$-$C_{12}$ cycloalkyl, substituted or unsubstituted $C_3$-$C_{12}$ heterocycloalkyl, substituted or unsubstituted $C_6$-$C_{12}$ aryl, and substituted or unsubstituted $C_5$-$C_{12}$ heteroaryl;

$R^1$ is a member selected from hydrogen, halo, substituted or unsubstituted alkyl, substituted or unsubstituted haloalkyl, substituted or unsubstituted alkoxy, substituted or unsubstituted cycloalkyl, substituted or unsubstituted aryl, and substituted or unsubstituted heterocycloalkyl;

$R^2$ is a member selected from hydrogen, halo, hydroxy, and substituted or unsubstituted alkyl; and $R^3$ is a member selected from hydrogen, halo, substituted or unsubstituted alkyl, substituted or unsubstituted haloalkyl, substituted or unsubstituted alkoxy, substituted or unsubstituted cycloalkyl, substituted or unsubstituted aryl, and substituted or unsubstituted heterocycloalkyl.

In another aspect, the invention is directed to a compound of formula (I) and/or pharmaceutically acceptable salts, solvates, and/or esters thereof, wherein:

A is S;

B is a member selected from substituted or unsubstituted $C_2$-$C_8$ alkylene, substituted or unsubstituted $C_2$-$C_8$ alkyleneoxy, substituted or unsubstituted $C_2$-$C_8$ alkylenesulfanyl, substituted or unsubstituted $C_2$-$C_8$ alkylenesulfinyl, substituted or unsubstituted $C_2$-$C_8$ alkylenesulfonyl, substituted or unsubstituted $C_2$-$C_8$ alkyleneamino, substituted or unsubstituted $C_3$-$C_{12}$ cycloalkylene, and substituted or unsubstituted $C_3$-$C_{12}$ heterocycloalkylene;

C is a member selected from substituted or unsubstituted $C_3$-$C_{12}$ cycloalkyl, substituted or unsubstituted $C_3$-$C_{12}$ heterocycloalkyl, substituted or unsubstituted $C_6$-$C_{12}$ aryl, and substituted or unsubstituted $C_5$-$C_{12}$ heteroaryl;

$R^1$ is a member selected from hydrogen, halo, substituted or unsubstituted alkyl, substituted or unsubstituted haloalkyl, substituted or unsubstituted alkoxy, substituted or unsubstituted cycloalkyl, substituted or unsubstituted aryl, and substituted or unsubstituted heterocycloalkyl;

$R^2$ is a member selected from hydrogen, halo, hydroxy, and substituted or unsubstituted alkyl; and $R^3$ is a member selected from hydrogen, halo, substituted or unsubstituted alkyl, substituted or unsubstituted haloalkyl, substituted or unsubstituted alkoxy, substituted or unsubstituted cycloalkyl, substituted or unsubstituted aryl, and substituted or unsubstituted heterocycloalkyl.

In another aspect, the invention is directed to a compound of formula (I) and/or pharmaceutically acceptable salts, solvates, and/or esters thereof, wherein:

A is bond;

B is a member selected from substituted or unsubstituted $C_3$-$C_8$ alkylene, substituted or unsubstituted $C_3$-$C_8$ alkyleneoxy, substituted or unsubstituted $C_3$-$C_8$ alkylenesulfanyl, substituted or unsubstituted $C_3$-$C_8$ alkylenesulfinyl, substituted or unsubstituted $C_3$-$C_8$ alkylenesulfonyl, substituted or unsubstituted $C_3$-$C_8$ alkyleneamino, substituted or unsubstituted $C_3$-$C_{12}$ cycloalkylene, and substituted or unsubstituted $C_3$-$C_{12}$ heterocycloalkylene;

C is a member selected from substituted or unsubstituted $C_3$-$C_{12}$ cycloalkyl, substituted or unsubstituted $C_3$-$C_{12}$ heterocycloalkyl, substituted or unsubstituted $C_6$-$C_{12}$ aryl, and substituted or unsubstituted $C_5$-$C_{12}$ heteroaryl;

$R^1$ is a member selected from hydrogen, halo, substituted or unsubstituted alkyl, substituted or unsubstituted haloalkyl, substituted or unsubstituted alkoxy, substituted or unsubstituted cycloalkyl, substituted or unsubstituted aryl, and substituted or unsubstituted heterocycloalkyl;

$R^2$ is a member selected from hydrogen, halo, hydroxy, and substituted or unsubstituted alkyl; and $R^3$ is a member selected from hydrogen, halo, substituted or unsubstituted alkyl, substituted or unsubstituted haloalkyl, substituted or unsubstituted alkoxy, substituted or unsubstituted cycloalkyl, substituted or unsubstituted aryl, and substituted or unsubstituted heterocycloalkyl.

In another aspect, the compound is a member described herein. In an exemplary embodiment, the compound has a structure according to a formula described herein. In an exemplary embodiment, the compound is a member selected from 2-{[2-(4-chlorophenoxy)ethyl]sulfanyl}-5,7-dimethyl-[1,2,4]triazolo[1,5-a]pyrimidine; 2-{[2-(4-chlorophenoxy)ethyl]sulfanyl}-5-methyl-[1,2,4]triazolo[1,5-a]pyrimidine; 2-{[2-(4-chloro-3-fluorophenoxy)ethyl]sulfanyl}-5,7-dimethyl-[1,2,4]triazolo[1,5-a]pyrimidine; 2-{[2-({5,7-dimethyl-[1,2,4]triazolo[1,5-a]pyrimidin-2-yl}sulfanyl)ethyl]-(phenyl)amino}ethan-1-ol; 2-[3-(4-chlorophenoxy)propyl]-5,7-diethyl-[1,2,4]triazolo[1,5-a]pyrimidine; 2-[(3-{5,7-diethyl-[1,2,4]triazolo[1,5-a]pyrimidin-2-yl}propyl)(4-fluorophenyl)amino]ethan-1-ol; 2-[2-(4-chlorophenoxy)ethoxy]-5,7-dimethyl-[1,2,4]triazolo[1,5-a]pyrimidine; 2-{[2-({5,7-dimethyl-[1,2,4]triazolo[1,5-a]pyrimidin-2-yl}oxy)ethyl]-(phenyl)amino}ethan-1-ol; 2-{[2-({5,7-diethyl-[1,2,4]triazolo[1,5-a]pyrimidin-2-yl}oxy)ethyl]-(4-fluorophenyl)amino}ethan-1-ol; 2-{[2-({5,7-diethyl-[1,2,4]triazolo[1,5-a]pyrimidin-2-yl}oxy)ethyl]-(phenyl)amino}ethan-1-ol; 5,7-diethyl-N-(2-phenoxyethyl)-[1,2,4]triazolo[1,5-a]pyrimidin-2-amine; 2-[3-(4-chloro-3-fluorophenoxy)propyl]-5,7-bis(propan-2-yl)-[1,2,4]triazolo[1,5-a]pyrimidine; 2-[3-(4-fluorophenoxy)propyl]-5,7-bis(propan-2-yl)-[1,2,4]-triazolo[1,5-a]pyrimidine; 2-[2-(4-chlorophenoxy)ethoxy]-5,7-diethyl-[1,2,4]triazolo[1,5-a]pyrimidine; 2-[2-(4-fluorophenoxy)ethoxy]-5,7-diethyl-[1,2,4]triazolo[1,5-a]pyrimidine; 2-{2-[(4-chlorophenyl)sulfanyl]ethoxy}-5,7-diethyl-[1,2,4]triazolo[1,5-a]pyrimidine; 2-[3-(4-chlorophenoxy)propyl]-5-methyl-7-(trifluoromethyl)-[1,2,4]triazolo[1,5-a]pyrimidine; and 2-({5,7-dimethyl-[1,2,4]triazolo[1,5-a]pyrimidin-2-yl}sulfanyl)-N-(4-methoxyphenyl)acetamide.

In another aspect, this invention is directed to a pharmaceutical composition comprising a pharmaceutically acceptable excipient and a therapeutically effective amount of a compound described herein and/or pharmaceutically acceptable salts, solvates, and/or esters thereof. In an exemplary embodiment, the compound has a structure of Formula (I).

In another aspect, this invention is directed to a method of treating a disease, disorder, or syndrome responsive to an EPO mimetic compound in an animal suffering from said disease, disorder, or syndrome, comprising administering to said animal a compound and/or pharmaceutical composition described herein. In another exemplary embodiment, the compound in the pharmaceutical composition is described herein and/or is a pharmaceutically acceptable salt, solvate, and/or ester thereof. In an exemplary embodiment, the compound has a structure of Formula (I) and/or a pharmaceutically acceptable salt, solvate, and/or ester thereof. In an exemplary embodiment, the animal is a human.

In another aspect, this invention is directed to a method of treating a disorder, symptom, or disease in an animal in need of such treatment, wherein the disorder, symptom, or disease is selected from a group consisting of anemia, Alzheimer's disease, Parkinson's disease, Friedreich's ataxia, spinal muscular atrophy, Amyotrophic lateral sclerosis, Huntington's disease, spinal cord injury, traumatic brain injury, ischemic or hemorrhagic stroke, myocardial infarction, heart failure, peripheral nerve injury or blood vessel injury, soft-tissue injury, kidney injury, liver injury, skin injury, bone fracture, glaucoma, optic nerve injury, age-related macular degeneration, chronic diabetic macular edema, retinopathy, peripheral neuropathy, transplantation, alcohol addiction, substance abuse, bipolar disorder, schizophrenia, depression, and diabetes, which method comprises administering to said animal a compound and/or pharmaceutical composition described herein. In another exemplary embodiment, the compound in the pharmaceutical composition is described herein and/or is a pharmaceutically acceptable salt, solvate, and/or ester thereof. In an exemplary embodiment, the compound has a structure according to a formula described herein. In an exemplary embodiment, the compound has a structure of Formula (I) and/or a pharmaceutically acceptable salt, solvate, and/or ester thereof. In an exemplary embodiment, the animal is a human.

In another aspect, this invention is directed to a method of expanding stem cells by subjecting said stem cells to a compound and/or pharmaceutical composition described herein, in an effective amount in culture or in an animal, to thereby induce the growth of the stem cells in culture or in an animal in need of such stem cells. In an exemplary embodiment, the compound has a structure according to Formula (I). In an exemplary embodiment, the animal is a human.

In another aspect, this invention is directed to novel processes and novel intermediates that are useful in preparing a compound described herein. In an exemplary embodiment, the compound has a structure according to a formula described herein. In an exemplary embodiment, the compound has a structure according to Formula (I).

Other features and advantages of the invention will be apparent from the following detailed description and from the claims.

DETAILED DESCRIPTION OF THE INVENTION

I. Definitions

Figure 1:
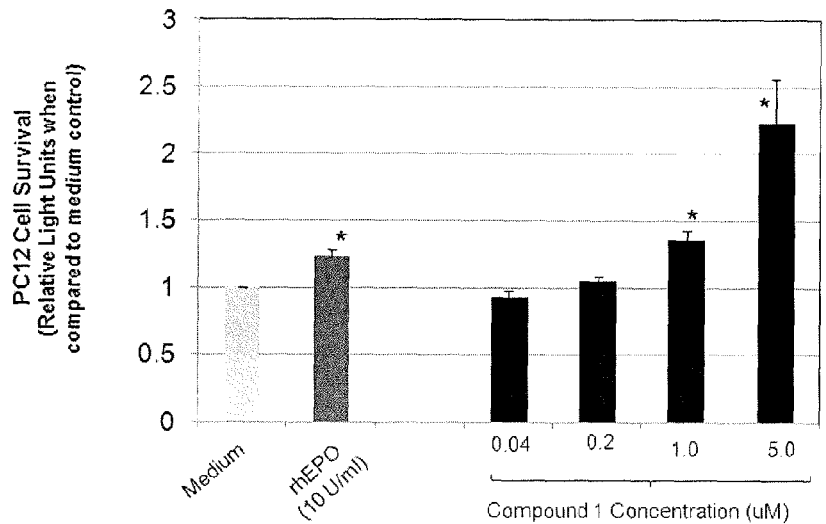
FIG. 1 shows the effects of EPO mimetic, Compound 1, on enhancing the survival of PC12 cells cultured under serum deprivation. PC 12 were cultured for 72 h under serum-free conditions in the presence or absence of Compound 1 or rhEPO. Each culture condition was performed in quadruplicate in each experiment and the mean values were calculated. The results represent mean±SEM of relative light unit values when compared to the mean values obtained in the presence of the medium alone. A total of 13 experiments were performed and the statistical significance was analyzed using GraphPad Prism software using ANOVA, followed by paired t-test. The symbol * indicates P-values <0.01.

Unless otherwise stated, the following terms used in the specification and claims are defined for the purposes of this application and have the following meanings. When any variable occurs more than one time in any moiety, its definition on each occurrence is independent of its definition at every occurrence. A moiety (e.g., "alkyl," "aryl," "heteroaryl," etc.) described as substituted with one or more substituents (e.g., alkyl substituted with one or more hydroxyl groups), includes substitution with one, two, three, etc., substituents, provided that the resulting substituted moiety results in a stable compound (where the term "stable" has the meaning provided herein). Likewise, moieties (e.g., aryl or heteroaryl) which are described as substituted with "0 to 3" substituents include unsubstituted moieties (i.e., "0" substituents), and moieties substituted with one, two, or three such substituents, provided that the resulting substituted moiety results in a stable compound. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "alkoxy," etc.

"Acyl" means a —C(O)R radical where R is alkyl, cyanoalkyl, haloalkyl, alkoxyalkyl, cycloalkyl, cycloalkylalkyl, aryl, aralkyl, heteroaryl, heteroaralkyl, optionally substituted heterocycloalkyl, or optionally substituted heterocycloalkylalkyl, as defined herein, e.g., acetyl, benzoyl, and the like.

"Administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., G-CSF receptor agonists, erythropoietin receptor agonists, hypoxia-inducible factor-1 alpha stabilizing agents, prolyl hydroxylase inhibitors, etc.) "administration" and its variants are each understood to include concurrent and sequential introduction of the compound or prodrug thereof and other agents.

"Alkoxy" means a radical —OR where R is alkyl as defined herein, e.g., methoxy, ethoxy, propoxy, or 2-propoxy, n-, iso-, or tert-butoxy, and the like.

"Alkoxyalkyl" means an alkyl radical, as defined herein, substituted with at least one, preferably one or two, alkoxy group(s), as defined herein, e.g., 2-methoxyethyl, 1-, 2-, or 3-methoxypropyl, 2-ethoxyethyl, or 3,4-dimethoxybutyl, and the like.

"Alkyl" means a linear or branched-chain saturated monovalent hydrocarbon radical of one to six carbon atoms or a branched saturated monovalent hydrocarbon radical of three to six carbon atoms, e.g., methyl, ethyl, propyl, 2-propyl, butyl (including all isomeric forms), or pentyl (including all isomeric forms), and the like. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy, and —C(O)O-alkyl, as defined herein.

"Alkylamino" means the radical —NHR radical where R is alkyl as defined herein, or an N-oxide derivative, or a protected derivative thereof, e.g., methylamino, ethylamino, n-, iso-propylamino, n-, iso-, tert-butylamino, or methylamino-N-oxide, and the like.

"Alkylaminoalkyl" means an alkyl radical, as defined herein, substituted with at least one, preferably one or two, alkylamino group(s), as defined herein.

"Alkylaminocarbonyl" means the radical —C(O)R where R is alkylamino as defined herein, e.g., methylaminocarbonyl or ethylaminocarbonyl, and the like.

"Alkylcarbonyl" means the radical —C(O)R where R is an alkyl radical, as defined herein.

"Alkylcarbonyloxy" means the radical —OC(O)R where R is an alkyl radical, as defined herein.

"Alkylcarbonylamino" means an —NRR' radical, where R is hydrogen or alkyl, as defined herein, and $R^1$ is alkylcarbonyl as defined herein, e.g., methylcarbonylamino or ethylcarbonylamino, and the like.

"Alkylcarbonyloxyalkyl" means an alkyl radical substituted with at least one, preferably one or two, alkylcarbonyloxy group(s), as defined herein.

"Alkylene" means a linear saturated divalent hydrocarbon radical of one to six carbon atoms or as otherwise indicated or a branched saturated divalent hydrocarbon radical of two to six carbon atoms or as otherwise indicated, e.g., methylene, prop-2,2-diyl, eth-1,2-diyl, prop-1,3-diyl, 1-methylprop-1,3-diyl, 2-methylprop-1,3-diyl, but-1,4-diyl (including all isomeric forms), or pent-1,5-diyl (including all isomeric forms), and the like. Alkylene may contain the number of carbon atoms indicated. For example, the term $(alkylene)_{1-3}$ means alkylene containing from 1 carbon atom. i.e., methylene, to 3 carbon atoms, i.e., eth-1,2-diyl, eth-1,1-diyl, prop-1,3-diyl, 1-methyleth-1,2-diyl, 2-methyl-1,2-diyl, prop-1,1-diyl, and prop-2,2-diyl. The term $(alkylene)_0$ means that a bond is intended. The term "alkylene" by itself or as part of another substituent means a divalent radical derived from alkyl, as defined herein, as exemplified by alkyleneamino, alkyleneoxy, alkylenesulfanyl, alkylenesulfinyl, alkylenesulfonyl, cycloalkylene, and heterocycloalkylene. No orientation of the linking group is implied by the direction in which the formula of the linking group is written. Alkylene is unsubstituted or may be substituted by one or more substituents, preferably one, two, or three substituents, which may be the same or different, each substituent being independently selected from the group consisting of halo, alkyl, aryl, cycloalkyl, cyano, hydroxy, hydroxyalkyl, alkoxy, alkoxyalkyl, amino, —NH(alkyl), —NH(cycloalkyl), —N(alkyl)$_2$, carboxy, and —C(O)O-alkyl, as defined herein.

"Alkyleneamino" means an divalent radical derived from alkylamino, as defined herein, as exemplified, but not limited by, —CH$_2$—NH—, —CH$_2$—CH$_2$—NH—, —CH$_2$—CH$_2$—N(CH$_3$)—CH$_2$—, —CH$_2$—CH$_2$—N(CH$_2$CH$_2$OH)—, —CH$_2$—CH$_2$—N(CH$_2$CH$_2$OC(O)CH$_3$)— and the like. Alkyleneamino is unsubstituted or may be substituted by one, two, or three substituents, which may be the same or different, each substituent being independently selected from the group consisting of halo, alkyl, aryl, cycloalkyl, cyano, hydroxy, hydroxyalkyl, alkylcarbonyloxyalkyl, alkoxy, alkoxyalkyl, amino, —NH(alkyl), —NH(cycloalkyl), —N(alkyl)$_2$, carboxy, and —C(O)O-alkyl, as defined herein. Orientations of alkyleneamino are permissible only if such orientations result in a stable compound, as defined herein.

"Alkylenecarbonylamino" means a divalent radical derived from alkylcarbonylamino, as defined herein, as exemplified, but not limited by, —CH$_2$—C(O)NH—, —CH$_2$—CH$_2$—C(O)NH—, —CH(CH$_3$)—CH$_2$—C(O)NH—, —CH$_2$—C$_{12}$—C(O)N(CH$_2$—CH$_2$—OH)—, and the like. Alkylenecarbonylamino is unsubstituted or may be substituted by one, two, or three substituents, which may be the same or different, each substituent being independently selected from the group consisting of halo, alkyl, aryl, cycloalkyl, cyano, hydroxy, hydroxyalkyl, alkylcarbonyloxyalkyl, alkoxy, alkoxyalkyl, amino, —NH(alkyl), —NH(cycloalkyl), —N(alkyl)$_2$, carboxy, and —C(O)O-alkyl, as defined herein. Orientations of alkylenecarbonylamino are permissible only if such orientations result in a stable compound, as defined herein.

"Alkyleneoxy" means a divalent radical derived from alkoxy, as defined herein, as exemplified, but not limited by, —C$_{12}$—O—, —CH$_2$—CH$_2$—O—, —CH$_2$—CH$_2$—CH$_2$—O—, —CH$_2$—CH(CH$_2$)—O—, and the like. Alkyleneoxy is unsubstituted or may be substituted by one, two, or three substituents, which may be the same or different, each substituent being independently selected from the group consisting of halo, alkyl, aryl, cycloalkyl, cyano, hydroxy, hydroxyalkyl, alkylcarbonyloxyalkyl, alkoxy, alkoxyalkyl, amino, —NH(alkyl), —NH(cycloalkyl), —N(alkyl)$_2$, carboxy, and —C(O)O-alkyl, as defined herein. Orientations of alkyleneoxy are permissible only if such orientations result in a stable compound, as defined herein.

"Alkylenesulfanyl" means a divalent radical derived from alkylsulfanyl, as defined herein, as exemplified, but not limited by, —CH$_2$—S—, —CH$_2$—CH$_2$—S—, —CH$_2$—CH$_2$—S—CH$_2$—, and the like. Alkylenesulfanyl is unsubstituted or may be substituted by one, two, or three substituents, which may be the same or different, each substituent being independently selected from the group consisting of halo, alkyl, aryl, cycloalkyl, cyano, hydroxy, hydroxyalkyl, alkylcarbonyloxyalkyl, alkoxy, alkoxyalkyl, amino, —NH(alkyl), —NH(cycloalkyl), —N(alkyl)$_2$, carboxy, and —C(O)O-alkyl, as defined herein. Orientations of alkylenesulfanyl are permissible only if such orientations result in a stable compound, as defined herein.

"Alkylenesulfinyl" means a divalent radical derived from alkylsulfinyl, as defined herein, as exemplified, but not limited by, —CH$_2$—S(O)—, —CH$_2$—CH$_2$—S(O)—, —CH$_2$—CH$_2$—S(O)—CH$_2$—, and the like. Alkylenesulfinyl is unsubstituted or may be substituted by one, two, or three substituents, which may be the same or different, each substituent being independently selected from the group consisting of halo, alkyl, aryl, cycloalkyl, cyano, hydroxy, hydroxyalkyl, alkylcarbonyloxyalkyl, alkoxy, alkoxyalkyl, amino, —NH(alkyl), —NH(cycloalkyl), —N(alkyl)$_2$, carboxy, and —C(O)O-alkyl, as defined herein. Orientations of alkylenesulfinyl are permissible only if such orientations result in a stable compound, as defined herein.

"Alkylenesulfonyl" means a divalent radical derived from alkylsulfonyl, as defined herein, as exemplified, but not limited by, —CH$_2$—SO$_2$—, —CH$_2$—CH$_2$—SO$_2$—, —CH$_2$—CH$_2$—SO$_2$—CH$_2$—, and the like. Alkylenesulfonyl is unsubstituted or may be substituted by one, two, or three substituents, which may be the same or different, each substituent being independently selected from the group consisting of halo, alkyl, aryl, cycloalkyl, cyano, hydroxy, hydroxyalkyl, alkylcarbonyloxyalkyl, alkoxy, alkoxyalkyl, amino, —NH(alkyl), —NH(cycloalkyl), N(alkyl)$_2$, carboxy, and —C(O)O-alkyl, as defined herein. Orientations of alkylenesulfonyl are permissible only if such orientations result in a stable compound, as defined herein.

"Alkylsulfanyl" or "alkylthio" means an —SR radical where R is alkyl as defined herein, e.g., methylsulfanyl, ethylsulfanyl, and the like.

"Alkylsulfinyl" means an —S(O)R radical where R is alkyl as defined herein, e.g., methylsulfinyl, ethylsulfinyl, and the like.

"Alkylsulfonyl" means an —SO$_2$R radical where R is alkyl as defined herein, e.g., methylsulfonyl, ethylsulfonyl, and the like.

"Amino" means an —NH$_2$ radical or an N-oxide derivative, or a protected derivative thereof such as —NH→O, —NHBoc, or —NHCbz, and the like.

"Aminoalkyl" means an alkyl radical, as defined herein, substituted with at least one, preferably one or two, —NH$_2$ group(s), e.g., aminomethyl, aminoethyl, or 1,4-diamino-2-methylpentyl, and the like.

"Aralkyl" means an alkyl radical, as defined herein, substituted with at least one, preferably one or two, aryl group(s) as defined herein, e.g., benzyl, phenethyl, and the like.

"Aryl" means a monovalent, monocyclic or fused bicyclic hydrocarbon radical of 6 to 12 ring atoms, wherein the ring comprising a monocyclic radical ring is aromatic and wherein at least one of the fused rings comprising a bicyclic radical is aromatic. Unless otherwise stated, the valency of the group may be located on any atom of any ring within the radical, valency rules permitting. More specifically the term aryl includes, but is not limited to, phenyl, naphthyl, indanyl (including, for example, indan-5-yl, or indan-2-yl, and the like) or tetrahydronaphthyl (including, for example, tetrahydronaphth-1-yl, tetrahydronaphth-2-yl, and the like), and the like. Unless indicated otherwise, aryl is unsubstituted or may be substituted with one or more "ring system substituents" which may be the same or different, and are as defined herein.

"Carboxy" means a —C(O)OH radical.

"Composition" is intended to encompass a product comprising the specified ingredients in the specified amounts, as well as any product which results, directly or indirectly, from combination of the specified ingredients in the specified amounts.

"Cycloalkyl" means a monocyclic or fused bicyclic, saturated or partially unsaturated, monovalent hydrocarbon radical of three to ten carbon ring atoms. Unless otherwise stated, the valency of the group may be located on any atom of any ring within the radical, valency rules permitting. More specifically, the term cycloalkyl includes, but is not limited to, cyclopropyl, cyclobutyl, cyclopentyl, cyclohexyl, decahydronaphthyl (including, but not limited to decahydronaphth-1-yl, decahydronaphth-2-yl, and the like), norbornyl, adamantly, or cyclohexenyl, and the like. The cycloalkyl ring is unsubstituted or may be substituted with one or more "ring system substituents" which may be the same or different, and are as defined herein.

"Cycloalkylene" means a divalent radical derived from cycloalkyl, as defined herein.

"Cycloalkylalkyl" means an alkyl radical as defined herein, substituted with at least one, preferably one or two, cycloalkyl group(s) as defined herein, e.g., cyclopropylmethyl, cyclobutylmethyl, cyclopentylmethyl, or cyclohexylmethyl, and the like.

"Dialkylamino" means an —NRR' radical where R and R$^1$ are independently alkyl as defined herein, or an N-oxide derivative, or a protected derivative thereof, e.g., dimethylamino, diethylamino, N,N-methylpropylamino, or N,N-methylethylamino, and the like.

"Dialkylaminoalkyl" means an alkyl radical, as defined herein, substituted with at least one, preferably one or two, dialkylamino group(s) as defined herein.

"Erythropoietin mimetic" or "EPO mimetic" or "EPO mimetic compounds" means a compound having a biological activity that, at least partly, mimics that of recombinant human erythropoietin. EPO mimetic compounds may modulate EPO receptor or they may modulate other cellular functions resulting in EPO-like biological effects, or both. EPO receptor modulated by EPO mimetic may be EPO receptor mediating erythropoietin activity or EPO receptor mediating tissue-protective activity, or EPO mimetic may modulate both types of EPO receptors. EPO mimetic compounds are not expected to have structural similarity with EPO.

"Haloalkyl" means an alkyl radical, as defined herein, substituted with at least one, preferably one to five halogen atoms, preferably chlorine or fluorine, including those substituted with different halogens, e.g., —CH$_2$Cl, —CF$_3$, —CHF$_2$, —CF$_2$CF$_3$, —CF(CH$_3$)$_3$, —CHFCl, and the like.

"Substituted haloakyl" means the haloalkyl group is substituted with hydroxy, amino, alkylamino, or cycloalkyl as defined herein.

"Haloalkylamino" means an —NR$^a$R$^b$ radical where R$^a$ is haloalkyl, as defined herein, and R$^b$ is hydrogen, alkyl, or haloalkyl, as defined herein, e.g., N-(trifluoromethyl)-N-(2,2-difluoroethyl)amino.

"Halogen" or "halo" means fluorine, chlorine, bromine, or iodine. Preferred halogens are fluorine, chlorine and bromine.

"Heteroalkyl" means an alkyl, alkenyl or alkynyl radical as defined herein where one or more carbon atoms are replaced by an oxygen, nitrogen, phosphorous or sulphur atom for example an alkoxy group, such as methoxy, ethoxy, propoxy, iso-propoxy, butoxy or tert-butoxy, an alkoxyalkyl group such as methoxymethyl, ethoxymethyl, 1-methoxyethyl, 1-ethoxyethyl, 2-methoxyethyl or 2-ethoxyethyl, an alkylamino group such as methylamino, ethylamino, propylamino, isopropylamino, dimethylamino or diethylamino, an alkylthio group such as methylthio, ethylthio or isopropylthio or a cyano group. It may also refer to one of the above groups containing a keto group. Any heteroalkyl group as defined herein may be substituted with one, two or more substituents, for example F, Cl, Br, I, NH$_2$, OH, SH or NO$_2$.

"Heteroaralkyl" means an alkyl radical, as defined herein, substituted with at least one, preferably one or two, heteroaryl group(s) as defined herein, e.g., pyridinylmethyl, furanylmethyl, or chloropyridinylmethyl, and the like.

"Heteroaryl" means a monocyclic or fused bicyclic, monovalent radical of 5 to 12 ring atoms containing one or more, preferably one, two, three, or four ring heteroatoms independently selected from the group consisting of N, O, P(O)$_m$, Si (where Si is substituted with alkyl and one additional group selected from alkyl, alkenyl, cycloalkylalkyl, aryl, aralkyl, heteroaralkyl, and optionally substituted heterocycloalkylalkyl), and S(O)$_m$, where m is 1 or 2 and n is 0, 1, or 2, the remaining ring atoms being carbon, wherein the ring comprising a monocyclic radical is aromatic and wherein at least one of the fused rings comprising the bicyclic radical is aromatic.

One or two ring carbon atoms can optionally be replaced by a —C(O)—, —C(S)—, or C(=NH)— group. Unless otherwise stated, the valency may be located on any atom of any ring of the heteroaryl group, valency rules permitting. More specifically, the term heteroaryl includes, but is not limited to, phthalimidyl, pyridinyl, pyrrolyl, pyrazolyl, imidazolyl, thienyl, furanyl, indolyl, 2,3-dihydro-1H-indolyl (including, for example, 2,3-dihydro-1H-indol-2-yl or 2,3-dihydro-1H-indol-5-yl, and the like), pyrazinyl, pyrimidinyl, pyridazinyl, oxazolyl, isoxazolyl, benzoxazolyl, quinolinyl, isoquinolinyl, tetrahydroisoquinolinyl (including, for example, tetrahydroisoquinolin-4-yl or tetrahydroisoquinolin-6-yl, and the like), pyrrolo[3,2-c]pyridinyl (including, for example, pyrrolo[3,2-c]pyridin-2-yl or pyrrolo[3,2-c]pyridin-7-yl, and the like), benzopyranyl, thiazolyl, methylenedioxyphenyl (including, for example, methylenedioxyphen-5-yl), and the derivatives thereof, or N-oxide or a protected derivative thereof. The heteroaryl ring is unsubstituted or may be substituted with one, two, or three "ring system substituents" which may be the same or different, and are as defined herein.

"Heterocycloalkyl" means a saturated or partially unsaturated monovalent monocyclic group of 3 to 8 ring atoms or a saturated or partially unsaturated monovalent fused bicyclic group of 5 to 12 ring atoms in which one, two, or three ring atoms are heteroatoms independently selected from the group consisting of N, O, $P(O)_m$, Si (where Si is substituted with alkyl and one additional group selected from the group consisting of alkyl, alkenyl, cycloalkylalkyl, aryl, aralkyl, heteroaralkyl, and optionally substituted heterocycloalkylalkyl), and $S(O)_m$, where m is 1 or 2 and n is 0, 1, or 2, the remaining ring atoms being C. One or two ring carbon atoms can optionally be replaced by a —C(O)—, —C(S)—, or —C(=NH)— group. Unless otherwise stated, the valency of the group may be located on any atom of any ring within the radical, valency rules permitting. More specifically the term heterocycloalkyl includes, but is not limited to, pyrrolidinyl, piperidinyl, morpholinyl, piperazinyl, homopiperazinyl, tetrahydropyranyl, 2-oxopiperidinyl, 5-oxo-4H-[1,2,4]oxadiazol-3-yl, and thiomorpholinyl, and the derivatives thereof and N-oxide or a protected derivative thereof. Unless stated otherwise, the heterocyloalkyl ring is unsubstituted or may be substituted with one, two, or three "ring system substituents" which may be the same or different, and are as defined herein.

"Heterocycloalkylene" means a divalent radical derived from heterocycloalkyl, as defined herein.

"Heterocycloalkylalkyl" means an alkyl radical, as defined herein, substituted with at least one, preferably one or two, optionally substituted heterocycloalkyl group(s) as defined herein, e.g., piperazinylmethyl or morpholinylethyl, and the like.

"Hydroxyalkyl" means an alkyl radical, as defined herein, substituted with at least one, preferably one or two, hydroxy group(s), provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, or 1-(hydroxymethyl)-2-hydroxyethyl, and the like.

"Isomer" or "isomers" means compounds of Formula I having identical molecular formulae but differ in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center has two enantiomeric forms of opposite chirality is termed a "racemic mixture". A compound that has more than one chiral center has $2^{n}$72 enantiomeric pairs, where n is the number of chiral centers. Compounds with more than one chiral center may exist as ether an individual diastereomer or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry," 4th edition, March, Jerry, John Wiley & Sons, New York, 1992). It is understood that the names and illustration used in this application to describe compounds of Formula I are meant to be encompassed all possible stereoisomers and any mixture, racemic or otherwise, thereof.

"Leaving group" means a group that can be displaced by nucleophiles. Examples of leaving groups include but are not limited to halogen, mesyloxy, tosyloxy, alkylsulfonyl, and oxyphosphonium such as triphenylphosphoniumoxy.

"Optional" or "optionally" means that the subsequently described event or circumstance may but need not occur, and that the description includes instances where the event or circumstance occurs and instances in which it does not. For example, "heterocycloalkyl group optionally mono- or disubstituted with an alkyl group" means that the alkyl may but need not be present, and the description includes situations where the heterocycloalkyl group is mono- or disubstituted with an alkyl group and situations where the heterocycloalkyl group is not substituted with the alkyl group.

"Optionally substituted" or "may be substituted," when modifying a particular group, means that the group the term modifies may, but does not have to, be substituted. Where the term "optionally substituted" or "may be substituted" is used to modify a particular group, this does not mean, unless otherwise stated, that any other groups not so modified cannot also be optionally substituted. Furthermore, where a group is defined as being substituted by one of a number of enumerated alternative substituents, it does not mean, unless otherwise stated, that the group cannot be substituted further with one or more substituents not enumerated.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

A "pharmaceutically acceptable salt" of a compound means a salt that is pharmaceutically acceptable and that possesses the desired pharmacological activity of the parent compound. Such salts include: acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethane sulfonic acid, 1,2-ethanedisulfonic acid, 2-hydroxyethanesulfonic acid, benzene sulfonic acid, 4-chlorobenzenesulfonic acid, 2-naphthalenesulfonic acid, 4-toluenesulfonic acid, camphorsulfonic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The compounds of this invention also include other salts of such compounds which are not necessarily pharmaceutically acceptable salts; and which may be useful as intermediates for preparing and/or purifying compounds of this invention and/or for separating isomers of compounds of this invention; and which may be useful as reagents for assays, including biological assays for detection of EPO receptor and/or EPO binding to EPO receptor and/or EPO mimetic binding to EPO receptor, as defined herein.

In addition, when a compound of Formula I herein contains both a basic moiety and an acidic moiety, such as, but not limited to a pyridine or imidazole, and an acidic moiety, such as, but not limited to a carboxylic acid, zwitterions ("inner salts") may be formed and are included within the term "salt(s)" as used herein.

It is understood that the pharmaceutically acceptable salts are non-toxic. Additional information on suitable pharmaceutically acceptable salts can be found in *Remington's Pharmaceutical Sciences,* 17th ed., Mack Publishing Company, Easton, Pa., 1985, which is incorporated herein by reference.

"Ring system substituent" means a substituent attached to an aromatic or non-aromatic ring system, which, for example, replaces an available hydrogen on the ring system. Ring system substituents may be the same or different, each being independently selected from the group consisting of —C(=NH)(NH$_2$), —NHC(=NH)(NH$_2$), alkyl, alkenyl, alkynyl, alkoxy, acyl, alkylcarbonylamino, carboxy, carboxyalkyl, alkoxycarbonyl, alkoxycarbonylalkyl, cyano, nitro, alkylthio, halo, haloalkyl, haloalkoxy, amino, alkylamino, dialkylamino, aminocarbonyl, alkylaminocarbonyl, dialkylaminocarbonyl, alkylsulfonyl, cycloalkylsulfonyl, alkylsulfonylamino, alkylaminosulfonyl, haloalkylamino, oxo, hydroxy, hydroxyalkyl, hydroxyalkyloxy, hydroxyalkyloxyalkyl, alkoxyalkyloxyalkyl, aryl, heteroaryl, cycloalkyl, cycloalkylamino, cycloalkyloxy, heteroaralkyloxy, aminoalkyl, aminoalkyloxy, alkoxyalkyl, alkoxyalkylcarbonyl, alkoxyalkyloxy, haloalkoxyalkyl, aryloxyalkyl, heteroaryloxyalkyl, heterocycloalkyl, heterocycloalkyloxyalkyl, heterocycloalkylalkyl, heterocycloalkylalkyloxy, heterocycloalkyloxy, -alkylene-S(O)$_n$—R$_m$ (where n is 0 to 2 and is alkyl, haloalkyl, hydroxyalkyl, alkoxyalkyl, aryl, heteroaryl, or heteroaralkyl), -alkylene-NHSO$_2$—R$_w$, (where R$_w$ is alkyl, haloalkyl, aryl, heteroaryl, or heteroaralkyl), -alkylene-NHC(O)—R$_q$ (where R$_q$ is alkyl, halo alkyl, aryl, heteroaryl, or heteroaralkyl), and -(methylene)$_{nl}$-C(O)NR$_f$R$_g$ (where nl is 0 or 1, R$_f$ is hydrogen, alkyl, or hydroxyalkyl and R$_g$ is hydrogen, alkyl, hydroxyalkyl, alkoxyalkyl, aryl, heteroaryl, heteroaralkyl, or heterocycloalkylalkyl, or R$_f$ and R$_g$ together with the nitrogen atom to which they are attached from heterocycloalkyl), and -(alkylene)$_{1-3}$-SiR$_{1-3}$ (where R is alkyl). "Ring system substituent" may also mean a single moiety that simultaneously replaces two available hydrogens on two adjacent carbon atoms (one H on each carbon) on a ring system. Examples of such moieties are methylenedioxy, ethylenedioxy, —C(CH$_3$)$_2$— and the like which form moieties such as, for example:

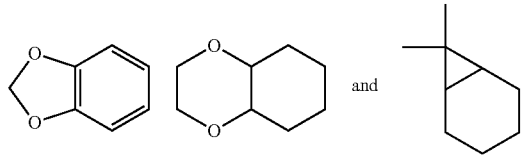

It should be noted that in hetero-atom containing ring systems of this invention, there are no hydroxyl groups on carbon atoms adjacent to a N, O, or S, as well as there are no N or S groups on carbon adjacent to another heteroatom. Thus, for example, in the ring:

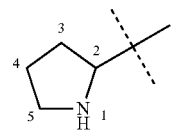

—OH is not attached directly to carbons marked 2 and 5.

It should also be noted that tautomeric forms such as, for example, the moieties:

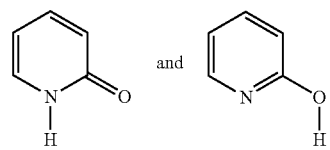 [SMILES: O=c1cccc[nH]1 ; Oc1ccccn1]

are considered equivalent in certain embodiments of this invention. Unless otherwise stated, tautomers may consist of a group of more than two equivalent forms.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. A "stable compound" or "stable structure" means a compound that is sufficiently robust to survive isolation to a useful degree of purity from a reaction mixture, and formulation into an efficacious therapeutic agent. "Substituted," when modifying a particular group, means that the group the term modifies must be substituted. Where the term "substituted" is used to modify a particular group, this does not mean, unless otherwise stated, that any other groups not so modified cannot be substituted. Furthermore, where a group is defined as being substituted by one of a number of enumerated alternative substituents, it does not mean, unless otherwise stated, that the group cannot be substituted further with one or more substituents not enumerated. For example, the phrase "substituted alkyl" means that the alkyl group referred to must be substituted with one or more of the substituents set forth in the definitions for "substituted alkyl."

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any heteroatom with unsatisfied valences in the text, schemes, examples, and Tables herein is assumed to have one or more hydrogen atoms to satisfy the valences.

When a ring system (e.g., cycloalkyl, heterocyclyl, aryl, or heteroaryl) is substituted with a number of substituents varying within an expressly defined range, it is understood that the total number of substituents does not exceed the normal available valencies under the existing conditions. Thus, for example, a phenyl ring substituted with "n" substituents (where "n" ranges from 0 to 5) can have 0 to 5 substituents, whereas it is understood that a pyridinyl ring substituted with "n" substituents has a number of substituents ranging from 0 to 4.

When any variable (e.g., aryl, heterocyclyl, $R^6$, etc.) occurs more than one time in any constituent or in Formula (I), its definition on each occurrence is independent of its definition at every other occurrence.

"Substituted alkyl" means an alkyl radical, as defined herein, substituted with one or more substituent(s), preferably one, two, or three substituents, independently selected from halo, haloalkoxy, haloalkylcarbonyl, haloalkoxycarbonyl, amino, alkylamino, dialkylamino, alkoxy, hydroxy, hydroxyalkyloxy, carboxy, aminocarbonyl, alkylcarbonyl, alkylcarbonylamino, alkylcarbonyloxy, alkylaminocarbonyl, dialkylaminocarbonyl, alkyl-S(O)$_n$—, alkoxycarbonyl, alkylamino-S(O)$_n$—, dialkylamino-S(O)$_n$—, alkylaminocarbonyloxy, dialkylaminocarbonyloxy, alkylaminoalkyloxy, dialkylaminoalkyloxy, alkoxycarbonylamino, alkylaminocarbonylamino, alkoxyalkyloxy, and dialkylaminocarbonylamino, and where n is 0, 1, or 2.

A "therapeutically effective amount" means the amount of a compound of Formula I that, when administered to an animal for treating a disease, is sufficient to effect such treatment for the disease. The "therapeutically effective amount" will vary depending on the compound, the disease and its severity and the age, weight, etc., of the animal to be treated.

"Treating" or "treatment" of a disease, disorder, or syndrome includes:

(1) preventing the disease, disorder, or syndrome, i.e. causing the clinical symptoms of the disease, disorder, or syndrome not to develop in an animal that may be exposed to or predisposed to the disease, disorder, or syndrome but does not yet experience or display symptoms of the disease, disorder, or syndrome;

(2) inhibiting the disease, disorder, or syndrome, i.e., arresting or reducing the development of the disease, disorder, or syndrome or its clinical symptoms; or (3) relieving the disease, disorder, or syndrome, i.e., causing regression of the disease, disorder, or syndrome or its clinical symptoms.

The terms "compound of the invention," and "compounds of the present invention" and "compounds of this invention" and "compounds of Formula I" include compounds of Formula I and isomers, tautomers, metabolites, and pharmaceutically acceptable salts, solvates, esters and prodrugs thereof.

The present invention also includes the prodrugs of compounds of Formula I. The term prodrug is intended to represent covalently bonded carriers, which are capable of releasing the active ingredient of Formula I when the prodrug is administered to an animal subject. Release of the active ingredient occurs in vivo. Prodrugs can be prepared by techniques known to one skilled in the art. These techniques generally modify appropriate functional groups in a given compound. These modified functional groups however regenerate original functional groups by routine manipulation or in vivo. Prodrugs of compounds of Formula I include compounds wherein a hydroxy, amidino, guanidino, amino, carboxylic, or a similar group is modified. Examples of prodrugs include, but are not limited to esters (e.g., acetate, formate, and benzoate derivatives), carbamates (e.g., N,N-dimethylaminocarbonyl of hydroxy or amino functional groups in compounds of Formula I), amides (e.g., trifluoroacetylamino, acetylamino, and the like), and the like. Examples of mechanisms by which the active ingredient is released in vivo include, but are not limited to cleavage of a reactive bond (e.g., amides, esters and carbamate derivatives), oxidation of a partially saturated or unsaturated ring, reduction of a reactive group (e.g., nitroaromatics, disulfide bonds, and oxidized nitrogen atoms) and the like. Release of the active ingredient in vivo includes enzymatic and non-enzymatic processes, including hydrolysis, proteolysis, cytochrome P450 oxidation, or nicotinamide adenine dinucleotide phosphate reduction, and can occur in connection with specific conditions (e.g., hypoxia). Prodrugs of compounds of Formula I are also within the scope of this invention. The present invention also includes N-oxide derivatives and protected derivatives of compounds of Formula I. For example, when compounds of Formula I contain an oxidizable nitrogen atom, the nitrogen atom can be converted to an N-oxide by methods well known in the art. Also when compounds of Formula I contain groups such as hydroxy, carboxy, thiol or any group containing a nitrogen atom(s), these groups can be protected with a suitable protecting group. A comprehensive list of suitable protective groups can be found in Greene, T. W., and Wuts, P. G. M. *Protecting Groups in Organic Synthesis*, John Wiley & Sons, Inc. 1999, the disclosure of which is incorporated herein by reference in its entirety. The protected derivatives of compounds of Formula I can be prepared by methods well known in the art.

The compounds of the present invention may have asymmetric centers. Compounds of the present invention containing an asymmetrically substituted atom may be isolated in optically active or racemic forms. It is well known in the art how to prepare optically active forms, such as by resolution of materials. All chiral, diastereomeric, racemic forms are within the scope of this invention, unless the specific stereochemistry or isomeric form is specifically indicated. Certain compounds of Formula I can exist as isomers. All possible isomers are within the scope of this invention. Additionally, as used herein the terms alkyl includes all the possible isomeric forms of said alkyl group albeit only a few examples are set forth. Furthermore, when the cyclic groups such as aryl, heteroaryl, heterocycloalkyl are substituted, they include all the positional isomers albeit only a few examples are set forth.

Solvates of the compounds of the invention are also contemplated herein. "Solvate" means a physical association of a compound of this invention with one or more solvent molecules. This physical association involves varying degrees of ionic and covalent bonding, including hydrogen bonding. In certain instances, the solvate will be capable of isolation, for example, when one or more solvent molecules are incorporated in the crystal lattice of the crystalline solid. "Solvate" encompasses both solution-phase and isolatable solvates. Non-limiting examples of suitable solvates include ethanolates, methanolates, and the like. A "hydrate" is a solvate wherein the solvent molecule is water.

One or more compounds of the present invention may also exist as, or optionally convert to, a solvate. Preparation of solvates is generally known. Thus, for example, Caira, et al., J. Pharmaceutical Sci., (2004) 93:601, describes the preparation of the solvates of the antifungal fluconazole in ethyl acetate as well as from water. Similar preparations of solvates, hemisolvate, hydrates, and the like are described by van Tonder, et al., AAPS PharmSciTech., 5(1), article 12 (2004); and Bingham, et al., Chem. Commun., (2001) 7:603. A typical, non-limiting process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example infrared spectroscopy, show the presence of the solvent (or water) in the crystals as a solvate (or hydrate).

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of Formula I with a mammal for a period of time sufficient to yield a metabolic product thereof.

II. Embodiments

In one aspect, the invention provides for a compound described herein. In an exemplary embodiment, the compound has a structure according to the formula described herein. In an exemplary embodiment, the invention is directed to a compound of formula (I) and/or pharmaceutically acceptable salts, solvates, and/or esters thereof:

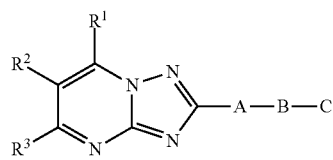

(I)

wherein:

A is S, SO, $SO_2$, O, $NR^4$, $C(R^5R^6)_n$, or bond;

B is a member selected from substituted or unsubstituted alkylene, substituted or unsubstituted alkyleneoxy, substituted or unsubstituted alkylenesulfanyl, substituted or unsubstituted alkylenesulfinyl, substituted or unsubstituted alkylenesulfonyl, substituted or unsubstituted alkyleneamino, substituted or unsubstituted cycloalkylene, and substituted or unsubstituted heterocycloalkylene, and substituted or unsubstituted alkylenecarbonylamino;

C is a member selected from substituted or unsubstituted alkyl, substituted or unsubstituted cycloalkyl, substituted or unsubstituted heterocycloalkyl, substituted or unsubstituted aryl, substituted or unsubstituted aralkyl, substituted or unsubstituted heteroaryl, and substituted or unsubstituted heteroaralkyl;

$R^1$ is a member selected from hydrogen, halo, substituted or unsubstituted alkyl, substituted or unsubstituted alkoxy, substituted or unsubstituted cycloalkyl, substituted or unsubstituted aryl, and substituted or unsubstituted heterocycloalkyl;

$R^2$ is a member selected from hydrogen, halo, hydroxy, and substituted or unsubstituted alkyl;

$R^3$ is a member selected from hydrogen, halo, substituted or unsubstituted alkyl, substituted or unsubstituted alkoxy, substituted or unsubstituted cycloalkyl, substituted or unsubstituted aryl, and substituted or unsubstituted heterocycloalkyl;

Each $R^4$, $R^5$, and $R^6$ is independently selected from hydrogen, substituted or unsubstituted alkyl, substituted or unsubstituted hydroxylakyl, substituted or unsubstituted alkoxyalkyl, substituted or unsubstituted aminoalkyl, substituted or unsubstituted alkylaminoalkyl, and substituted or unsubstituted dialkylaminoalkyl; and n is 0 to 3.

In an exemplary embodiment, the invention is directed to a compound of formula (I) and/or pharmaceutically acceptable salts, solvates, and/or esters thereof, wherein:

A is S, SO, $SO_2$, O, $NR^4$, $C(R^5R^6)_n$, or bond;

B is a member selected from substituted or unsubstituted $C_2$-$C_8$ alkylene, substituted or unsubstituted $C_2$-$C_8$ alkyleneoxy, substituted or unsubstituted $C_2$-$C_8$ alkylenesulfanyl, substituted or unsubstituted $C_2$-$C_8$ alkylenesulfinyl, substituted or unsubstituted $C_2$-$C_8$ alkylenesulfonyl, substituted or unsubstituted $C_2$-$C_8$ alkyleneamino, substituted or unsubstituted $C_3$-$C_{12}$ cycloalkylene, and substituted or unsubstituted $C_3$-$C_{12}$ heterocycloalkylene;

C is a member selected from substituted or unsubstituted $C_3$-$C_{12}$ cycloalkyl, substituted or unsubstituted $C_3$-$C_{12}$ heterocycloalkyl, substituted or unsubstituted $C_6$-$C_{12}$ aryl and substituted or unsubstituted $C_5$-$C_{12}$ heteroaryl; and $R^1$, $R^2$, $R^3$, $R^4$, $R^5$, and $R^6$ are as defined herein; and n is 0 to 3.

In an exemplary embodiment, the invention is directed to a compound of formula (I) and/or pharmaceutically acceptable salts, solvates, and/or esters thereof, wherein:

A is O, NH, $N(CH_3)$, $N(CH_2CH_3)$, or $N(CH_2CH_2OH)$;

B is a member selected from substituted or unsubstituted $C_2$-$C_8$ alkylene, substituted or unsubstituted $C_2$-$C_8$ alkyleneoxy, substituted or unsubstituted $C_2$-$C_8$ alkylenesulfanyl, substituted or unsubstituted $C_2$-$C_8$ alkylenesulfinyl, substituted or unsubstituted $C_2$-$C_8$ alkylenesulfonyl, substituted or unsubstituted $C_2$-$C_8$ alkyleneamino, substituted or unsubstituted $C_3$-$C_{12}$ cycloalkylene, and substituted or unsubstituted $C_3$-$C_{12}$ heterocycloalkylene;

C is a member selected from substituted or unsubstituted $C_3$-$C_{12}$ cycloalkyl, substituted or unsubstituted $C_3$-$C_{12}$ heterocycloalkyl, substituted or unsubstituted $C_6$-$C_{12}$ aryl, and substituted or unsubstituted $C_5$-$C_{12}$ heteroaryl; and $R^1$, $R^2$, and $R^3$ are as defined herein; and n is 0 to 3.

In an exemplary embodiment, the invention is directed to a compound of formula (I) and/or pharmaceutically acceptable salts, solvates, and/or esters thereof, wherein:

A is S;

B is a member selected from substituted or unsubstituted $C_2$-$C_8$ alkylene, substituted or unsubstituted $C_2$-$C_8$ alkyleneoxy, substituted or unsubstituted $C_2$-$C_8$ alkylenesulfanyl, substituted or unsubstituted $C_2$-$C_8$ alkylenesulfinyl, substituted or unsubstituted $C_2$-$C_8$ alkylenesulfonyl, substituted or unsubstituted $C_2$-$C_8$ alkyleneamino, substituted or unsubstituted $C_3$-$C_{12}$ cycloalkylene, and substituted or unsubstituted $C_3$-$C_{12}$ heterocycloalkylene;

C is a member selected from substituted or unsubstituted $C_3$-$C_{12}$ cycloalkyl, substituted or unsubstituted $C_3$-$C_{12}$ heterocycloalkyl, substituted or unsubstituted $C_6$-$C_{12}$ aryl, and substituted or unsubstituted $C_5$-$C_{12}$ heteroaryl; and $R^1$, $R^2$, and $R^3$ are as defined herein; and n is 0 to 3.

In an exemplary embodiment, the invention is directed to a compound of formula (I) and/or pharmaceutically acceptable salts, solvates, and/or esters thereof, wherein:

A is bond;

B is a member selected from substituted or unsubstituted $C_3$-$C_8$ alkylene, substituted or unsubstituted $C_3$-$C_8$ alkyleneoxy, substituted or unsubstituted $C_3$-$C_8$ alkylenesulfanyl, substituted or unsubstituted $C_3$-$C_8$ alkylenesulfinyl, substituted or unsubstituted $C_3$-$C_8$ alkylenesulfonyl, substituted or unsubstituted $C_3$-$C_8$ alkyleneamino, substituted or unsubstituted $C_3$-$C_{12}$ cycloalkylene, and substituted or unsubstituted $C_3$-$C_{12}$ heterocycloalkylene;

C is a member selected from substituted or unsubstituted $C_3$-$C_{12}$ cycloalkyl, substituted or unsubstituted $C_3$-$C_{12}$ heterocycloalkyl, substituted or unsubstituted $C_6$-$C_{12}$ aryl, and substituted or unsubstituted $C_5$-$C_{12}$ heteroaryl; and $R^1$, $R^2$, and $R^3$ are as defined herein; and n is 0 to 3.

In an exemplary embodiment, the invention is directed to a compound of formula (I) and/or pharmaceutically acceptable salts, solvates, and/or esters thereof, wherein:

B is a member selected from substituted or unsubstituted alkylene, substituted or unsubstituted alkyleneoxy, substituted or unsubstituted alkylenesulfanyl, substituted or unsubstituted alkylenesulfinyl, substituted or unsubstituted alkylenesulfonyl, substituted or unsubstituted alkyleneamino; and A, C, $R^1$, $R^2$, $R^3$, $R^4$, $R^5$, and $R^6$ are as defined herein; and n is 0 to 3.

In an exemplary embodiment, the invention is directed to a compound of formula (I) and/or pharmaceutically acceptable salts, solvates, and/or esters thereof, wherein:

B is a member selected from substituted or unsubstituted $C_2$-$C_8$ alkylene, substituted or unsubstituted $C_2$-$C_8$ alkyleneoxy, substituted or unsubstituted $C_2$-$C_8$ alkylenesulfanyl, substituted or unsubstituted $C_2$-$C_8$ alkylenesulfinyl, substituted or unsubstituted $C_2$-$C_8$ alkylenesulfonyl, substituted or unsubstituted $C_2$-$C_8$ alkyleneamino; C is substituted phenyl; and A, $R^1$, $R^2$, $R^3$, $R^4$, $R^5$, and $R^6$ are as defined herein; and n is 0 to 3.

In an exemplary embodiment, the invention is directed to a compound of formula (I) and/or pharmaceutically acceptable salts, solvates, and/or esters thereof, wherein:

B is a member selected from alkylene, alkyleneoxy, alkylenesulfanyl, alkylenesulfinyl, alkylenesulfonyl, alkyleneamino, alkylene(2-hydroxyethyl)amino, and alkylene(2-acetyloxyethyl)amino; and A, C, $R^1$, $R^2$, $R^3$, $R^4$, $R^5$, and $R^6$ are as defined herein; and n is 0 to 3.

In an exemplary embodiment, the invention is directed to a compound of formula (I) and/or pharmaceutically acceptable salts, solvates, and/or esters thereof, wherein:

B is a member selected from unsubstituted alkylene, unsubstituted alkyleneoxy, unsubstituted alkylenesulfanyl, unsubstituted alkylenesulfinyl, unsubstituted alkylenesulfonyl, unsubstituted alkyleneamino, alkylene(2-hydroxyethyl)amino, and alkylene(2-acetyloxyethyl)amino; and A, C, $R^1$, $R^2$, $R^3$, $R^4$, $R^5$, and $R^6$ are as defined herein; and n is 0 to 3.

In an exemplary embodiment, the invention is directed to a compound of formula (I) and/or pharmaceutically acceptable salts, solvates, and/or esters thereof, wherein:

B is a member selected from unsubstituted alkylene, unsubstituted alkyleneoxy, unsubstituted alkylenesulfanyl, unsubstituted alkylenesulfinyl, unsubstituted alkylenesulfonyl, unsubstituted alkyleneamino, alkylene(2-hydroxyethyl)amino, and alkylene(2-acetyloxyethyl)amino; and C is substituted phenyl; and $R^1$ and $R^3$ are unsubstituted alkyl; and A, $R^2$, $R^4$, $R^5$, and $R^6$ are as defined herein; and n is 0 to 3.

In an exemplary embodiment, the invention is directed to a compound of formula (I) and/or pharmaceutically acceptable salts, solvates, and/or esters thereof, wherein:

B is a member selected from ethylenoxy; and

A, C, $R^1$, $R^2$, $R^3$, $R^4$, $R^5$, and $R^6$ are as defined herein; and n is 0 to 3.

In an exemplary embodiment, the invention is directed to a compound of formula (I) and/or pharmaceutically acceptable salts, solvates, and/or esters thereof, wherein:

B is a member selected from ethylenoxy; C is substituted phenyl;

A, C, $R^1$, $R^2$, $R^3$, $R^4$, $R^5$, and $R^6$ are as defined herein; and n is 0 to 3.

In an exemplary embodiment, the invention is directed to a compound of formula (I) and/or pharmaceutically acceptable salts, solvates, and/or esters thereof, wherein:

B is ethylene(2-hydroxyethyl)amino; and

A, C, $R^1$, $R^2$, $R^3$, $R^4$, $R^5$, and $R^6$ are as defined herein; and n is 0 to 3.

In an exemplary embodiment, the invention is directed to a compound of formula (I) and/or pharmaceutically acceptable salts, solvates, and/or esters thereof, wherein:

B is propyleneoxy; and

A, C, $R^1$, $R^2$, $R^3$, $R^4$, $R^5$, and $R^6$ are as defined herein; and n is 0 to 3.

In an exemplary embodiment, the invention is directed to a compound of formula (I) and/or pharmaceutically acceptable salts, solvates, and/or esters thereof, wherein:

B is propyleneoxy; C is substituted phenyl;

A, C, $R^1$, $R^2$, $R^3$, $R^4$, $R^5$, and $R^6$ are as defined herein; and n is 0.

In an exemplary embodiment, the invention is directed to a compound of formula (I) and/or pharmaceutically acceptable salts, solvates, and/or esters thereof, wherein:

B is ethylenesulfanyl; and

A, C, $R^1$, $R^2$, $R^3$, $R^4$, $R^5$, and $R^6$ are as defined herein; and n is 0 to 3.

In an exemplary embodiment, the invention is directed to a compound of formula (I) and/or pharmaceutically acceptable salts, solvates, and/or esters thereof, wherein:

C is substituted phenyl; and

A, B, $R^1$, $R^2$, $R^3$, $R^4$, $R^5$, and $R^6$ are as defined herein; and n is 0 to 3.

In an exemplary embodiment, the invention is directed to a compound of formula (I) and/or pharmaceutically acceptable salts, solvates, and/or esters thereof, wherein:

C is phenyl substituted with halogen; and

A, B, $R^1$, $R^2$, $R^3$, $R^4$, $R^5$, and $R^6$ are as defined herein; and n is 0 to 3.

In an exemplary embodiment, the invention is directed to a compound of formula (I) and/or pharmaceutically acceptable salts, solvates, and/or esters thereof, wherein:

C is cycloalkyl; and

A, B, $R^1$, $R^2$, $R^3$, $R^4$, $R^5$, and $R^6$ are as defined herein; and n is 0 to 3.

In an exemplary embodiment, the invention is directed to a compound of formula (I) and/or pharmaceutically acceptable salts, solvates, and/or esters thereof, wherein:

$R^1$ and $R^3$ are each independently from unsubstituted alkyl or haloalkyl; and A, B, C, $R^2$, $R^4$, $R^5$, and $R^6$ are as defined herein; and n is 0 to 3.

In an exemplary embodiment, the invention is directed to a compound of formula (I) and/or pharmaceutically acceptable salts, solvates, and/or esters thereof, wherein:

$R^1$ is unsubstituted alkyl; $R^3$ is unsubstituted alkyl; and

A, B, C, $R^2$, $R^4$, $R^5$, and $R^6$ are as defined herein; and n is 0 to 3.

In an exemplary embodiment, the invention is directed to a compound of formula (I) and/or pharmaceutically acceptable salts, solvates, and/or esters thereof, wherein:

$R^1$ and $R^3$ is each independently selected from unsubstituted alkyl or haloalkyl;

A, B, C, $R^2$, $R^4$, $R^5$, and $R^6$ are as defined herein; and n is 0 to 3.

In an exemplary embodiment, the invention is directed to a compound of formula (I) and/or pharmaceutically acceptable salts, solvates, and/or esters thereof, wherein:
$R^1$ is haloalkyl; $R^3$ is haloalkyl; and
A, B, C, $R^2$, $R^4$, $R^5$, and $R^6$ are as defined herein; and n is 0 to 3.

In an exemplary embodiment, the invention is directed to a compound of formula (I) and/or pharmaceutically acceptable salts, solvates, and/or esters thereof, wherein:
$R^1$ is methyl, trifluoromethyl, ethyl or isopropyl; $R^3$ is methyl, trifluoromethyl, ethyl or isopropyl; and
A, B, C, $R^2$, $R^4$, $R^5$, and $R^6$ are as defined herein; and n is 0 to 3.

In an exemplary embodiment, the invention is directed to a compound of formula (I) and/or pharmaceutically acceptable salts, solvates, and/or esters thereof, wherein:
$R^2$ is hydrogen; and
A, B, C, $R^1$, $R^3$, $R^4$, $R^5$, and $R^6$ are as defined herein; and n is 0 to 3.

In an exemplary embodiment, the invention is directed to a compound of formula (I) and/or pharmaceutically acceptable salts, solvates, and/or esters thereof, wherein:
A is S, SO, $SO_2$, O, $NR^4$, or $CH_2$; B is alkyleneoxy; and C, $R^1$, $R^2$, $R^3$, and $R^4$ are as defined herein; and n is 0 to 3.

In an exemplary embodiment, the invention is directed to a compound of formula (I) and/or pharmaceutically acceptable salts, solvates, and/or esters thereof, wherein:
A is S, SO, $SO_2$, O, $NR^4$, or $CH_2$; B is alkyleneamino; and C, $R^1$, $R^2$, $R^3$, and $R^4$ are as defined herein; and n is 0 to 3.

In an exemplary embodiment, the invention is directed to a compound of formula (I) and/or pharmaceutically acceptable salts, solvates, and/or esters thereof, wherein:
A is S, SO, $SO_2$, O, $NR^4$, or $CH_2$; B is alkyleneoxy; $R^1$ is unsubstituted alkyl; $R^3$ is unsubstituted alkyl; and C, $R^2$, and $R^4$ are as defined herein; and n is 0 to 3.

In an exemplary embodiment, the invention is directed to a compound of formula (I) and/or pharmaceutically acceptable salts, solvates, and/or esters thereof, wherein:
A is S, SO, $SO_2$, O, $NR^4$, or $CH_2$; B is alkyleneamino; $R^1$ is unsubstituted alkyl; $R^3$ is unsubstituted alkyl; and C, $R^2$, and $R^4$ are as defined herein; and n is 0 to 3.

In an exemplary embodiment, the invention is directed to a compound of formula (I) and/or pharmaceutically acceptable salts, solvates, and/or esters thereof, wherein:
A is S, SO, $SO_2$, O, $NR^4$, or $CH_2$; B is alkyleneoxy; C is substituted phenyl; and
$R^1$, $R^2$, $R^3$, and $R^4$ areas defined herein; and n is 0 to 3.

In an exemplary embodiment, the invention is directed to a compound of formula (I) and/or pharmaceutically acceptable salts, solvates, and/or esters thereof, wherein:
A is S, SO, $SO_2$, O, $NR^4$, or $CH_2$; B is alkyleneamino; C is substituted phenyl; and $R^1$, $R^2$, $R^3$, and $R^4$ are as defined herein; and n is 0 to 3.

In an exemplary embodiment, the invention is directed to a compound of formula (I) and/or pharmaceutically acceptable salts, solvates, and/or esters thereof, wherein:
A is S, SO, $SO_2$, O, $NR^4$, or $CH_2$; C is substituted phenyl; and
B, $R^1$, $R^2$, $R^3$, and $R^4$ are as defined herein; and n is 0 to 3.

In an exemplary embodiment, the invention is directed to a compound of formula (I) and/or pharmaceutically acceptable salts, solvates, and/or esters thereof, wherein:
B is alkyleneoxy or alkyleneamino; C is substituted phenyl; and
A, $R^1$, $R^2$, $R^3$, $R^4$, $R^5$, and $R^6$ are as defined herein; and n is 0 or 1.

In an exemplary embodiment, the invention is directed to a compound of formula (I) and/or pharmaceutically acceptable salts, solvates, and/or esters thereof, wherein:
B is alkyleneoxy or alkyleneamino; C is substituted phenyl; $R^1$ is unsubstituted alkyl; $R^3$ is unsubstituted alkyl; and A, $R^2$, $R^4$, $R^5$, and $R^6$ are as defined herein; and n is 0.

In another embodiment, the invention is directed to a compound of formula (I) and/or pharmaceutically acceptable salts, solvates, and/or esters thereof, wherein:
B is a member selected from alkylene, alkyleneoxy, alkylenesulfanyl, alkylenesulfinyl, alkylenesulfonyl, alkyleneamino, alkylene(2-hydroxyethyl)amino, alkylene(2-acetyloxyethyl)amino, and alkylenecarbonylamino, as defined herein, and is oriented with the alkylene portion of the radical bonded to A; and
A, C, $R^1$, $R^3$, $R^4$, $R^5$, and $R^6$ are as defined herein; and n is 0 to 3.

In an exemplary embodiment, the invention is directed to a compound of formula (I), wherein A is S; B is alkyleneoxy; and C, $R^1$, $R^2$, and $R^3$ are as defined herein.

In an exemplary embodiment, the invention is directed to a compound of formula (I), wherein A is S; B is —$(CH_2)_2$—O—; C is phenyl substituted with one or more methyl, ethyl, isopropyl, tert-butyl, methoxy, —$(CH_2)_2$—OH, —$(CH_2)_2$—N$(CH_3)_2$, —F, —Cl, —Br, or —I; $R^1$ and $R^3$ are each methyl, trifluoromethyl, or hydrogen; and $R^2$ is hydrogen.

In an exemplary embodiment, the invention is directed to a compound of formula (I), wherein A is S; B is —$(CH_2)_2$—O—; C is phenyl mono-substituted with chloro or fluoro; $R^1$ and $R^3$ are each methyl; and $R^2$ is hydrogen.

In an exemplary embodiment, the invention is directed to a compound of formula (I), wherein A is O; B is alkyleneoxy, alkylenesulfanyl, or alkyleneamino; and C, $R^1$, $R^2$, and $R^3$ are as defined herein.

In an exemplary embodiment, the invention is directed to a compound of formula (I), wherein A is O; B is —$(CH_2)_2$—O—, —$(CH_2)_2$—S—, or —$(CH_2)_2$—N($CH_2CH_2OH$)—; C is unsubstituted phenyl, or phenyl substituted with alkyl, alkoxy, or halo; $R^1$ and $R^3$ are each methyl, ethyl, or isopropyl; and $R^2$ is hydrogen.

In an exemplary embodiment, the invention is directed to a compound of formula (I), wherein A is O; B is —$(CH_2)_2$—O—; C is phenyl substituted with chloro or fluoro; $R^1$ and $R^3$ are each methyl; and $R^2$ is hydrogen.

In an exemplary embodiment, the invention is directed to a compound of formula (I), wherein A is O; B is —$(CH_2)_2$—N($CH_2CH_2OH$)—; C is unsubstituted phenyl or phenyl mono-substituted with fluoro or chloro, $R^1$ and $R^3$ are each methyl; and $R^2$ is hydrogen.

In an exemplary embodiment, the invention is directed to a compound of formula (I), wherein A is O; B is —$(CH_2)_2$—O—, —$(CH_2)_2$—S—, or —$(CH_2)_2$—N($CH_2CH_2OH$)—; C is unsubstituted phenyl, $R^1$ and $R^3$ are each methyl; and $R^2$ is hydrogen.

In an exemplary embodiment, the invention is directed to a compound of formula (I), wherein A is NH or N($CH_3$); B is —$(CH_2)_2$—O—; C is unsubstituted phenyl, or phenyl substituted with alkyl, alkoxy, or halo; $R^1$ and $R^3$ are each methyl, ethyl, or isopropyl; and $R^2$ is hydrogen.

In an exemplary embodiment, the invention is directed to a compound of formula (I), wherein A is NH; B is —$(CH_2)_2$—O—; C is unsubstituted phenyl, or phenyl mono-substituted with chloro or fluoro; $R^1$ and $R^3$ are each ethyl; and $R^2$ is hydrogen.

In an exemplary embodiment, the invention is directed to a compound of formula (I), wherein A is bond; B is alkyleneoxy or alkyleneamino; and C, $R^1$, $R^2$, and $R^3$ are as defined herein.

In an exemplary embodiment, the invention is directed to a compound of formula (I), wherein A is bond; B is —$(CH_2)_3$O—, —$(CH_2)_4$—O—, —$(CH_2)_3$—N($CH_2CH_2OH$)—, or —$(CH_2)_3$—N($CH_2CH_2OC(O)CH_3$)—; C is unsubstituted phenyl, or phenyl substituted with alkyl, alkoxy, or halo; $R^1$ and $R^3$ are each methyl, ethyl, isopropyl, or —$CF_3$; and $R^2$ is hydrogen.

In an exemplary embodiment, the invention is directed to a compound of formula (I), wherein A is bond; B is —$(CH_2)_3$—O—; C is phenyl mono-substituted with chloro or fluoro; $R^1$ and $R^3$ are each methyl, ethyl, isopropyl, or —$CF_3$; and $R^2$ is hydrogen.

In an exemplary embodiment, the invention is directed to a compound of formula (I), wherein A is bond; B is —$(CH_2)_3$—N($CH_2CH_2OH$)—; C is phenyl mono-substituted with chloro or fluoro; $R^1$ and $R^3$ are each methyl, ethyl, isopropyl, or —$CF_3$; and $R^2$ is hydrogen.

In an exemplary embodiment, the invention is directed to a compound of formula (I), wherein $R^1$ and $R^3$ are each methyl; $R^2$ is hydrogen; and A, B, and C are as defined herein.

In an exemplary embodiment, the compound is a member described herein. In an exemplary embodiment, the compound has a structure according to a formula described herein. In an exemplary embodiment, the compound is a member selected from 2-{[2-(4-chlorophenoxy)ethyl]sulfanyl}-5,7-dimethyl-[1,2,4]triazolo[1,5-a]pyrimidine; 2-{[2-(4-chlorophenoxy)ethyl]sulfanyl}-5-methyl-[1,2,4]triazolo[1,5-a]pyrimidine; 2-{[2-(4-chloro-3-fluorophenoxy)ethyl]sulfanyl}-5,7-dimethyl-[1,2,4]triazolo[1,5-a]pyrimidine; 2-{[2-({5,7-dimethyl-[1,2,4]triazolo[1,5-a]pyrimidin-2-yl}sulfanyl)ethyl]-(phenyl)amino}ethan-1-ol; 2-[3-(4-chlorophenoxy)propyl]-5,7-diethyl-[1,2,4]triazolo[1,5-a]pyrimidine; 2-[(3-{5,7-diethyl-[1,2,4]-triazolo[1,5-a]pyrimidin-2-yl}propyl)(4-fluorophenyl)amino]ethan-1-ol; 2-[2-(4-chlorophenoxy)ethoxy]-5,7-dimethyl-[1,2,4]triazolo[1,5-a]pyrimidine; 2-{[2-({5,7-dimethyl-[1,2,4]triazolo[1,5-a]pyrimidin-2-yl}oxy)ethyl](phenyl)amino}ethan-1-ol; 2-{[2-({5,7-diethyl-[1,2,4]-triazolo[1,5-a]pyrimidin-2-yl}oxy)ethyl]-(4-fluorophenyl)amino}ethan-1-ol; 2-{[2-({5,7-diethyl-[1,2,4]triazolo[1,5-a]pyrimidin-2-yl}oxy)ethyl](phenyl)amino}ethan-1-ol; 5,7-diethyl-N-(2-phenoxyethyl)-[1,2,4]triazolo[1,5-a]pyrimidin-2-amine; 2-[3-(4-chloro-3-fluorophenoxy)propyl]-5,7-bis(propan-2-yl)-[1,2,4]-triazolo[1,5-a]pyrimidine; 2-[3-(4-fluorophenoxy)propyl]-5,7-bis(propan-2-yl)-[1,2,4]-triazolo[1,5-a]pyrimidine; 2-[2-(4-chlorophenoxy)ethoxy]-5,7-diethyl-[1,2,4]triazolo[1,5-a]pyrimidine; 2-[2-(4-fluorophenoxy)ethoxy]-5,7-diethyl-[1,2,4]triazolo[1,5-a]pyrimidine; 2-{2-[(4-chlorophenyl)sulfanyl]ethoxy}-5,7-diethyl-[1,2,4]triazolo[1,5-a]pyrimidine; 2-[3-(4-chlorophenoxy)propyl]-5-methyl-7-(trifluoromethyl)-[1,2,4]triazolo[1,5-a]pyrimidine; and 2-({5,7-dimethyl-[1,2,4]triazolo[1,5-a]pyrimidin-2-yl}sulfanyl)-N-(4-methoxyphenyl)acetamide.

In another embodiment, the compound is a member selected from 2-{[2-({5,7-dimethyl-[1,2,4]triazolo[1,5-a]pyrimidin-2-yl}sulfanyl)ethyl]-(phenyl)amino}ethan-1-ol; 2-[(3-{5,7-diethyl-[1,2,4]triazolo[1,5-a]pyrimidin-2-yl}propyl)(4-fluorophenyl)amino]ethan-1-ol; 2-[2-(4-chlorophenoxy)ethoxy]-5,7-dimethyl-[1,2,4]-triazolo[1,5-a]pyrimidine; 2-{[2-({5,7-dimethyl-[1,2,4]triazolo[1,5-a]pyrimidin-2-yl}oxy)ethyl]-(phenyl)amino}ethan-1-ol; 2-{[2-({5,7-diethyl-[1,2,4]triazolo[1,5-a]pyrimidin-2-yl}oxy)ethyl]-(4-fluorophenyl)amino}ethan-1-ol; 5,7-diethyl-N-(2-phenoxyethyl)-[1,2,4]triazolo[1,5-a]pyrimidin-2-amine.

In another embodiment, the compound is a member selected from 2-[2-(4-chlorophenoxy)ethoxy]-5,7-dimethyl-[1,2,4]triazolo[1,5-a]pyrimidine; 2-{[2-({5,7-dimethyl-[1,2,4]triazolo[1,5-a]pyrimidin-2-yl}oxy)ethyl]-(phenyl)amino}ethan-1-ol; 5,7-diethyl-N-(2-phenoxyethyl)-[1,2,4]triazolo[1,5-a]pyrimidin-2-amine.

In still an additional embodiment, the present invention is directed to a pharmaceutical composition comprising a pharmaceutically acceptable excipient and a therapeutically effective amount of a compound described herein and/or pharmaceutically acceptable salts, solvates, and/or esters thereof. In an exemplary embodiment, the compound has a structure of Formula I.

In an exemplary embodiment, the invention provides a compound described herein, or a salt, hydrate or solvate thereof, or a combination thereof. In an exemplary embodiment, the invention provides a compound described herein, or a salt, hydrate or solvate thereof. In an exemplary embodiment, the invention provides a compound described herein, or a salt thereof. In an exemplary embodiment, the salt is a pharmaceutically acceptable salt. In an exemplary embodiment, the invention provides a compound described herein, or a hydrate thereof. In an exemplary embodiment, the invention provides a compound described herein, or a solvate thereof. In an exemplary embodiment, the invention provides a compound described herein, or a prodrug thereof. In an exemplary embodiment, the invention provides a salt of a compound described herein. In an exemplary embodiment, the invention provides a pharmaceutically acceptable salt of a compound described herein. In an exemplary embodiment, the invention provides a hydrate of a compound described herein. In an exemplary embodiment, the invention provides a solvate of a compound described herein. In an exemplary embodiment, the invention provides a prodrug of a compound described herein. In an exemplary embodiment, the invention provides a compound of Formula I, or a salt thereof. In an exemplary embodiment, the invention provides a compound of Formula I, or a pharmaceutically acceptable salt thereof.

In still an additional embodiment, the present invention is directed to a method of treating a disease, disorder, or syndrome responsive to an EPO mimetic compound in an animal suffering from said disease, disorder, or syndrome, comprising administering to said animal a compound and/or pharmaceutical composition described herein. In another exemplary embodiment, the compound in the pharmaceutical composition is described herein and/or is a pharmaceutically acceptable salt, solvate, and/or ester thereof. In an exemplary embodiment, the compound has a structure of Formula (I) and/or a pharmaceutically acceptable salt, solvate, and/or ester thereof. In an exemplary embodiment, the animal is a human.

In another aspect, this invention is directed to novel processes and novel intermediates that are useful in preparing a compound described herein. In an exemplary embodiment, the compound has a structure according to a formula described herein. In an exemplary embodiment, the compound has a structure according to Formula (I).

Preferred are compounds of formula (I)

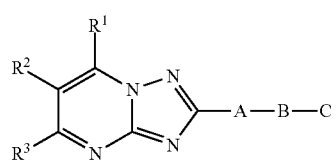

(I)

and/or pharmaceutically acceptable salts, solvates, and/or esters thereof,
wherein:
A is S, SO, $SO_2$, O, $NR^4$, $C(R^5R^6)_n$, or bond;
B is a member selected from alkylene, alkyleneoxy, alkylenesulfanyl, alkylenesulfinyl, alkylenesulfonyl, alkyleneamino, alkylene(2-hydroxyethyl)amino, alkylene(2-acetyloxyethyl)amino, cycloalkylene, heterocycloalkylene, and alkylenecarbonylamino;

C is a member selected from substituted or unsubstituted alkyl, substituted or unsubstituted cycloalkyl, substituted or unsubstituted heterocycloalkyl, substituted or unsubstituted aryl, substituted or unsubstituted aralkyl, substituted or unsubstituted heteroaryl, and substituted or unsubstituted heteroaralkyl;

$R^1$ is a member selected from hydrogen, halo, substituted or unsubstituted alkyl, substituted or unsubstituted alkoxy, substituted or unsubstituted cycloalkyl, substituted or unsubstituted aryl, and substituted or unsubstituted heterocycloalkyl;

$R^2$ is a member selected from hydrogen, halo, hydroxy, and substituted or unsubstituted alkyl;

$R^3$ is a member selected from hydrogen, halo, substituted or unsubstituted alkyl, substituted or unsubstituted alkoxy, substituted or unsubstituted cycloalkyl, substituted or unsubstituted aryl, and substituted or unsubstituted heterocycloalkyl;

Each $R^4$, $R^5$, and $R^6$ is independently selected from hydrogen, substituted or unsubstituted alkyl, substituted or unsubstituted hydroxylakyl, substituted or unsubstituted alkoxyalkyl, substituted or unsubstituted aminoalkyl, substituted or unsubstituted alkylaminoalkyl, and substituted or unsubstituted dialkylaminoalkyl; and n is 0 to 3.

Preferred are compounds of Formula I in which:

A is S, SO, SO$_2$, O, NR$^4$, or CH$_2$;

B is a member selected from alkylene, alkyleneoxy, alkylenesulfanyl, alkylenesulfinyl, alkylenesulfonyl, alkyleneamino, alkylene(2-hydroxyethyl)amino, and alkylene(2-acetyloxyethyl)amino;

C is a member selected from substituted or unsubstituted alkyl, substituted or unsubstituted cycloalkyl, substituted or unsubstituted heterocycloalkyl, substituted or unsubstituted aryl, and substituted or unsubstituted heteroaryl;

$R^1$ is a member selected from hydrogen, halo, substituted or unsubstituted alkyl, and substituted or unsubstituted alkoxy;

$R^2$ is a member selected from hydrogen, halo, hydroxy, and substituted or unsubstituted alkyl;

$R^3$ is a member selected from hydrogen, halo, substituted or unsubstituted alkyl, and substituted or unsubstituted alkoxy; and $R^4$ is hydrogen or alkyl.

Preferred are compounds of Formula I in which $R^1$ is methyl, trifluoromethyl, ethyl or isopropyl, $R^2$ is hydrogen, $R^3$ is methyl, trifluoromethyl, ethyl or isopropyl, A is S, O, NH, or CH$_2$, B is ethyleneoxy or ethylene(2-hydroxyethyl) amino, and C is phenyl optionally substituted with 1-3 groups selected from halo, methoxy, and isopropyl.

Preferred is a pharmaceutical composition comprising at least one compound of Formula I and at least one pharmaceutically acceptable excipient.

Preferred is an oral composition comprising a compound of Formula I having an active drug component being combined with an oral pharmaceutically acceptable inert carrier.

Preferred is a method of treating or preventing a disease by administering a pharmacological dose of a compound of Formula I to an animal, preferably wherein said animal is human.

Preferred are compounds of Formula I selected from:
2-{[2-(4-chlorophenoxy)ethyl]sulfanyl}-5,7-dimethyl-[1,2,4]triazolo[1,5-a]pyrimidine;
2-{[2-({5,7-dimethyl-[1,2,4]triazolo[1,5-a]pyrimidin-2-yl}sulfanyl)ethyl](phenyl)amino}-ethan-1-ol;
2-[2-(4-chlorophenoxy)ethoxy]-5,7-dimethyl-[1,2,4]triazolo[1,5-a]pyrimidine;
2-{[2-({5,7-dimethyl-[1,2,4]triazolo[1,5-a]pyrimidin-2-yl}oxy)ethyl](phenyl)amino}ethan-1-ol;
2-{[2-({5,7-diethyl-[1,2,4]triazolo[1,5-a]pyrimidin-2-yl}oxy)ethyl](4-fluorophenyl)amino}ethan-1-ol;
5,7-diethyl-2-[2-(4-fluorophenoxy)ethoxy]-[1,2,4]triazolo[1,5-a]pyrimidine;
5,7-diethyl-2-[2-(4-chlorophenoxy)ethoxy]-[1,2,4]triazolo[1,5-a]pyrimidine;
2-{[2-({5,7-diethyl-[1,2,4]-triazolo[1,5-a]pyrimidin-2-yl}oxy)ethyl](phenyl)amino}ethan-1-ol;
5,7-diethyl-N-(2-phenoxyethyl)-[1,2,4]-triazolo[1,5-a]pyrimidin-2-amine;
2-[(3-{5,7-diethyl-[1,2,4]triazolo[1,5-a]pyrimidin-2-yl}propyl)(4-fluorophenyl)amino]ethan-1-ol;
2-[3-(4-chlorophenoxy)propyl]-5,7-diethyl-[1,2,4]triazolo[1,5-a]pyrimidine; and
2-[3-(4-fluorophenoxy)propyl]-5,7-bis(propan-2-yl)-[1,2,4]triazolo[1,5-a]pyrimidine;
and/or pharmaceutically acceptable salts, solvates, and/or esters thereof.

Preferred are compounds of Formula I selected from:
2-{[2-({5,7-dimethyl-[1,2,4]triazolo[1,5-a]pyrimidin-2-yl}sulfanyl)ethyl](phenyl)amino}-ethan-1-ol;
2-[2-(4-chlorophenoxy)ethoxy]-5,7-dimethyl-[1,2,4]triazolo[1,5-a]pyrimidine;
2-{[2-({5,7-dimethyl-[1,2,4]triazolo[1,5-a]pyrimidin-2-yl}oxy)ethyl](phenyl)amino}ethan-1-ol;
2-{[2-({5,7-diethyl-[1,2,4]triazolo[1,5-a]pyrimidin-2-yl}oxy)ethyl](4-fluorophenyl)amino}ethan-1-ol;
5,7-diethyl-N-(2-phenoxyethyl)-[1,2,4]-triazolo[1,5-a]pyrimidin-2-amine; and
2-[(3-{5,7-diethyl-[1,2,4]triazolo[1,5-a]pyrimidin-2-yl}propyl)(4-fluorophenyl)amino]ethan-1-ol;
and/or pharmaceutically acceptable salts, solvates, and/or esters thereof.

Preferred are compounds of Formula I selected from:
2-[2-(4-chlorophenoxy)ethoxy]-5,7-dimethyl-[1,2,4]triazolo[1,5-a]pyrimidine;
2-{[2-({5,7-dimethyl-[1,2,4]triazolo[1,5-a]pyrimidin-2-yl}oxy)ethyl](phenyl)amino}ethan-1-ol; and
5,7-diethyl-N-(2-phenoxyethyl)-[1,2,4]triazolo[1,5-a]pyrimidin-2-amine;
and/or pharmaceutically acceptable salts, solvates, and/or esters thereof.

Preferred is a pharmaceutical composition comprising at least one of the above enumerated compounds of Formula I and at least one pharmaceutically acceptable excipient.

Preferred is an oral composition comprising at least one of the above enumerated compounds of Formula I having an active drug component being combined with an oral pharmaceutically acceptable inert carrier.

Preferred is a method of treating or preventing a disease by administering a pharmacological dose of at least one of the above enumerated compounds of Formula I to an animal, preferably wherein said animal is human.

Preferred is a method of treating or preventing a disorder, symptom, or disease by administering a pharmacological dose of at least one of the above enumerated compounds of Formula I, wherein the disorder, symptom, or disease is selected from a group consisting of anemia, Alzheimer's disease, Parkinson's disease, multiple sclerosis, Friedreich's ataxia, spinal muscular atrophy, Amyotrophic lateral sclerosis, Huntington's disease, spinal cord injury, traumatic brain injury, ischemic or hemorrhagic stroke, myocardial infarction, heart failure, peripheral nerve injury or blood vessel injury, kidney injury, liver injury, soft-tissue injury, skin injury, bone fracture, glaucoma, optic nerve injury, age-related macular degeneration, chronic diabetic macular edema, retinopathy, peripheral neuropathy, transplantation, alcohol addiction, substance abuse, bipolar disorder, schizophrenia, depression and diabetes.

Other features and advantages of the invention will be apparent from the following detailed description and from the claims.

Exemplary embodiments are summarized herein below.

In an exemplary embodiment, the invention is directed to a compound of formula (I) and/or pharmaceutically acceptable salts, solvates, and/or esters thereof:

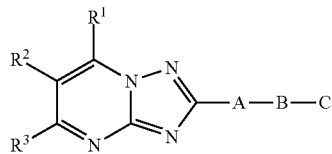

(I)

wherein:

A is S, SO, $SO_2$, O, $NR^4$, $C(R^5R^6)_n$, or bond;

B is a member selected from substituted or unsubstituted alkylene, substituted or unsubstituted alkyleneoxy, substituted or unsubstituted alkylenesulfanyl, substituted or unsubstituted alkylenesulfinyl, substituted or unsubstituted alkylenesulfonyl, substituted or unsubstituted alkyleneamino, substituted or unsubstituted cycloalkylene, and substituted or unsubstituted heterocycloalkylene, and substituted or unsubstituted alkylenecarbonylamino;

C is a member selected from substituted or unsubstituted alkyl, substituted or unsubstituted cycloalkyl, substituted or unsubstituted heterocycloalkyl, substituted or unsubstituted aryl, substituted or unsubstituted aralkyl, substituted or unsubstituted heteroaryl, and substituted or unsubstituted heteroaralkyl;

$R^1$ is a member selected from hydrogen, halo, substituted or unsubstituted alkyl, substituted or unsubstituted haloalkyl, substituted or unsubstituted alkoxy, substituted or unsubstituted cycloalkyl, substituted or unsubstituted aryl, and substituted or unsubstituted heterocycloalkyl;

$R^2$ is a member selected from hydrogen, halo, hydroxy, and substituted or unsubstituted alkyl;

$R^3$ is a member selected from hydrogen, halo, substituted or unsubstituted alkyl, substituted or unsubstituted haloalkyl, substituted or unsubstituted alkoxy, substituted or unsubstituted cycloalkyl, substituted or unsubstituted aryl, and substituted or unsubstituted heterocycloalkyl;

Each $R^4$, $R^5$, and $R^6$ is independently selected from hydrogen, substituted or unsubstituted alkyl, substituted or unsubstituted haloalkyl, substituted or unsubstituted hydroxylakyl, substituted or unsubstituted alkoxyalkyl, substituted or unsubstituted aminoalkyl, substituted or unsubstituted alkylaminoalkyl, and substituted or unsubstituted dialkylaminoalkyl; and n is 0 to 3.

In an exemplary embodiment, the invention is directed to a compound of formula (I) and/or pharmaceutically acceptable salts, solvates, and/or esters thereof:

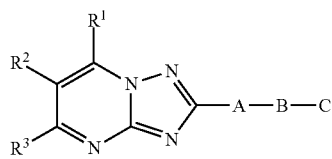

(I)

wherein:

A is S, SO, $SO_2$, O, $NR^4$, $C(R^5R^6)_n$, or bond;

B is a member selected from substituted or unsubstituted $C_2$-$C_8$ alkylene, substituted or unsubstituted $C_2$-$C_8$ alkyleneoxy, substituted or unsubstituted $C_2$-$C_8$ alkylenesulfanyl, substituted or unsubstituted $C_2$-$C_8$ alkylenesulfinyl, substituted or unsubstituted $C_2$-$C_8$ alkylenesulfonyl, substituted or unsubstituted $C_2$-$C_8$ alkyleneamino, substituted or unsubstituted $C_3$-$C_{12}$ cycloalkylene, and substituted or unsubstituted $C_3$-$C_{12}$ heterocycloalkylene;

C is a member selected from substituted or unsubstituted $C_3$-$C_{12}$ cycloalkyl, substituted or unsubstituted $C_3$-$C_{12}$ heterocycloalkyl, substituted or unsubstituted $C_6$-$C_{12}$ aryl and substituted or unsubstituted $C_5$-$C_{12}$ heteroaryl;

$R^1$ is a member selected from hydrogen, halo, substituted or unsubstituted alkyl, substituted or unsubstituted haloalkyl, substituted or unsubstituted alkoxy, substituted or unsubstituted cycloalkyl, substituted or unsubstituted aryl, and substituted or unsubstituted heterocycloalkyl;

$R^2$ is a member selected from hydrogen, halo, hydroxy, and substituted or unsubstituted alkyl;

$R^3$ is a member selected from hydrogen, halo, substituted or unsubstituted alkyl, substituted or unsubstituted haloalkyl, substituted or unsubstituted alkoxy, substituted or unsubstituted cycloalkyl, substituted or unsubstituted aryl, and substituted or unsubstituted heterocycloalkyl; and Each $R^4$, $R^5$, and $R^6$ is independently selected from hydrogen, substituted or unsubstituted alkyl, substituted or unsubstituted haloalkyl, substituted or unsubstituted hydroxylakyl, substituted or unsubstituted alkoxyalkyl, substituted or unsubstituted aminoalkyl, substituted or unsubstituted alkylaminoalkyl, and substituted or unsubstituted dialkylaminoalkyl; and n is 0 to 3.

In an exemplary embodiment according to either of the above paragraphs, wherein:

A is S, SO, $SO_2$, O, $NR^4$, $C(R^5R^6)_n$, or bond;

B is a member selected from substituted or unsubstituted $C_2$-$C_8$ alkylene, substituted or unsubstituted $C_2$-$C_8$ alkyleneoxy, substituted or unsubstituted $C_2$-$C_8$ alkylenesulfanyl, substituted or unsubstituted $C_2$-$C_8$ alkylenesulfinyl, substituted or unsubstituted $C_2$-$C_8$ alkylenesulfonyl, substituted or unsubstituted $C_2$-$C_8$ alkyleneamino, substituted or unsubstituted $C_3$-$C_{12}$ cycloalkylene, and substituted or unsubstituted $C_3$-$C_{12}$ heterocycloalkylene;

C is a member selected from substituted or unsubstituted $C_3$-$C_{12}$ cycloalkyl, substituted or unsubstituted $C_3$-$C_{12}$ heterocycloalkyl, substituted or unsubstituted $C_6$-$C_{12}$ aryl, and substituted or unsubstituted $C_5$-$C_{12}$ heteroaryl;

$R^1$ is a member selected from hydrogen, halo, substituted alkyl, substituted cycloalkyl, substituted aryl, substituted heterocycloalkyl, and haloalkyl;

$R^2$ is a member selected from hydrogen, halo, hydroxy, and unsubstituted alkyl;

$R^3$ is a member selected from hydrogen, halo, substituted alkyl, substituted cycloalkyl, substituted aryl, substituted heterocycloalkyl, and haloalkyl; and Each $R^4$, $R^5$, and $R^6$ is independently selected from hydrogen, substituted or unsubstituted alkyl, substituted or unsubstituted haloalkyl, substituted or unsubstituted hydroxylakyl, substituted or unsubstituted alkoxyalkyl, substituted or unsubstituted aminoalkyl, substituted or unsubstituted alkylaminoalkyl, and substituted or unsubstituted dialkylaminoalkyl; and n is 0 to 3.

In an exemplary embodiment according to any of the above paragraphs, wherein:

A is S, SO, $SO_2$, O, $NR^4$, $C(R^5R^6)_n$, or bond;

B is a member selected from substituted or unsubstituted $C_2$-$C_8$ alkylene, substituted or unsubstituted $C_2$-$C_8$ alkyleneoxy, substituted or unsubstituted $C_2$-$C_8$ alkylenesulfanyl, substituted or unsubstituted $C_2$-$C_8$ alkylenesulfinyl, substituted or unsubstituted $C_2$-$C_8$ alkylenesulfonyl, substituted or unsubstituted $C_2$-$C_8$ alkyleneamino, substituted or unsubstituted $C_3$-$C_{12}$ cycloalkylene, and substituted or unsubstituted $C_3$-$C_{12}$ heterocycloalkylene;

C is a member selected from substituted or unsubstituted $C_3$-$C_{12}$ cycloalkyl, substituted or unsubstituted $C_3$-$C_{12}$ heterocycloalkyl, substituted or unsubstituted $C_6$-$C_{12}$ aryl, and substituted or unsubstituted $C_5$-$C_{12}$ heteroaryl;

$R^1$ is a member selected from hydrogen, unsubstituted alkyl, unsubstituted cycloalkyl, unsubstituted aryl, and unsubstituted heterocycloalkyl;

$R^2$ is a member selected from hydrogen, halo, hydroxy, and unsubstituted alkyl;

$R^3$ is a member selected from hydrogen, unsubstituted alkyl, unsubstituted cycloalkyl, unsubstituted aryl, and unsubstituted heterocycloalkyl; and Each $R^4$, $R^5$, and $R^6$ is independently selected from hydrogen, substituted or unsubstituted alkyl, substituted or unsubstituted haloalkyl, substituted or unsubstituted hydroxylakyl, substituted or unsubstituted alkoxyalkyl, substituted or unsubstituted aminoalkyl, substituted or unsubstituted alkylaminoalkyl, and substituted or unsubstituted dialkylaminoalkyl; and n is 0 to 3.

In an exemplary embodiment according to any of the above paragraphs, wherein:

A is S, SO, $SO_2$, O, $NR^4$, $C(R^5R^6)_n$, or bond;

B is a member selected from substituted or unsubstituted $C_2$-$C_8$ alkylene, substituted or unsubstituted $C_2$-$C_8$ alkyleneoxy, substituted or unsubstituted $C_2$-$C_8$ alkylenesulfanyl, substituted or unsubstituted $C_2$-$C_8$ alkylenesulfinyl, substituted or unsubstituted $C_2$-$C_8$ alkylenesulfonyl, substituted or unsubstituted $C_2$-$C_8$ alkyleneamino, substituted or unsubstituted $C_3$-$C_{12}$ cycloalkylene, and substituted or unsubstituted $C_3$-$C_{12}$ heterocycloalkylene;

C is a member selected from substituted $C_3$-$C_{12}$ cycloalkyl, substituted $C_3$-$C_{12}$ heterocycloalkyl, substituted $C_6$-$C_{12}$ aryl, and substituted $C_5$-$C_{12}$ heteroaryl;

Each $R^1$ and $R^3$ is independently selected from hydrogen, alkyl, haloalkyl, and unsubstituted aryl;

$R^2$ is a member selected from hydrogen, halo, hydroxy, and unsubstituted alkyl; and Each $R^4$, $R^5$, and $R^6$ is independently selected from hydrogen, substituted or unsubstituted alkyl, substituted or unsubstituted haloalkyl, substituted or unsubstituted hydroxylakyl, substituted or unsubstituted alkoxyalkyl, substituted or unsubstituted aminoalkyl, substituted or unsubstituted alkylaminoalkyl, and substituted or unsubstituted dialkylaminoalkyl; and n is 0 to 3.

In an exemplary embodiment according to any of the above paragraphs, wherein:

A is S, SO, $SO_2$, O, $NR^4$, $C(R^5R^6)_n$, or bond;

B is a member selected from substituted or unsubstituted $C_2$-$C_8$ alkylene, substituted or unsubstituted $C_2$-$C_8$ alkyleneoxy, substituted or unsubstituted $C_2$-$C_8$ alkylenesulfanyl, substituted or unsubstituted $C_2$-$C_8$ alkylenesulfinyl, substituted or unsubstituted $C_2$-$C_8$ alkylenesulfonyl, substituted or unsubstituted $C_2$-$C_8$ alkyleneamino, substituted or unsubstituted $C_3$-$C_{12}$ cycloalkylene, and substituted or unsubstituted $C_3$-$C_{12}$ heterocycloalkylene;

C is a member selected from unsubstituted $C_3$-$C_{12}$ cycloalkyl, unsubstituted $C_3$-$C_{12}$ heterocycloalkyl, unsubstituted $C_6$-$C_{12}$ aryl, and unsubstituted $C_5$-$C_{12}$ heteroaryl;

Each $R^1$ and $R^3$ is independently selected from hydrogen, alkyl, haloalkyl, and unsubstituted aryl;

$R^2$ is a member selected from hydrogen, halo, hydroxy, and unsubstituted alkyl; and Each $R^4$, $R^5$, and $R^6$ is independently selected from hydrogen, substituted or unsubstituted alkyl, substituted or unsubstituted haloalkyl, substituted or unsubstituted hydroxylakyl, substituted or unsubstituted alkoxyalkyl, substituted or unsubstituted aminoalkyl, substituted or unsubstituted alkylaminoalkyl, and substituted or unsubstituted dialkylaminoalkyl; and n is 0 to 3.

In an exemplary embodiment according to any of the above paragraphs, wherein:

Each $R^1$ and $R^3$ is independently selected from hydrogen, methyl, ethyl, —$CH(CH_3)_2$, —$CF_3$, —$CHF_2$, —$CH_2F$—, —$(CH_2)_2$—OH, —$(CH_2)_2$—$N(CH_3)_2$; and phenyl.

In an exemplary embodiment according to any of the above paragraphs, wherein Each $R^1$ and $R^3$ is independently selected from hydrogen, methyl, ethyl, and —$CH(CH_3)_2$; $R^2$ is hydrogen; and C is substituted or unsubstituted phenyl.

In an exemplary embodiment according to any of the above paragraphs, wherein:

C is substituted phenyl.

In an exemplary embodiment according to any of the above paragraphs, wherein: C is phenyl substituted with —F, —Cl, —Br, —I, methyl, ethyl, isopropyl, tert-butyl, methoxy, —$(CH_2)_2$—OH, or —$(CH_2)_2$—$N(CH_3)_2$.

In an exemplary embodiment according to any of the above paragraphs, wherein: B is —$(CH_2)_2$—O—, —$(CH_2)_2$—NH—, —$(CH_2)_2$—$N(CH_2CH_2OC(O)CH_3)$—, —$(CH_2)_2$—$N(CH_2CH_2OH)$—, —$(CH_2)_3$—, —$(CH_2)_2$—S—, —$(CH_2)_2$—S(O)—, or —$(CH_2)_2$—$SO_2$—.

In an exemplary embodiment according to any of the above paragraphs, wherein:

A is S, SO, $SO_2$, O, NH, $N(CH_3)$, $N(CH_2CH_3)$, $N(CH_2CH_2OH)$, or $CH_2$;

B is a member selected from substituted or unsubstituted alkylene, substituted or unsubstituted alkyleneoxy, substituted or unsubstituted alkylenesulfanyl, substituted or unsubstituted alkylenesulfinyl, substituted or unsubstituted alkylenesulfonyl, substituted or unsubstituted alkyleneamino, substituted or unsubstituted cycloalkylene, and substituted or unsubstituted heterocycloalkylene;

C is a member selected from substituted or unsubstituted alkyl, substituted or unsubstituted cycloalkyl, substituted or unsubstituted heterocycloalkyl, substituted or unsubstituted aryl, substituted or unsubstituted aralkyl, substituted or unsubstituted heteroaryl, and substituted or unsubstituted heteroaralkyl;

$R^1$ is a member selected from hydrogen, halo, substituted or unsubstituted alkyl, substituted or unsubstituted haloalkyl, substituted or unsubstituted alkoxy, substituted or unsubstituted cycloalkyl, substituted or unsubstituted aryl, and substituted or unsubstituted heterocycloalkyl;

$R^2$ is a member selected from hydrogen, halo, hydroxy, and substituted or unsubstituted alkyl; and $R^3$ is a member selected from hydrogen, halo, substituted or unsubstituted alkyl, substituted or unsubstituted haloalkyl, substituted or unsubstituted alkoxy, substituted or unsubstituted cycloalkyl, substituted or unsubstituted aryl, and substituted or unsubstituted heterocycloalkyl.

In an exemplary embodiment according to any of the above paragraphs, wherein:

A is O, NH, N(CH$_3$), N(CH$_2$CH$_3$), or N(CH$_2$CH$_2$OH);

B is a member selected from substituted or unsubstituted C$_2$-C$_8$ alkylene, substituted or unsubstituted C$_2$-C$_8$ alkyleneoxy, substituted or unsubstituted C$_2$-C$_8$ alkylenesulfanyl, substituted or unsubstituted C$_2$-C$_8$ alkylenesulfinyl, substituted or unsubstituted C$_2$-C$_8$ alkylenesulfonyl, substituted or unsubstituted C$_2$-C$_8$ alkyleneamino, substituted or unsubstituted C$_3$-C$_{12}$ cycloalkylene, and substituted or unsubstituted C$_3$-C$_{12}$ heterocycloalkylene;

C is a member selected from substituted or unsubstituted C$_3$-C$_{12}$ cycloalkyl, substituted or unsubstituted C$_3$-C$_{12}$ heterocycloalkyl, substituted or unsubstituted C$_6$-C$_{12}$ aryl, and substituted or unsubstituted C$_5$-C$_{12}$ heteroaryl;

R$^1$ is a member selected from hydrogen, halo, substituted or unsubstituted alkyl, substituted or unsubstituted haloalkyl, substituted or unsubstituted alkoxy, substituted or unsubstituted cycloalkyl, substituted or unsubstituted aryl, and substituted or unsubstituted heterocycloalkyl;

R$^2$ is a member selected from hydrogen, halo, hydroxy, and substituted or unsubstituted alkyl; and R$^3$ is a member selected from hydrogen, halo, substituted or unsubstituted alkyl, substituted or unsubstituted haloalkyl, substituted or unsubstituted alkoxy, substituted or unsubstituted cycloalkyl, substituted or unsubstituted aryl, and substituted or unsubstituted heterocycloalkyl.

In an exemplary embodiment according to any of the above paragraphs, wherein:

A is S;

B is a member selected from substituted or unsubstituted C$_2$-C$_8$ alkylene, substituted or unsubstituted C$_2$-C$_8$ alkyleneoxy, substituted or unsubstituted C$_2$-C$_8$ alkylenesulfanyl, substituted or unsubstituted C$_2$-C$_8$ alkylenesulfinyl, substituted or unsubstituted C$_2$-C$_8$ alkylenesulfonyl, substituted or unsubstituted C$_2$-C$_8$ alkyleneamino, substituted or unsubstituted C$_3$-C$_{12}$ cycloalkylene, and substituted or unsubstituted C$_3$-C$_{12}$ heterocycloalkylene;

C is a member selected from substituted or unsubstituted C$_3$-C$_{12}$ cycloalkyl, substituted or unsubstituted C$_3$-C$_{12}$ heterocycloalkyl, substituted or unsubstituted C$_6$-C$_{12}$ aryl, and substituted or unsubstituted C$_5$-C$_{12}$ heteroaryl;

R$^1$ is a member selected from hydrogen, halo, substituted or unsubstituted alkyl, substituted or unsubstituted haloalkyl, substituted or unsubstituted alkoxy, substituted or unsubstituted cycloalkyl, substituted or unsubstituted aryl, and substituted or unsubstituted heterocycloalkyl;

R$^2$ is a member selected from hydrogen, halo, hydroxy, and substituted or unsubstituted alkyl; and R$^3$ is a member selected from hydrogen, halo, substituted or unsubstituted alkyl, substituted or unsubstituted haloalkyl, substituted or unsubstituted alkoxy, substituted or unsubstituted cycloalkyl, substituted or unsubstituted aryl, and substituted or unsubstituted heterocycloalkyl.

In an exemplary embodiment according to any of the above paragraphs, wherein:

A is S;

B is a member selected from substituted or unsubstituted C$_2$-C$_8$ alkylene, substituted or unsubstituted C$_2$-C$_8$ alkyleneoxy, substituted or unsubstituted C$_2$-C$_8$ alkylenesulfanyl, substituted or unsubstituted C$_2$-C$_8$ alkylenesulfinyl, substituted or unsubstituted C$_2$-C$_8$ alkylenesulfonyl, substituted or unsubstituted C$_2$-C$_8$ alkyleneamino, substituted or unsubstituted C$_3$-C$_{12}$ cycloalkylene, and substituted or unsubstituted C$_3$-C$_{12}$ heterocycloalkylene;

C is a member selected from substituted or unsubstituted C$_3$-C$_{12}$ cycloalkyl, substituted or unsubstituted C$_3$-C$_{12}$ heterocycloalkyl, substituted or unsubstituted C$_6$-C$_{12}$ aryl, and substituted or unsubstituted C$_5$-C$_{12}$ heteroaryl;

R$^1$ is a member selected from hydrogen, halo, substituted or unsubstituted C$_2$-C$_8$ alkyl, substituted or unsubstituted haloalkyl, substituted or unsubstituted alkoxy, substituted or unsubstituted cycloalkyl, substituted or unsubstituted aryl, and substituted or unsubstituted heterocycloalkyl;

R$^2$ is a member selected from hydrogen, halo, hydroxy, and substituted or unsubstituted alkyl; and R$^3$ is a member selected from hydrogen, halo, substituted or unsubstituted C$_2$-C$_8$ alkyl, substituted or unsubstituted haloalkyl, substituted or unsubstituted alkoxy, substituted or unsubstituted cycloalkyl, substituted or unsubstituted aryl, and substituted or unsubstituted heterocycloalkyl.

In an exemplary embodiment according to any of the above paragraphs, wherein:

A is bond;

B is a member selected from substituted or unsubstituted C$_3$-C$_8$ alkylene, substituted or unsubstituted C$_3$-C$_8$ alkyleneoxy, substituted or unsubstituted C$_3$-C$_8$ alkylenesulfanyl, substituted or unsubstituted C$_3$-C$_8$ alkylenesulfinyl, substituted or unsubstituted C$_3$-C$_8$ alkylenesulfonyl, substituted or unsubstituted C$_3$-C$_8$ alkyleneamino, substituted or unsubstituted C$_3$-C$_{12}$ cycloalkylene, and substituted or unsubstituted C$_3$-C$_{12}$ heterocycloalkylene;

C is a member selected from substituted or unsubstituted C$_3$-C$_{12}$ cycloalkyl, substituted or unsubstituted C$_3$-C$_{12}$ heterocycloalkyl, substituted or unsubstituted C$_6$-C$_{12}$ aryl, and substituted or unsubstituted C$_5$-C$_{12}$ heteroaryl;

R$^1$ is a member selected from hydrogen, halo, substituted or unsubstituted alkyl, substituted or unsubstituted haloalkyl, substituted or unsubstituted alkoxy, substituted or unsubstituted cycloalkyl, substituted or unsubstituted aryl, and substituted or unsubstituted heterocycloalkyl;

R$^2$ is a member selected from hydrogen, halo, hydroxy, and substituted or unsubstituted alkyl; and R$^3$ is a member selected from hydrogen, halo, substituted or unsubstituted alkyl, substituted or unsubstituted haloalkyl, substituted or unsubstituted alkoxy, substituted or unsubstituted cycloalkyl, substituted or unsubstituted aryl, and substituted or unsubstituted heterocycloalkyl.

In an exemplary embodiment according to any of the above paragraphs, wherein: A is S; B is —(CH$_2$)$_2$—O—; C is phenyl substituted with one or more methyl, ethyl, isopropyl, tert-butyl, methoxy, —(CH$_2$)$_2$—OH, —(CH$_2$)$_2$—N(CH$_3$)$_2$, —F, —Cl, —Br, or —I; R$^1$ and R$^3$ are each methyl; and R$^2$ is hydrogen.

In an exemplary embodiment according to any of the above paragraphs, wherein: A is O; B is —(CH$_2$)$_2$—O—, —(CH$_2$)$_2$—S—, or —(CH$_2$)$_2$—N(CH$_2$CH$_2$OH)—; C is unsubstituted phenyl, or phenyl substituted with alkyl, alkoxy, or halo; R$^1$ and R$^3$ are each methyl, ethyl, or isopropyl; and R$^2$ is hydrogen.

In an exemplary embodiment according to any of the above paragraphs, wherein: A is O; B is —(CH$_2$)$_2$—O—; C is phenyl substituted with chloro or fluoro; R$^1$ and R$^3$ are each methyl; and R$^2$ is hydrogen.

In an exemplary embodiment according to any of the above paragraphs, wherein: A is NH or N(CH$_3$); B is —(CH$_2$)$_2$—O—; C is unsubstituted phenyl, or phenyl substituted with alkyl, alkoxy, or halo; R$^1$ and R$^3$ are each methyl, ethyl, or isopropyl; and R$^2$ is hydrogen.

In an exemplary embodiment, according to any of the above paragraphs, wherein: A is bond; B is —(CH$_2$)$_3$—O—, —(CH$_2$)$_4$—O—, —(CH$_2$)$_3$—N(CH$_2$CH$_2$OH)—, or —(CH$_2$)$_3$—N(CH$_2$CH$_2$OC(O)CH$_3$)—; C is unsubstituted phenyl, or phenyl substituted with alkyl, alkoxy, or halo; R¹ and R³ are each methyl, ethyl, isopropyl, or —CF₃; and R² is hydrogen.

In an exemplary embodiment, the invention is a pharmaceutical composition comprising at least one compound from any of the above paragraphs and at least one pharmaceutically acceptable excipient.

In an exemplary embodiment, the invention is an oral composition comprising a compound from any of the above paragraphs having an active drug component being combined with an oral pharmaceutically acceptable inert carrier.

In an exemplary embodiment, the invention is a method of treating or preventing a disease by administering a pharmacological dose of a compound from any of the above paragraphs to an animal.

In an exemplary embodiment, the invention is a method of treating or preventing a disease by administering a pharmacological dose of a compound from any of the above paragraphs wherein the said animal is human.

In an exemplary embodiment, according to any of the above paragraphs, the invention is a compound or pharmaceutically acceptable salts, solvates, and/or esters thereof, selected from the group consisting of:
2-{[2-(4-chlorophenoxy)ethyl]sulfanyl}-5,7-dimethyl-[1,2,4]-triazolo[1,5-a]pyrimidine;
2-{[2-(4-chlorophenoxy)ethyl]sulfanyl}-5-methyl-[1,2,4]triazolo[1,5-a]pyrimidine;
2-{[2-(4-chloro-3-fluorophenoxy)ethyl]sulfanyl}-5,7-dimethyl-[1,2,4]triazolo[1,5-a]pyrimidine;
2-{[2-({5,7-dimethyl-[1,2,4]-triazolo[1,5-a]pyrimidin-2-yl}sulfanyl)ethyl]-(phenyl)amino}ethan-1-ol;
2-[3-(4-chlorophenoxy)propyl]-5,7-diethyl-[1,2,4]-triazolo[1,5-a]pyrimidine;
2-[(3-{5,7-diethyl-[1,2,4]triazolo[1,5-a]pyrimidin-2-yl}propyl)(4-fluorophenyl)amino]ethan-1-ol;
2-[2-(4-chlorophenoxy)ethoxy]-5,7-dimethyl-[1,2,4]triazolo[1,5-a]pyrimidine;
2-{[2-({5,7-dimethyl-[1,2,4]triazolo[1,5-a]pyrimidin-2-yl}oxy)ethyl]-(phenyl)amino}ethan-1-ol;
2-{[2-({5,7-diethyl-[1,2,4]triazolo[1,5-a]pyrimidin-2-yl}oxy)ethyl]-(4-fluorophenyl)amino}ethan-1-ol;
2-{[2-({5,7-diethyl-[1,2,4]triazolo[1,5-a]pyrimidin-2-yl}oxy)ethyl]-(phenyl)amino ethan-1-ol;
5,7-diethyl-N-(2-phenoxyethyl)-[1,2,4]triazolo[1,5-a]pyrimidin-2-amine;
2-[3-(4-chloro-3-fluorophenoxy)propyl]-5,7-bis(propan-2-yl)-[1,2,4]triazolo[1,5-a]pyrimidine;
2-[3-(4-fluorophenoxy)propyl]-5,7-bis(propan-2-yl)-[1,2,4]-triazolo[1,5-a]pyrimidine;
2-[2-(4-chlorophenoxy)ethoxy]-5,7-diethyl-[1,2,4]-triazolo[1,5-a]pyrimidine;
2-[2-(4-fluorophenoxy)ethoxy]-5,7-diethyl-[1,2,4]triazolo[1,5-a]pyrimidine;
2-{2-[(4-chlorophenyl)sulfanyl]ethoxy}-5,7-diethyl-[1,2,4]triazolo[1,5-a]pyrimidine;
2-[3-(4-chlorophenoxy)propyl]-5-methyl-7-(trifluoromethyl)-[1,2,4]triazolo[1,5-a]pyrimidine;
2-({5,7-dimethyl-[1,2,4]triazolo[1,5-a]pyrimidin-2-yl}sulfanyl)-N-(4-methoxyphenyl)acetamide.

In an exemplary embodiment, the invention is a pharmaceutical composition comprising at least one compound from any of the paragraphs above and at least one pharmaceutically acceptable excipient.

In an exemplary embodiment, the invention is an oral composition comprising a compound from any of the paragraphs above having an active drug component being combined with an oral pharmaceutically acceptable inert carrier.

In an exemplary embodiment, the invention is a method of treating or preventing a disease by administering a pharmacological dose of a compound from any of the paragraphs above to an animal.

In an exemplary embodiment, the invention is a method of treating or preventing a disease by administering a pharmacological dose of a compound from any of the above paragraphs wherein the said animal is human.

In an exemplary embodiment, according to any of the above paragraphs, the invention is a method of treating or preventing a disorder, symptom, or disease by administering a pharmacological dose of compound from any of the above paragraphs, wherein the disorder, symptom, or disease is selected from a group consisting of anemia, Alzheimer's disease, Parkinson's disease, multiple sclerosis, Friedreich's ataxia, spinal muscular atrophy, Amyotrophic lateral sclerosis, Huntington's disease, spinal cord injury, traumatic brain injury, ischemic or hemorrhagic stroke, myocardial infarction, heart failure, peripheral nerve injury or blood vessel injury, kidney injury, liver injury, soft-tissue injury, skin injury, bone fracture, glaucoma, optic nerve injury, age-related macular degeneration, chronic diabetic macular edema, retinopathy, peripheral neuropathy, transplantation, alcohol addiction, substance abuse, bipolar disorder, schizophrenia, depression and diabetes.

In an exemplary embodiment, according to any of the above paragraphs, the invention is a method of treating an injury or physiological disorder, syndrome, or disease comprising: expanding stem cells by subjecting them to an effective amount of a compound from any of the paragraphs above or a pharmaceutically acceptable salt and/or solvate thereof, and administering the stem cells to an animal in need of such stem cells.

In an exemplary embodiment according to any of the above paragraphs, the invention is a compound of Formula I

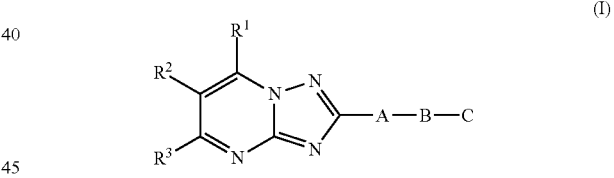

or pharmaceutically acceptable salts, solvates, and/or esters thereof, wherein:

A is S, SO, SO₂, O, NR⁴, C(R⁵R⁶)$_n$, or bond;

B is a member selected from alkylene, alkyleneoxy, alkylenesulfanyl, alkylenesulfinyl, alkylenesulfonyl, alkyleneamino, alkylene(2-hydroxyethyl)amino, alkylene(2-acetyloxyethyl)amino, cycloalkylene, heterocycloalkylene, and alkylenecarbonylamino;

C is a member selected from substituted or unsubstituted alkyl, substituted or unsubstituted cycloalkyl, substituted or unsubstituted heterocycloalkyl, substituted or unsubstituted aryl, substituted or unsubstituted aralkyl, substituted or unsubstituted heteroaryl, and substituted or unsubstituted heteroaralkyl;

R¹ is a member selected from hydrogen, halo, substituted or unsubstituted alkyl, substituted or unsubstituted haloalkyl, substituted or unsubstituted alkoxy, substituted or unsubstituted cycloalkyl, substituted or unsubstituted aryl, and substituted or unsubstituted heterocycloalkyl;

R² is a member selected from hydrogen, halo, hydroxy, and substituted or unsubstituted alkyl;

R³ is a member selected from hydrogen, halo, substituted or unsubstituted alkyl, substituted or unsubstituted haloalkyl, substituted or unsubstituted alkoxy, substituted or unsubstituted cycloalkyl, substituted or unsubstituted aryl, and substituted or unsubstituted heterocycloalkyl;

Each $R^4$, $R^5$, and $R^6$ is independently selected from hydrogen, substituted or unsubstituted alkyl, substituted or unsubstituted haloalkyl, substituted or unsubstituted hydroxylakyl, substituted or unsubstituted alkoxyalkyl, substituted or unsubstituted aminoalkyl, substituted or unsubstituted alkylaminoalkyl, and substituted or unsubstituted dialkylaminoalkyl; and n is 0 to 3.

In an exemplary embodiment according to any of the above paragraphs, wherein:

A is S, SO, $SO_2$, O, $NR^4$, or $CH_2$;

B is a member selected from alkylene, alkyleneoxy, alkylenesulfanyl, alkylenesulfinyl, alkylenesulfonyl, alkyleneamino, alkylene(2-hydroxyethyl)amino, and alkylene(2-acetylcarboxyethyl)amino;

C is a member selected from substituted or unsubstituted alkyl, substituted or unsubstituted cycloalkyl, substituted or unsubstituted heterocycloalkyl, substituted or unsubstituted aryl, and substituted or unsubstituted heteroaryl;

$R^1$ is a member selected from hydrogen, halo, substituted or unsubstituted alkyl, substituted or unsubstituted haloalkyl, and substituted or unsubstituted alkoxy;

$R^2$ is a member selected from hydrogen, halo, hydroxy, and substituted or unsubstituted alkyl;

$R^3$ is a member selected from hydrogen, halo, substituted or unsubstituted alkyl, substituted or unsubstituted haloalkyl, and substituted or unsubstituted alkoxy; and $R^4$ is hydrogen or alkyl.

In an exemplary embodiment according to any of the above paragraphs, wherein:

$R^1$ is methyl, trifluoromethyl, ethyl or isopropyl, $R^2$ is hydrogen, $R^3$ is methyl, trifluoromethyl, ethyl or isopropyl, A is S, O, NH, or $CH_2$, B is ethyleneoxy or ethylene(2-hydroxyethyl)amino, and C is phenyl optionally substituted with 1-3 groups selected from halo, methoxy, and isopropyl.

In an exemplary embodiment, according to any of the above paragraphs, the invention is a compound or pharmaceutically acceptable salts, solvates, and/or esters thereof, selected from the group consisting of:

2-{[2-(4-chlorophenoxy)ethyl]sulfanyl}-5,7-dimethyl-[1,2,4]triazolo[1,5-a]pyrimidine;
2-{[2-({5,7-dimethyl-[1,2,4]triazolo[1,5-a]pyrimidin-2-yl}sulfanyl)ethyl](phenyl)amino}-ethan-1-ol;
2-[2-(4-chlorophenoxy)ethoxy]-5,7-dimethyl-[1,2,4]triazolo[1,5-a]pyrimidine;
2-{[2-({5,7-dimethyl-[1,2,4]-triazolo[1,5-a]pyrimidin-2-yl}oxy)ethyl](phenyl)amino}ethan-1-ol;
2-{[2-({5,7-diethyl-[1,2,4]triazolo[1,5-a]pyrimidin-2-yl}oxy)ethyl](4-fluorophenyl)amino}ethan-1-ol;
5,7-diethyl-2-[2-(4-fluorophenoxy)ethoxy]-[1,2,4]triazolo[1,5-a]pyrimidine;
5,7-diethyl-2-[2-(4-chlorophenoxy)ethoxy]-[1,2,4]triazolo[1,5-a]pyrimidine;
2-{[2-({5,7-diethyl-[1,2,4]-triazolo[1,5-a]pyrimidin-2-yl}oxy)ethyl](phenyl)amino}ethan-1-ol;
5,7-diethyl-N-(2-phenoxyethyl)-[1,2,4]triazolo[1,5-a]pyrimidin-2-amine;
2-[(3-{5,7-diethyl-[1,2,4]triazolo[1,5-a]pyrimidin-2-yl}propyl)(4-fluorophenyl)amino]ethan-1-ol;
2-[3-(4-chlorophenoxy)propyl]-5,7-diethyl-[1,2,4]-triazolo[1,5-a]pyrimidine; and
2-[3-(4-fluorophenoxy)propyl]-5,7-bis(propan-2-yl)-[1,2,4]triazolo[1,5-a]pyrimidine;

and/or pharmaceutically acceptable salts, solvates, and/or esters thereof.

In an exemplary embodiment, according to any of the above paragraphs, the invention is a compound or pharmaceutically acceptable salts, solvates, and/or esters thereof, selected from the group consisting of:

2-{[2-({5,7-dimethyl-[1,2,4]triazolo[1,5-a]pyrimidin-2-yl}sulfanyl)ethyl](phenyl)amino}-ethan-1-ol;
2-[2-(4-chlorophenoxy)ethoxy]-5,7-dimethyl-[1,2,4]triazolo[1,5-a]pyrimidine;
2-{[2-({5,7-dimethyl-[1,2,4]triazolo[1,5-a]pyrimidin-2-yl}oxy)ethyl](phenyl)amino}ethan-1-ol;
2-{[2-({5,7-diethyl-[1,2,4]triazolo[1,5-a]pyrimidin-2-yl}oxy)ethyl](4-fluorophenyl)amino}ethan-1-ol;
5,7-diethyl-N-(2-phenoxyethyl)-[1,2,4]triazolo[1,5-a]pyrimidin-2-amine; and
2-[(3-{5,7-diethyl-[1,2,4]triazolo[1,5-a]pyrimidin-2-yl}propyl)(4-fluorophenyl)amino]ethan-1-ol; and/or pharmaceutically acceptable salts, solvates, and/or esters thereof.

In an exemplary embodiment, according to any of the above paragraphs, the invention is a compound or pharmaceutically acceptable salts, solvates, and/or esters thereof, selected from the group consisting of:

2-[2-(4-chlorophenoxy)ethoxy]-5,7-dimethyl-[1,2,4]triazolo[1,5-a]pyrimidine;
2-{[2-(5,7-dimethyl-[1,2,4]triazolo[1,5-a]pyrimidin-2-yl}oxy)ethyl](phenyl)amino-1 ethan-1-ol; and
5,7-diethyl-N-(2-phenoxyethyl)-[1,2,4]triazolo[1,5-a]pyrimidin-2-amine;

and/or pharmaceutically acceptable salts, solvates, and/or esters thereof.

In an exemplary embodiment, the invention is a pharmaceutical composition comprising at least one compound from any of the above paragraphs and at least one pharmaceutically acceptable excipient.

In an exemplary embodiment, the invention is an oral composition comprising at least one compound from any of the above paragraphs having an active drug component being combined with an oral pharmaceutically acceptable inert carrier.

In an exemplary embodiment, the invention is a method of treating or preventing a disease by administering a pharmacological dose of at least one compound from any of the above paragraphs to an animal.

In an exemplary embodiment, the invention is a method of treating or preventing a disease by administering a pharmacological dose of a compound from any of the above paragraphs wherein the said animal is human.

In an exemplary embodiment, according to any of the above paragraphs, the invention is a method of treating or preventing a disorder, symptom, or disease by administering a pharmacological dose of at least one compound from any of the above paragraphs, wherein the disorder, symptom, or disease is selected from a group consisting of anemia, Alzheimer's disease, Parkinson's disease, multiple sclerosis, Friedreich's ataxia, spinal muscular atrophy, Amyotrophic lateral sclerosis, Huntington's disease, spinal cord injury, traumatic brain injury, ischemic or hemorrhagic stroke, myocardial infarction, heart failure, peripheral nerve injury or blood vessel injury, kidney injury, liver injury, soft-tissue injury, skin injury, bone fracture, glaucoma, optic nerve injury, age-related macular degeneration, chronic diabetic macular edema, retinopathy, peripheral neuropathy, transplantation, alcohol addiction, substance abuse, bipolar disorder, schizophrenia, depression and diabetes.

III. Utility

The present invention is directed to materials and methods to protect or enhance the function or viability of erythropoietin-responsive mammalian cells, tissues and organs. In a particular aspect of the invention the pharmaceutical compositions are used to protect or enhance the function or viability mammalian cells, tissues and organs expressing the tissue-protective EPO receptor. Conditions and diseases treatable or preventable by the materials and methods of the present invention include but are not limited to diseases of the central nervous system, peripheral nervous system, neuropsychologic disorders, neurological diseases involving neuronal injury or stress, organ injury, tissue injury, and transplantations.

In one aspect, the materials and methods of the present invention are used to enhance the function or survival of cells of the nervous system. In particular, such conditions for which treatment or prevention by the present invention is provided include but are not limited to neurological and psychological conditions, such as Parkinson's disease, Alzheimer's disease, dementia, age-related loss of cognitive function, Lewy body dementia, Huntington's disease, Batten's disease, Guillain-Barre syndrome, Tourette's syndrome, prion diseases, such as spongiform encephalopathies, Friedreich's ataxia and other ataxias, Wilson's disease, multiple sclerosis, traumatic brain injury, spinal cord injury, peripheral neuropathy, optic nerve injury, retinopathy, including diabetic neuropathy, pain, peripheral nerve injury, depression, mania, obsessive-compulsive disorder, autism, schizophrenia, attention deficit hyperactivity disorder, bipolar disorder spinal muscular atrophy, myotonic dystrophy, epilepsy and chronic seizure disorder, amyotrophic lateral sclerosis, ischemic or hemorrhagic stroke, and addiction or substance abuse, such as dependence on alcohol, drugs, tobacco or gambling.

In another aspect, the materials and methods of the present invention are used to enhance the function or survival of cells in peripheral tissues and organs. In particular, such conditions for which treatment or prevention by the present invention is provided include but are not limited to transplantation, acute kidney injury, chronic kidney disease, liver injury, hepatitis, myocardial infarction, cardiomyopathy, soft tissue injury, skin injury, tissue-injuries caused by chemotherapy or radiation, tissue-injuries and pain associated with sarcoidosis, tissue-injuries associated with autoimmune diseases, such as rheumatoid arthritis or systemic lupus erythematosus, hearing loss, vision impairment, bone fracture, diabetes, glaucoma, age-related macular degeneration, chronic diabetic macular edema, and diabetes.

In another aspect, the materials and methods of the present invention are used to prevent cellular damage or cell death associated with a mitochondrial disorder or dysfunction, which are the cause of a variety of diseases typified by neuronal and organ injury. In particular, such mitochondrial disorders or dysfunctions for which treatment or prevention by the present invention is provided include but are not limited to Friedreich's ataxia, Myoclonic epilepsy with ragged red fibers (MERRF), Mitochondrial myopathy, Encephalopathy, Lactacidosis, and Stroke (MELAS), Leber's hereditary optic neuropathy (LHON), Dominant optic atrophy (DOA), Leigh disease, and Kearns-Sayre syndrome (KSS).

In another aspect, the compounds of this invention are useful in the treatment of any disease or condition, such as anemia, resulting in the decrease of erythrocytes below what is considered to be normal for a healthy individual. There are several causative factors, e.g., chronic kidney disease, palliative chemotherapy of cancer, Zidovudine-treatment of HIV infection, iron deficiency, erythropoietin deficiency, erythropoietin receptor deficiency, pregnancy, autoimmunity, such as pure red cell aplasia, radiation injury or treatment, surgical procedures, such as liver or bone marrow transplantation. Compounds of this invention are also useful in prophylaxis of anemia, for example for blood donors or patients scheduled to undergo chemotherapy. The compounds of this invention are also useful to support survival of cells, tissues, and organs ex vivo, and for the ex vivo production of red blood cells and other erythropoietin-responsive cells for transplantation, and for stem cell therapies.

IV. Methods of Making the Compounds

Compounds of this invention can be made by the synthetic procedures described below. The starting materials and reagents used in preparing these compounds are either available from commercial suppliers such as Sigma Aldrich (St. Louis, Mo.), Alfa Aesar (Ward Hill, Mass.), or Acros Organics (Geel, Belgium), or are prepared by methods known to those skilled in the art following procedures set forth in references such as *Fieser and Fieser's Reagents for Organic Synthesis*, Volumes 1-17 (John Wiley and Sons, 1991); *Rodd's Chemistry of Carbon Compounds*, Volumes 1-5 and Supplementals (Elsevier Science Publishers, 1989); *Organic Reactions*, Volumes 1-40 (John Wiley and Sons, 1991), March's *Advanced Organic Chemistry*, (John Wiley and Sons, $6^{th}$ Edition, 2007) and *Larock's Comprehensive Organic Transformations* (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C. Unless otherwise stated (as in the case of an hydrogenation), all reactions are performed under an atmosphere of nitrogen. Compounds and/or compounds of formulas described herein that may be prepared through the syntheses described herein may exist as a single isomer or a mixture of isomers.

The following reaction schemes illustrate the preparation of the compounds and/or compounds of formulas described herein (i.e., Formula I). Unless otherwise stated, each A, B, C, $R^1$, $R^2$, $R^3$, $R^4$, $R^5$ and $R^6$ groups in the reaction Schemes and the discussion that follows are as defined in the Summary of the Invention above.

Scheme 1

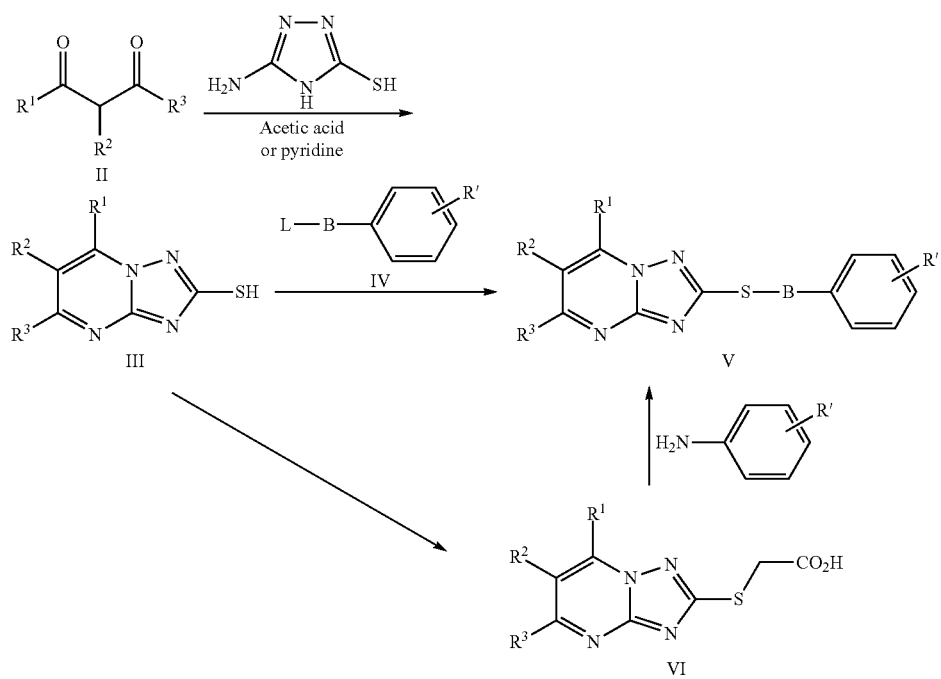

Compounds and/or compounds of the formulas described herein (such as Formula I) where A is thio can be prepared according the reaction Scheme I. For example, the compound 3-amino-5-mercapto-1,2,4-triazole can be reacted with complimentary reactive 1,3-dicarbonyl compounds of Formula II, or their protected derivatives, such as 2,4-pentanedione, 3,5-heptanedione, 4,4-dimethoxy-2-butanone, and the like, under suitable reaction conditions for cyclo-condensation to obtain [1,2,4]triazolo[1,5-a]pyrimidine-2-thiol of Formula III, where each $R^1$, $R^2$, and $R^3$ is as defined in the Summary of the Invention. Preferably, the solvent is acetic acid or pyridine and the temperature is 100-125° C. Mixtures of $R^1$ and $R^3$ substituted isomers of Formula III can be synthesized from asymmetrically substituted 1,3-dicarbonyl compounds and can be separated by chromatography. Alternatively, isomers can be synthesized individually by methods that are described in Monte et al., J. Heterocyclic Chem (1989) 26:1393), the disclosure of which is incorporated herein by reference in its entirety. Preferably, $R^1$ and $R^3$ are identical substitutions. Compounds of Formula III can then be alkylated with a reagent of Formula IV, where L is a leaving group as defined in the Summary of the Invention, B is as defined in the Summary of the Invention, and $R^1$ is a ring system substituent as defined in the Summary of the Invention. For example, a reagent such as IV where L is bromo can be reacted in the presence of a base such as potassium or sodium carbonate with the thiol of III to obtain thioethers of the Formula V. Alternatively, a reagent of Formula IV where L is triphenylphosphineoxy can be obtained by reacting alcohols in the presence of triphenylphosphine and an azo electrophile such as diethyl azodicarbonate or diisopropyl azodicarboxylate, and then reacted with thiols of Formula III to obtain compounds of Formula V. Alternatively, thiols of Formula III can be reacted with an alkylating agent such as chloroacetic acid, optionally in the presence of a base such as sodium or potassium hydroxide and a solvent such as water, to obtain a carbonyl compound of the Formula VI. The compound of Formula VI may be further reacted with a nucleophile such as a substituted aniline, optionally in the presence of an activating reagent such as N,N-dicyclohexylcarbodiimide in a polar aprotic solvent such as N,N-dimethylformamide. Thiols of Formula III can also be reacted with an alkylating agent such as 2-bromoethanol in the presence of a base such as sodium or potassium carbonate and a solvent such as N,N-dimethylformamide to obtain an alcohol which may be further reacted with a nucleophile in the presence of triphenylphosphine and diethyl azodicarbonate or diisopropyl azodicarboxylate to obtain compounds of Formula V.

Scheme II

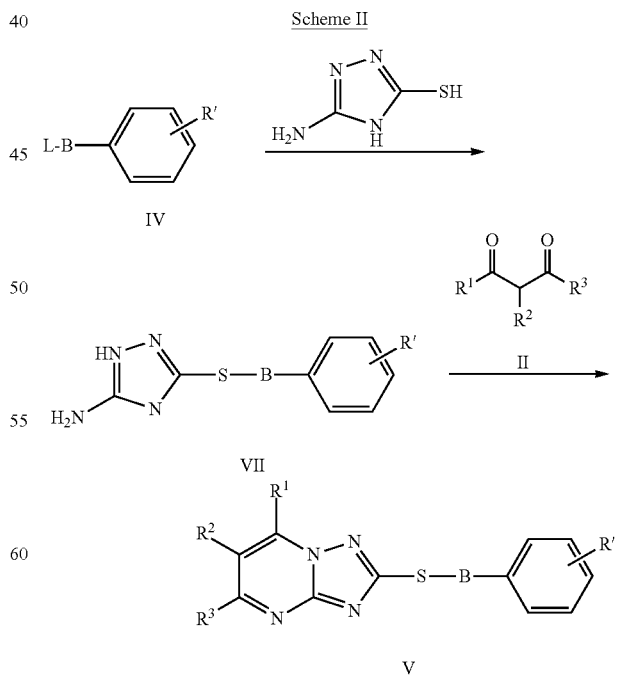

Alternatively, according to the reaction Scheme II, the order of reactions can be changed such that a reagent IV where L is a leaving group as defined in the Summary of the Invention can be reacted in the presence of a base such as potassium or sodium carbonate with the thiol of 3-amino-5-mercapto-1,2,4-triazole to obtain thioethers of the Formula VII. The substituted triazole VII can then be reacted in the presence of a complimentary reactive 1,3-dicarbonyl compound II under suitable reaction conditions for cyclo-condensation to obtain [1,2,4]triazolo[1,5-a]pyrimidine compounds of Formula V.

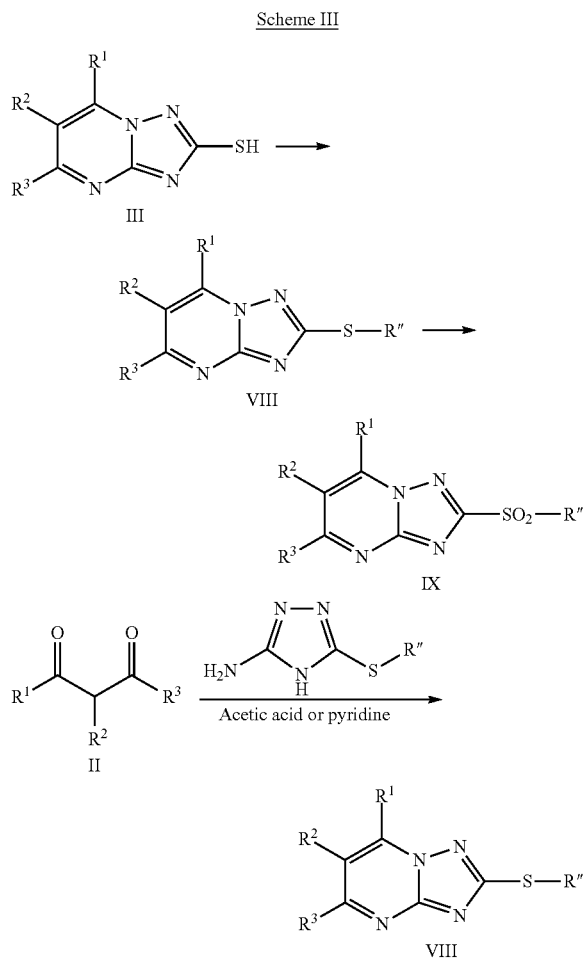

Compounds and/or compounds of formulas described herein (such as Formula I) where A is O or amino, preferably —NH— or —N(CH₃)—, can be prepared by nucleophilic aromatic substitution of an activated [1,2,4]triazolo[1,5-a] pyrimidine. Thiols of Formula III can be alkylated with an alkylating agent such as benzyl bromide or iodomethane, preferably iodomethane, in the presence of a base such as potassium carbonate to afford thioether of Formula VIII. Thioethers of Formula VIII can be oxidized in the presence of an oxidizing agent such as hydrogen peroxide, preferably 30-35% aqueous hydrogen peroxide, in the presence of a catalyst such as sodium tungstate and polar solvent such as acetic acid. A suitable reaction temperature is ambient temperature to 80° C., preferably 60° C. Alternatively, the substituted 1,3-dicarbonyl of Formula II can be reacted with a substituted 3-amino-5-mercapto-1,2,4-triazole in a solvent such as acetic acid or pyridine to obtain the thioether of Formula VIII according to the method described above.

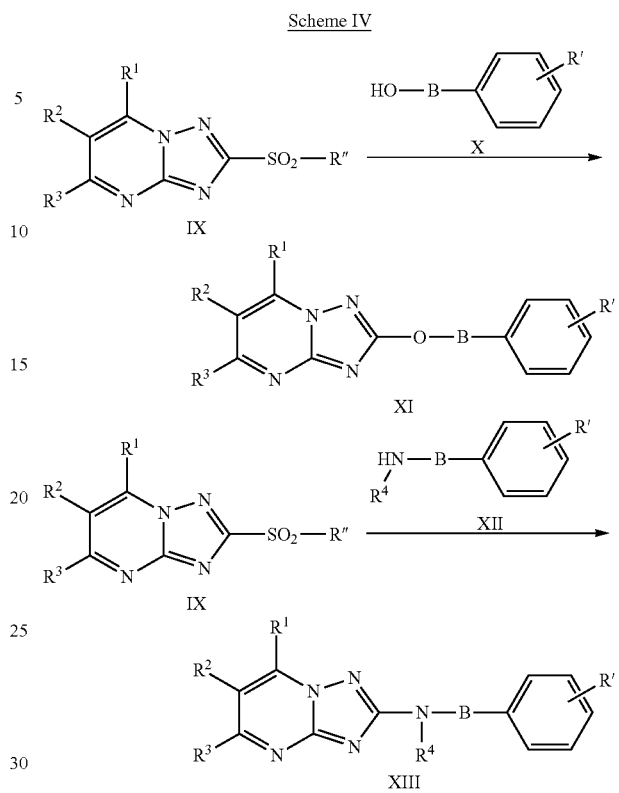

A sulfone compound of Formula IX can be reacted with a nucleophile that contains a reactive hydroxy or amino group, e.g., hydroxyalkylene, aminoalkylene or methylaminoalkylene for the group B-C, according to the following reaction Scheme IV. For example, reaction of a compound of Formula IX with hydroxy compound of formula X can provide an ether compound of formula XI. The reaction is carried out in the presence of a suitable base, such as sodium hydride, potassium tert-butoxide, sodium hydroxide, and the like, in the presence of a suitable reaction solvent, such as tetrahydrofuran, dioxane, N-methylpyrrolidinone, and the like, at a suitable temperature, preferably ambient temperature. Similarly, reaction of a compound of formula IX with amino compound of formula XII can provide an amino compound of formula of formula XIII. The reaction is carried out in a suitable reaction solvent, e.g., N,N-dimethylformamide, methyl sulfoxide, and the like, in the presence of a suitable base, e.g., potassium carbonate, sodium hydride, pyidine, and the like, or the reaction can be carried out without a solvent ("neat") and without a base when the free-base form of the amino compound of formula XII is used. A suitable temperature is 80° C. to 120° C., preferably 110° C. In intermediates of Formulas described herein (such as formula IX-XIII), R¹, R², R³, and R⁴ are as defined in the Summary of the invention.

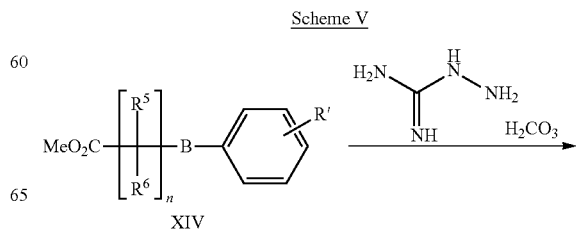

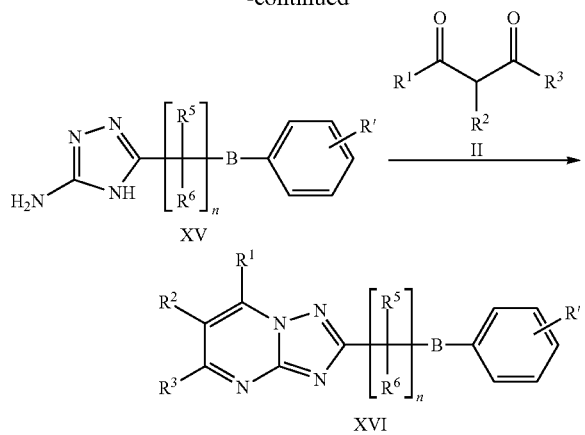

Compounds and/or compounds of formulas described herein (such as Formula I) where A is alkylene or bond can be prepared according to the reaction Scheme V. For example, cyclo-condensation of ester compounds of Formula XIV can be obtained by reacting with aminoguanidine bicarbonate in a suitable reaction solvent, such as water, methyl sulfoxide, and methanol, and the like, in the presence of a suitable base, such as sodium hydroxide and pyridine, at a suitable reaction temperature of 100° C. to 150° C. Preferably, the solvent is pyridine, and the base is pyridine, and the temperature is 125° C. An addition reaction of the compound of Formula XV can be carried out in the presence of complimentary reactive 1,3-dicarbonyl compounds, or their protected derivatives, such as 2,4-pentanedione, 3,5-heptanedione, 4,4-dimethoxy-2-butanone, and the like, under suitable reaction conditions for cyclo-condensation to provide 1,2,4-triazolo[1,5-a]pyrimidine compounds of Formula XVI. Each B, C, $R^1$, $R^2$, $R^3$, $R^5$, and $R^6$ is as defined in the Summary of the Invention, and $R^1$ is a ring system substituent as defined in the Summary of the Invention. A suitable reaction solvent is glacial acetic acid, and a suitable reaction temperature is at 100° C. to 150° C., preferably at the reflux temperature of glacial acetic acid.

V. Administration and Pharmaceutical Compositions

The treatment of diseases, such as anemia associated with chronic kidney disease, palliative chemotherapy of cancer, and Zidovudine-treatment of HIV infection, as described herein, is accomplished by increasing the levels of erythrocytes. The treatment of tissue- and organ injury or diseases of the central nervous system, such as Parkinson's disease, Alzheimer's disease, Huntington's disease, Friedreich's ataxia, and traumatic brain injury, and ischemic stroke, as described herein, is accomplished by protecting neurons from stress and death by toxins, ischemia, trauma, hemorrhage, oxidation, and genetic mutations.

In general, a compound of a formula described herein such as Formula (I) will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. For example, therapeutically effective amounts of a compound of Formula (I) may range from about 1 microgram per kilogram body weight (ug/kg) per day to about 100 milligram per kilogram body weight (mg/kg) per day, typically from about 10 mg/kg/day to about 100 mg/kg/day. Therefore, a therapeutically effective amount for an 80 kg human patient may range from about 0.1 mg/day to about 8 g/day, typically from about 1 mg/day to about 800 mg/day. In general, one of ordinary skill in the art, acting in reliance upon personal knowledge and the disclosure of this application, will be able to ascertain a therapeutically effective amount of a compound of Formula (I) for treating a given disease.

For intravenous formulations of the EPO mimetic of a formula described herein, the compound may be stored in the form of a solid (e.g., powder), optionally in combination with one or more other agents (e.g., donepezil, rivastigmine, galantamine, memantine, idebenone, levodopa, carbidopa, rasagiline, and biologicals such as erythropoietin, granulocyte-colony stimulating factor, granulocyte/macrophage-colony stimulating factor, tissue plasminogen activator), then reconstituted by the addition of a suitable liquid. Alternatively, the compound described herein may be stored as a solution or suspension (e.g., in a single use vial, a multiuse vial, or in a ready-to-use vial), optionally in combination with one or more other agents described herein. Alternatively, the solution or suspension of the compound described herein may be mixed, prior to administration, with the optional other agents, or the solution or suspension of the compound described herein may be administered separately from the solution or suspension of the other optional agents.

Oral formulations of the EPO mimetic described herein may be in the form of a pill or capsule. If combined with one or more agents (e.g., donepezil, rivastigmine, galantamine, memantine, idebenone, levodopa, carbidopa, and rasagiline), the compound described herein and the one or more agents may be mixed together with pharmaceutically acceptable excipients, or may be combined in a layered structure (e.g., bilayer pill) to segregate the various active ingredients. Alternatively, the compound described herein and the optional other agents may be administered separately.

Pharmaceutical compositions may contain from about 0.1 to about 99.9 weight percent, or from about 5 to about 95 weight percent, or from about 20 to about 80 weight percent of active ingredient (compound described herein). For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington: The Science and Practice of Pharmacy, $20^{th}$ Edition, (2000), Lippincott Williams & Wilkins, Baltimore, Md., herein incorporated by reference.

Liquid form preparations include solutions, suspensions and emulsions, for example, water or water-propylene glycol solutions for parenteral injection or addition of sweeteners and opacifiers for oral solutions, suspensions, and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably, the pharmaceutical preparation is in a unit dosage form. In such form, the preparations subdivided into suitably sized unit doses containing appropriate quantities of the active component, e.g., an effective amount to achieve the desired purpose.

For convenience, the total daily dosage may be divided and administered in portions during the day as required. The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.1 mg/day to about 2000 mg/day, in two to four divided doses.

The pharmaceutical compositions of the invention may be administered from about 1 to about 5 times per day, or alternatively, as a bolus injection or continuous infusion. Such administration can be used as a chronic or acute therapy.

The EPO mimetic can be administered in combination with further active ingredients known to treat anemia, including anemia associated with chronic kidney disease, palliative chemotherapy of cancer, Zidovudine-treatment of HIV infection, and surgeries requiring allogeneic blood transfusion. The term "further active ingredients" as used herein includes any compounds or therapeutic agents that can demonstrate advantageous properties when administered with EPO or an EPO mimetic. Examples of a further active ingredient or ingredients for use in combination with the compounds of this application include but are not limited to: erythropoietin, granulocyte-colony stimulating factor, and granulocyte/macrophage-colony stimulating factor.

The EPO mimetic can be administered in combination with further active ingredients known to treat organ injury or CNS diseases, including such as Parkinson's disease, Alzheimer's disease, multiple sclerosis, Huntington's disease, Friedreich's ataxia, traumatic brain injury, ischemic stroke, acute kidney injury, chronic kidney disease, and liver injury. The term "further active ingredients" as used herein includes any compounds or therapeutic agents that can demonstrate advantageous properties when administered with EPO or an EPO mimetic. Examples of a further active ingredient or ingredients for use in combination with the compounds of this application include but are not limited to: tissue plasminogen activator, donepezil, rivastigmine, galantamine, memantine, idebenone, levodopa, carbidopa, and rasagiline.

Further active ingredients as defined herein for treatment of anemia, as described in Macdougall, Clin. J. Am. Soc. Nephrology, (2008) 3:200, include: recombinant proteins (e.g., epoietin (alpha, beta, delta and omega), darbepoietin alpha, CERA, and AMG-531), fusion proteins (EPO-EPO, granulocyte/macrophage-colony stimulating factor-EPO, Fc-EPO, and CTNO 528), EPO mimetic peptides (e.g., Hematide), prolyl hydroxylase inhibitors (HIF stabilizers), and GATA inhibitors. Other non-limiting examples of such agents include hematopoietic growth factors (Deutsch et al., Br. J. Haematol. (2006), 134:453) such as thrombopoietin, erythropoietin, granulocyte-colony stimulating factor, granulocyte macrophage-colony stimulating factor, interleukin-1, interleukin-3, interleukin-6, interleukin-11, stem cell factor, FLT ligand, fibroblast growth factor, stromal-derived factor-1, GATA-1, nuclear factor erythroid-2, and AMG-531, or a biologically active derivative of the aforementioned agents. Preferably, the compound of Formula (I) and the pharmaceutically acceptable excipient is administered in combination with one or more compound(s) independently selected from erythropoietin, granulocyte-colony stimulating factor, and granulocyte/macrophage-colony stimulating factor.

The quantity of EPO mimetic in combination with a recombinant protein, e.g., erythropoietin, in a unit dose of preparation may be from about 10 to about 300 mg of EPO mimetic combined with from about 2,000 to 50,000 international units (IU) of erythropoietin. In another combination, the quantity of EPO mimetic in combination with erythropoietin in a unit dose of preparation may be from about 50 to about 300 mg of EPO mimetic combined with from about 10,000 to about 30,000 IU of erythropoietin.

The EPO mimetic can also be administered in combination with certain procedures such as dialysis and blood transfusion, which are well known treatments for chronic kidney disease.

Further active ingredients as defined herein for treatment of diseases of the CNS, as described in M. F. Beal's *Neurodegenerative Diseases: Neurobiology, Pathogenesis and Therapeutics*, Cambridge University Press, 2005, include: acetyl cholinesterase inhibitors (e.g., donepezil, rivastigmine, galantamine), glutamate receptor antagonists (e.g., memantine), antioxidants (e.g., idebenone), L-dopa mimetics (e.g., levodopa, and carbidopa), and MAO-B inhibitors (e.g., rasagiline).

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required. Upon improvement of a patient's condition, a maintenance dose of a compound, composition or combination of the invention may be administered, if necessary. Subsequently, the dosage or frequency of administration, or both, may be reduced, as a function of the symptoms, to a level at which the improved condition is retained. When the symptoms have been alleviated to the desired level, treatment should cease. Patients may, however, require intermittent treatment on a long-term basis upon any recurrence of disease symptoms.

Specific dosage and treatment regimens for any particular patient may be varied and will depend upon a variety of factors, including the activity of the specific compound employed, the age, body weight, general health status, sex and diet of the patient, the time of administration, the rate of excretion, the specific drug combination, the severity and course of the symptoms being treated, the patient's disposition to the condition being treated and the judgment of the treating physician.

Determination of the proper dosage regimen for a particular situation is within the skill of the art.

EXAMPLES

The invention disclosed herein is exemplified by the following preparations and examples, which should not be construed to limit the scope of the disclosure. Alternative mechanistic pathways and analogous structures may be apparent to those skilled in the art.

Example 1

2-{[2-(4-chlorophenoxy)ethyl]sulfanyl}-5,7-dimethyl-[1,2,4]triazolo[1,5-a]pyrimidine 5,7-Dimethyl-[1,2,4]-triazolo[1,5-a]pyrimidine-2-thiol

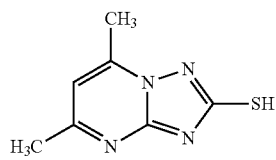

A mixture of 2,4-pentanedione (6.46 g, 64.6 mmol), 3-amino-5-mercapto-1,2,4-triazole (7.5 g, 64.6 mmol), glacial acetic acid (230 mL), and piperidine (0.58 mL, 5.9 mmol) was added to a 500 mL RBF with a magnetic stirring bar. The flask was fitted with a condenser, and warmed in an oil bath to a gentle reflux at 125° C. The mixture was heated for 45 hours, and solids remained visible in the flask throughout the heating period. Progress of the reaction was monitored by analytical HPLC with UV detection at 215 and 254 nm. The starting material 3-amino-5-mercapto-1,2,4-triazole elutes rapidly with retention time of 1.05 min, and the product elutes with retention time of 1.87 min. The mixture was cooled to room temperature. Solids were isolated by filtration, rinsed with 75 mL of acetic acid, and then dried under reduced pressure to afford the title compound as a pale yellow powder (9.5 g, 82% yield). A sample of 120 mg was recrystallized in warm acetic acid to afford 60 mg (50% recovery) of fine off-white needles, while the crude powder was used in the next step. $^1$H NMR (DMSO-$d_6$+CDCl$_3$, 400 MHz) δ ppm: 14.05 (br s, 1H), 7.25 (s, 1H), 2.67 (s, 3H), 2.56 (s, 3H). (NMR from crystalline material.)

2-{[2-(4-chlorophenoxy)ethyl]sulfanyl}-5,7-dimethyl-[1,2,4]triazolo[1,5-a]pyrimidine

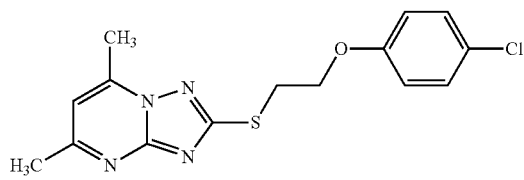

A mixture of 5,7-dimethyl-[1,2,4]-triazolo[1,5-a]pyrimidine-2-thiol (1.0 g, 5.6 mmol), 1-(2-bromoethoxy)-4-chlorobenzene (1.19 g, 5.1 mmol), potassium carbonate (1.75 g, 12.6 mmol), and anhydrous N,N-dimethylformamide (6 mL) was added to a 20 mL scintillation vial with a magnetic stirring bar. The vial was capped loosely and the mixture allowed to stir at room temperature for 30 minutes. Progress of the reaction was monitored by analytical HPLC with UV detection ($R_t$=8.28 min). The mixture contained solids starting at 30 minutes and was stopped stirring at 1 hour. The mixture was transferred into an Erlenmeyer flask with a total of 70 mL of water, and allowed to stir for 10 min. The resulting solid was isolated by filtration, rinsed with 100 mL of water, and allowed to dry under reduced pressure. The off-white powder was >90% pure by analytical HPLC with UV detection at 215 nm. The solid was dissolved in 25 mL of ethanol with gentle warming, diluted with 5 mL of water and allowed to cool. The fine white needles that formed were isolated by filtration, washed with 20 mL of cold ethanol, and dried to afford the title compound (1.43 g, 85% yield). EM (calc.): 334.1; MS (ESI) m/e: 335.1 (M+H)$^+$. $^1$H NMR (DMSO-$d_6$, 400 MHz) δ ppm: 7.31 (d, 2H), 7.12 (s, 1H), 7.03 (d, 2H), 4.33 (t, 2H), 3.60 (t, 2H), 2.68 (s, 3H), 2.55 (s, 3H).

Example 2

5,7-dimethyl-2-[(2-phenoxyethyl)sulfanyl]-[1,2,4]-triazolo[1,5-a]pyrimidine

The title compound was prepared according to the experimentals described for Example 1 above from 5,7-dimethyl-[1,2,4]-triazolo[1,5-a]pyrimidine-2-thiol and b-bromophenetole in 65% yield; EM (calc.): 300.1; MS (ESI) m/e: 301.1 (M+H)$^+$.

Example 3

2-{[2-(4-fluorophenoxy)ethyl]sulfanyl}-5,7-dimethyl-[1,2,4]triazolo[1,5-a]pyrimidine The title compound was prepared according to the experimentals described for Example 1 above from 5,7-dimethyl-[1,2,4]-triazolo[1,5-a]pyrimidine-2-thiol and 4-fluorophenoxy-ethylbromide in 57% yield; EM (calc.): 318.1; MS (ESI) m/e: 319.1 (M+H)$^+$. NMR (DMSO-$d_6$, 400 MHz) δ ppm: 7.11 (m, 3H), 7.00 (m, 2H), 4.31 (t, 2H), 3.59 (t, 2H), 2.67 (s, 3H), 2.55 (s, 3H).

Example 4

2-{[2-(4-chloro-3-fluorophenoxy)ethyl]sulfanyl}-5,7-dimethyl-[1,2,4]triazolo[1,5-a]pyrimidine 4-chloro-3-fluorophenoxy-ethylbromide

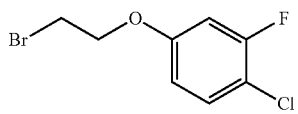 [SMILES: Fc1cc(OCCBr)ccc1Cl]

A mixture of 4-chloro-3-fluorophenol (0.30 g, 2.05 mmol), 1,2-dibromoethane (1.15 g, 6.14 mmol), sodium hydroxide (0.12 g, 3.07 mmol), and water (3 mL) was added to a 50 mL RBF with a magnetic stirring bar. The flask was fitted with a condenser and warmed to an oil bath temperature of 80° C. The progress of the reaction was monitored by analytical HPLC with UV detection at 215 nm. Another portion of 1,2-dibromoethane (1.09 g, 5.8 mmol) was added, and heating was continued for 24 h. The mixture was allowed to cool to ambient temperature, diluted with 20 mL of water, and extracted with 30 mL of ethyl acetate. The organic layer was washed with saturated aqueous sodium bicarbonate (2×10 mL), saturated aqueous sodium chloride (10 mL), dried (Na$_2$SO$_4$), filtered, and concentrated under reduced pressure. The crude material was purified by silical gel chromatography using a gradient elution of 0-100% ethyl acetate in hexanes. The title compound was obtained as a colorless oil (0.326 g, 63% yield). $^1$H NMR (DMSO-$d_6$, 400 MHz) δ ppm: 7.48 (t, 1H), 7.12 (dd, 1H), 6.86 (dd, 1H), 4.35 (t, 2H), 3.80 (t, 2H).

2-{[2-(4-chloro-3-fluorophenoxy)ethyl]sulfanyl}-5,7-dimethyl-[1,2,4]triazolo[1,5-a]pyrimidine The title compound was prepared according to the experimentals described for Example 1 above from 5,7-dimethyl-[1,2,4]triazolo[1,5-a]pyrimidine-2-thiol and 4-chloro-3-fluorophenoxy-ethylbromide in 75% yield; EM (calc.): 352.1; MS (ESI) m/e: 353.0 (M+H)$^+$.

Example 5

2-{[2-(3,4-dichlorophenoxy)ethyl]sulfanyl}-5,7-dimethyl-[1,2,4]-triazolo[1,5-a]pyrimidine The title compound was prepared according to the experimentals described for Example 1 above from 5,7-dimethyl-[1,2,4]triazolo[1,5-a]pyrimidine-2-thiol and 3,4-dichlorophenoxy-ethylbromide in 85% yield. The reagent 3,4-dichlorophenoxy-ethylbromide was prepared by a similar procedure for the synthesis of 4-chloro-3-fluorophenoxy-ethylbromide in Example 4 above from 3,4-dichlorophenol and 1,2-dibromoethane. EM (calc.): 368.0; MS (ESI) m/e: 369.0 (M+H)$^+$.

Example 6

2-{([2-(3-chloro-4-fluorophenoxy)ethyl]sulfanyl}-5,7-dimethyl-[1,2,4]-triazolo[1,5-a]pyrimidine The title compound was prepared according to the experimentals described for Example 1 above from 5,7-dimethyl-[1,2,4]triazolo[1,5-a]pyrimidine-2-thiol and 3-chloro-4-fluorophenoxy-ethylbromide in 81% yield. The reagent 3-chloro-4-fluorophenoxy-ethylbromide was prepared by a similar procedure for the synthesis of 4-chloro-3-fluorophenoxy-ethylbromide in Example 4 above from 3-chloro-4-fluorophenol and 1,2-dibromoethane. EM (calc.): 352.1; MS (ESI) m/e: 353.0 (M+H)$^+$.

Example 7

2-{[2-(3,4-difluorophenoxy)ethyl]sulfanyl}-5,7-dimethyl-[1,2,4]triazolo[1,5-a]pyrimidine The title compound was prepared according to the experimentals described for Example 1 above from 5,7-dimethyl-[1,2,4]triazolo[1,5-a]pyrimidine-2-thiol and 3,4-difluorophenoxy-ethylbromide in 36% yield. The reagent 3,4-difluorophenoxy-ethylbromide was prepared by a similar procedure for the synthesis of 4-chloro-3-fluorophenoxy-ethylbromide in Example 4 above from 3,4-difluorophenol and 1,2-dibromoethane. EM (calc.): 336.1; MS (ESI) m/e: 337.1 (M+H)$^+$.

Example 8

2-{[2-(4-ethylphenoxy)ethyl]sulfanyl}-5,7-dimethyl-[1,2,4]triazolo[1,5-a]pyrimidine The title compound was prepared according to the experimentals described for Example 1 above from 5,7-dimethyl-[1,2,4]triazolo[1,5-a]pyrimidine-2-thiol and 1-(2-bromoethoxy)-4-ethylbenzene in 51% yield. The reagent 1-(2-bromoethoxy)-4-ethylbenzene was prepared by a similar procedure for the synthesis of 4-chloro-3-fluorophenoxy-ethylbromide in Example 4 above from 4-ethylphenol and 1,2-dibromoethane. EM (calc.): 328.1; MS (ESI) m/e: 329.1 (M+H)$^+$.

Example 9

2-{[2-({5,7-Dimethyl-[1,2,4]triazolo[1,5-a]pyrimidin-2-yl}sulfanyl)ethyl](phenyl)amino}ethan-1-ol

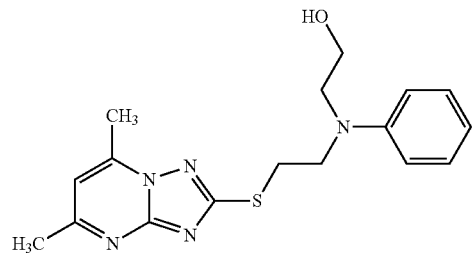 [SMILES: Cc1cc(C)n2nc(SCCN(CCO)c3ccccc3)nc2n1]

Under a nitrogen atmosphere, 5,7-dimethyl-[1,2,4]triazolo[1,5-a]pyrimidine-2-thiol (500 mg, 2.78 mmol), N-phenyldiethanolamine (458 mg, 2.53 mmol), tetrahydrofuran (5 mL) and a magnetic stirring bar were added to a 50 mL RBF. Triphenylphosphine (861 mg, 3.28 mmol) was added followed by the slow addition of diisopropylazodicarboxylate (664 mg, 3.28 mmol) via syringe over 15 minutes. The mixture was stirred at room temperature for 2 h. Progress of the reaction was monitored by HPLC. The reaction was concentrated then ethyl acetate (40 mL) was added which caused a precipitate to form. The precipitate was removed by filtration and rinsed with ethyl acetate (4 mL). The organic layer was concentrated. The title compound was purified by silica gel column chromatography with a gradient elution of 65-100% ethyl acetate in hexanes. Fractions were combined and concentrated under reduced pressure. The resulting solid was triturated with ethyl acetate (3 mL) and dried to afford the title compound as a white solid (274 mg, 32% yield). $^1$H NMR (DMSO-$d_6$, 400 MHz) δ ppm: 7.16 (m, 3H), 6.90 (d, 2H), 6.59 (t, 1H), 4.71 (t, 1H), 3.73 (m, 2H), 3.56 (q, 2H), 3.46 (t, 2H), 3.35 (m, 2H), 2.74 (s, 3H), 2.56 (s, 3H). EM (calc.): 343.1; MS (ESI) m/e: 344.2 (M+H)$^+$.

Example 10

2-({5,7-dimethyl-[1,2,4]triazolo[1,5-a]pyrimidin-2-yl}sulfanyl)-N-(4-methoxyphenyl)acetamide 2-({5,7-dimethyl-[1,2,4]triazolo[1,5-a]pyrimidin-2-yl}sulfanyl)acetic acid

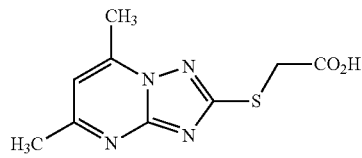

A mixture of 5,7-Dimethyl-[1,2,4]triazolo[1,5-a]pyrimidine-2-thiol (1.0 g, 5.6 mmol), sodium hydroxide (0.44 g, 11.1 mmol), and water (22 mL) was added to a 100 mL RBF with a magnetic stirring bar. The flask was fitted with a condenser, and the mixture was warmed to reflux in a 120° C. oil bath for 30 min. The mixture was removed from the oil bath and allowed to cool, and chloroacetic acid (0.525 g, 5.6 mmol) was added. Warming to reflux was continued for 6 h. The mixture was allowed to cool to ambient temperature, and the pH was adjusted to 2 with 1 M aqueous hydrochloric acid (5 mL). A solid precipitate was isolated by filtration, rinsed with 1 M hydrochloric acid (2 mL) and water (5 mL), and allowed to dry. The title compound was obtained as a tan solid (1.16 g, 88% yield). $^1$H NMR (DMSO-$d_6$, 400 MHz) δ ppm: 12.85 (br s, 1H), 7.12 (s, 1H), 4.08 (s, 2H), 2.66 (s, 3H), 2.54 (s, 3H).

2-({5,7-dimethyl-[1,2,4]triazolo[1,5-a]pyrimidin-2-yl}-sulfanyl)-N-(4-methoxyphenyl)acetamide

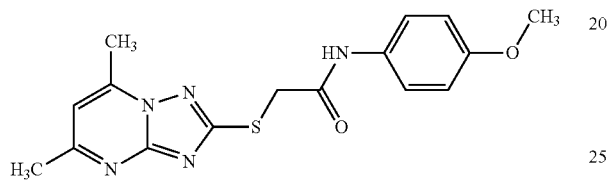

A mixture of 2-({5,7-dimethyl-[1,2,4]triazolo[1,5-a]pyrimidin-2-yl}sulfanyl)acetic acid (0.10 g, 0.42 mmol), p-anisidine (52 mg, 0.42 mmol), N,N-dicyclohexylcarbodiimide (87 mg, 0.42 mmol), and N,N-dimethylformamide (2 mL) was added to a 20 mL scintillation vial with a magnetic stirring bar. The mixture was allowed to stir at ambient temperature for 36 h. A white precipitate was removed by filtration and rinsed with N,N-dimethylformamide (0.5 mL) followed by water (1 mL). A precipitate formed in the liquid layer upon standing at ambient temperature for 12 h and was isolated by filtration. The crude precipitate was crystallized from warn ethanol (12 mL). The crystallized material was isolated by filtration, rinsed with ethanol, and allowed to dry. The title compound was obtained as an off-white solid (144 mg, 38% yield). $^1$H NMR (DMSO-$d_6$, 400 MHz) δ ppm: 10.21 (s, 1H), 7.49 (d, 2H), 7.11 (s, 1H), 6.88 (d, 2H), 4.19 (s, 2H), 3.71 (s, 3H), 2.66 (s, 3H), 2.54 (s, 3H).

Example 11

2-[2-(4-chlorophenoxy)ethoxy]-5,7-dimethyl-[1,2,4]triazolo[1,5-a]pyrimidine 5,7-Dimethyl-2-(methylsulfanyl)-[1,2,4]-triazolo[1,5-a]pyrimidine

A mixture of 2,4-pentanedione (11.54 g, 115 mmol), 3-amino-5-methylthio-1H-1,2,4-triazole (15.0 g, 115 mmol), and glacial acetic acid (115 mL) was added to a 1 L RBF with a magnetic stirring bar. The flask was fitted with a condenser, and warmed in an oil bath to a gentle reflux at 135° C. The mixture was heated for 15 hours. Progress of the reaction was monitored by analytical HPLC with UV detection at 215 and 254 nm. The starting material 3-amino-5-methylthio-1H-1,2,4-triazole elutes rapidly with retention time of 0.7 min, and the product elutes with retention time of 5.0 min. The mixture was cooled to room temperature, then slowly poured into stirring ice/water (750 mL) to precipitate product and stirred ~20 minutes. Solids were isolated by filtration, rinsed with 250 mL of water, and then dried under reduced pressure to afford the title compound as a powder (15.9 g, 71% yield).

2-Methanesulfonyl-5,7-dimethyl-[1,2,4]triazolo[1,5-a]pyrimidine

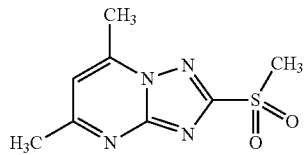

A mixture of 5,7-dimethyl-2-(methylsulfanyl)-[1,2,4]triazolo[1,5-a]pyrimidine (9.9 g, 51.0 mmol), sodium tungstate dihydrate (505 mg, 1.53 mmol), and glacial acetic acid (95 mL) was added to a 200 mL RBF with a magnetic stirring bar. The flask was cooled to =10° C. using ice and water bath. A solution of 35% hydrogen peroxide in water (13.1 mL, 153.1 mmol) was slowly added via syringe. The mixture was stirred at room temperature for 10 minutes, then at 60° C. for 60 minutes. Progress of the reaction was monitored by analytical HPLC with UV detection at 215 nm. The starting material elutes with retention time of 3.8 min, and the product elutes with retention time of 1.3 min. The reaction was cooled to room temperature and a solution of sodium sulfite (3.0 g $Na_2SO_3$ in 20 mL water) (=5 mL) was added to the mixture until negative to peroxide test strip, and allowed to stir 30 minutes at room temperature. The reaction was concentrated to ~20 mL and water was added to precipitate product. The solid was collected by filtration, rinsed with cold water (=30 mL) and dried under vacuum to afford the title compound as a white powder (7.78 g, 67% yield).

2-(4-Chlorophenoxy)ethan-1-ol

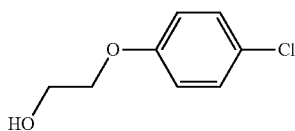 [SMILES: OCCOc1ccc(Cl)cc1]

A mixture of 4-chlorophenol (5.61 g, 43.65 mmol), 2-bromoethanol (6.0 g, 48.0 mmol), sodium hydroxide (2.62 g, 65.47 mmol), and water (18 mL) was added to a 50 mL RBF with a magnetic stirring bar. The flask was fitted with a condenser, and warmed in an oil bath at 80° C. The solution was heated for 19 hours. Progress of the reaction was monitored by analytical HPLC with UV detection. The reaction mixture was partitioned using ethyl acetate (100 mL) and water (50 mL). The aqueous layer was extracted once more with ethyl acetate (40 mL). The combined organic layer was washed with 1N NaOH (6×40 mL) and saturated aqueous NaCl (40 mL), dried ($Na_2SO_4$), filtered, and concentrated. The crude mixture was purified by silica gel column chromatography using 30-100% ethyl acetate in hexanes to afford the title compound as a clear oil (5.67 g, 75% yield).

2-[2-(4-Chlorophenoxy)ethoxy]-5,7-dimethyl-[1,2,4]-triazolo[1,5-a]pyrimidine

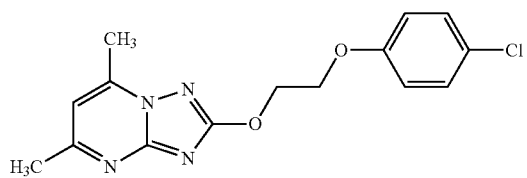 [SMILES: Cc1cc(C)n2nc(OCCOc3ccc(Cl)cc3)nc2n1]

A mixture of 2-(4-chlorophenoxy)ethan-1-ol (4.0 g, 23.19 mmol) and tetrahydrofuran (40 mL) was added to a 200 mL RBF under a nitrogen atmosphere with a magnetic stirring bar. Sodium hydride (60% dispersion in mineral oil) (1.26 g, 31.62 mmol) was added portion-wise (4×~315 mg) over 10 minutes (Effervescence). The reaction was stirred for 10 minutes before 2-methanesulfonyl-5,7-dimethyl-[1,2,4]triazolo[1,5-a]pyrimidine (4.76 g, 21.08 mmol) was added portion-wise (5×~0.95 g) (Effervescence). Progress of the reaction was monitored by analytical HPLC with UV detection at 215 nm. 2-Methanesulfonyl-5,7-dimethyl-[1,2,4]triazolo[1,5-a]pyrimidine elutes with retention time of 1.3 min, 2-(4-chlorophenoxy)ethan-1-ol elutes with retention time of 4.5 min, and the title compound elutes with retention time of 5.7 min. A precipitate is visible after 5 minutes of reaction. An additional portion of tetrahydrofuran (10 mL) was added to aid stirring. After 30 minutes the reaction was concentrated and then partitioned between dichloromethane (100 mL) and water (50 mL). The aqueous layer was extracted once more with dichloromethane (100 mL), and the combined organic layer was dried (Na$_2$SO$_4$), filtered, and concentrated. To a mixture of the crude material in 1% methanol in dichloromethane (60 mL), silica gel (10 g) was added, and the mixture swirled for 10 minutes. The silica gel was removed by filtration, rinsed with dichloromethane (100 mL), and the organic solvent was concentrated under reduced pressure. The solid was dissolved in warm ethanol (125 mL) and water (13 mL), and allowed to cool overnight. Crystalline material was isolated by filtration, rinsed with ethanol:water (10:1) (110 mL) and allowed to dry. A light pink color remained. The solid was then dissolved in 2% methanol in dichloromethane (30 mL), and to this mixture, silica gel (5 g) was added and swirled for 20 minutes. The silica gel was removed by filtration through a plug of fresh silica gel (2 g), rinsed with 2% methanol in dichloromethane (50 mL), and the organic solvent was concentrated under reduced pressure. The solid was dissolved in warm ethanol (95 mL) and allowed to cool overnight. An off-white crystalline material was isolated by filtration, rinsed with ethanol (75 mL), and dried to afford the title compound as an off white solid (4.22 g, 62% yield). $^1$H NMR (DMSO-d$_6$, 400 MHz) δ ppm: 7.34 (d, 2H), 7.09 (s, 1H), 7.02 (d, 2H), 4.67 (t, 2H), 4.36 (t, 2H), 2.63 (s, 3H), 2.52 (s, 3H). EM (calc.): 318.1; MS (ESI) m/e: 319.2 (M+H)$^+$.

Example 12

2-(3-cyclopentylpropoxy)-5,7-dimethyl-[1,2,4]-triazolo[1,5-a]pyrimidine

The title compound was prepared according to the experimentals described for Example 11 above from 2-methanesulfonyl-5,7-dimethyl-[1,2,4]triazolo[1,5-a]pyrimidine and 3-cyclopentyl-1-propanol in 52% yield. EM (calc.): 274.2; MS (ESI) m/e: 275.3 (M+H)$^+$.

Example 13

2-{[2-({5,7-Dimethyl-[1,2,4]triazolo[1,5-a]pyrimidin-2-yl}oxy)ethyl](phenyl)amino}ethan-1-ol

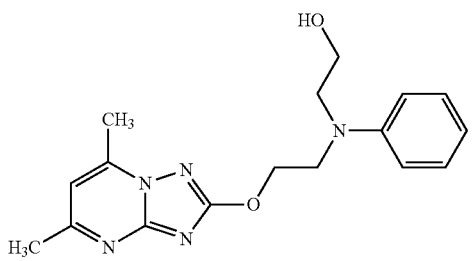 [SMILES: Cc1cc(C)n2nc(OCCN(CCO)c3ccccc3)nc2n1]

A mixture of N-phenyldiethanolamine (8.76 g, 48.3 mmol) and tetrahydrofuran (70 mL) was added to a 200 mL RBF under a nitrogen atmosphere with a magnetic stirring bar. Sodium hydride (60% dispersion in mineral oil) (1.93 g, 48.3 mmol) was added portion-wise (4×~500 mg) over 10 minutes (Effervescence). The reaction was stirred for 10 minutes before 2-methanesulfonyl-5,7-dimethyl-[1,2,4]-triazolo[1,5-a]pyrimidine (9.1 g, 40.3 mmol) was added portion-wise (4×~2.3 g) over 10 minutes (Effervescence). Progress of the reaction was monitored by analytical HPLC with UV detection at 215 nm. The title compound eluted with retention time of 3.7 min. After 45 minutes the reaction was concentrated under reduced pressure then partitioned between dichloromethane (200 mL) and water (25 mL). The aqueous layer was extracted once more with dichloromethane (100 mL). The combined organic layer was washed with saturated aqueous NaCl (25 mL), dried (Na$_2$SO$_4$), filtered, and concentrated. The crude material was dissolved in ethyl acetate (80 mL) and extracted with 1 N HCl (80 mL) and 0.5 N HCl (10 mL). Solid NaCl was added (~1-3 g) to the combined acidic extracts with stirring for 10 minutes. The pH was adjusted to basic with 5 N NaOH (~23 mL) and a gummy precipitate formed. The aqueous layer was decanted into a separatory funnel, and the solid residue was rinsed with an additional 15 mL of water. The combined aqueous layers were extracted with dichloromethane (4×30 mL). The gummy precipitate was dissolved in an additional amount of dichloromethane (50 mL), and the combined organic layers were dried (Na$_2$SO$_4$), filtered, and concentrated under reduced pressure. The crude material was purified by silica gel column chromatography using a gradient elution of 60-100% ethyl acetate in hexanes to afford the title compound as a white solid (8.62 g, 65% yield). $^1$H NMR (DMSO-d$_6$, 400 MHz) δ ppm: 7.15 (m, 2H), 7.07 (s, 1H), 6.79 (d, 2H), 6.59 (t, 1H), 4.70 (t, 1H), 4.49 (t, 2H), 3.79 (t, 2H), 3.54 (q, 2H), 3.46 (m, 2H), 2.63 (s, 3H), 2.52 (s, 3H). EM (calc.): 327.2; MS (ESI) m/e: 328.2 (M+H)$^+$.

Example 14

2-{[2-({5,7-diethyl-[1,2,4]triazolo[1,5-a]pyrimidin-2-yl}oxy)ethyl](4-fluorophenyl)amino}ethan-1-ol

5,7-Diethyl-2-(methylsulfanyl)-[1,2,4]triazolo[1,5-a]pyrimidine

A mixture of 3,5-heptanedione (9.85 g, 76.8 mmol), 3-amino-5-methylthio-1H-1,2,4-triazole (10.0 g, 76.8 mmol), and glacial acetic acid (60 mL) was added to a 200 mL RBF with a magnetic stirring bar. The flask was fitted with a condenser, and warmed in an oil bath to a gentle reflux at 135° C. The mixture was heated for 24 hours. Progress of the reaction was monitored by analytical HPLC with UV detection at 215 and 254 nm. The starting material 3-amino-5-methylthio-1H-1,2,4-triazole eluted rapidly with retention time of 0.7 min, and the product eluted with retention time of 4.7 min. The mixture was cooled to room temperature, then slowly poured into stirring ice/water (800 mL) to precipitate product and stirred ~20 minutes. Solids were isolated by filtration, rinsed with water (200 mL), and then dried under reduced pressure to afford the title compound as a powder (15.0 g, 88% yield).

2-Methanesulfonyl-5,7-diethyl-[1,2,4]triazolo[1,5-a]pyrimidine

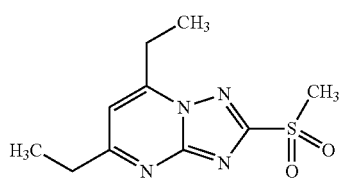 [SMILES: CCc1cc(CC)n2nc(S(C)(=O)=O)nc2n1]

A mixture of 5,7-diethyl-2-(methylsulfanyl)-[1,2,4]triazolo[1,5-a]pyrimidine (11.0 g, 49.5 mmol), sodium tungstate dihydrate (490 mg, 1.49 mmol), and glacial acetic acid (90 mL) was added to a 1 L RBF with a magnetic stirring bar. The flask was cooled to ~10° C. using ice and water bath. A solution of 35% Hydrogen peroxide in water (12.7 mL, 148.6 mmol) was slowly added drop-wise. The mixture was stirred at room temperature for 10 minutes, then at 60° C. for 40 minutes. Progress of the reaction was monitored by analytical HPLC with UV detection at 215 nm. The starting material eluted with retention time of 4.7 min, and the product eluted with retention time of 3.8 min. The reaction was cooled to room temperature and a solution of sodium sulfite (3.0 g Na$_2$SO$_3$ in 20 mL water) (~4 mL) was added to the mixture until negative to peroxide test strip, and allowed to stir at room temperature overnight. The reaction was concentrated to ~15 mL and partitioned using ethyl acetate (300 mL) and water (30 mL). The aqueous layer was extracted with ethyl acetate (2×75 mL). The combined organic layers were washed with saturated aqueous NaCl (30 mL), dried (Na$_2$SO$_4$), filtered, and concentrated to afford the title compound as a white powder (12.2 g, 97% yield).

2-[(4-Fluorophenyl)(2-hydroxyethyl)amino]ethan-1-ol

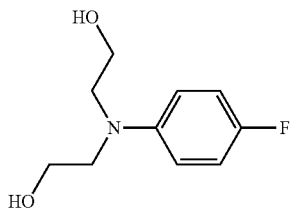 [SMILES: OCCN(CCO)c1ccc(F)cc1]

A mixture of 4-fluoroaniline (1.0 g, 9.0 mmol), 2-chloroethanol (2.9 g, 36.0 mmol), calcium carbonate (1.85 g, 18.4 mmol), and water (46 mL) was added to a 100 mL RBF with a magnetic stirring bar, and the flask was fitted with a condenser. The mixture was allowed to stir at an oil bath temperature of 115° C. for 22 hours. Progress of the reaction was monitored by TLC using ethyl acetate:hexanes (1:1) (R$_f$ starting material=0.6, R$_f$ product=0.2). To the reaction was added another aliquot of 2-chloroethanol (1.45 g, 18.0 mmol) and calcium carbonate (0.92 g, 9.2 mmol), and heating was continued for another 4 hours. The reaction was allowed to cool to ambient temperature and extracted with ethyl acetate (4×50 mL). The combined organic layers were washed with saturated aqueous NaCl (2×30 mL), dried (Na$_2$SO$_4$), filtered and concentrated under reduced pressure. The crude material was purified by silica gel column chromatography using a gradient elution of 35-100% ethyl acetate in hexanes to afford the title compound as an oil that slowly crystallized upon standing (1.67 g, 94% yield).

2-{[2-({5,7-Diethyl-[1,2,4]triazolo[1,5-a]pyrimidin-2-yl}oxy)ethyl](4-fluorophenyl)amino}ethan-1-ol

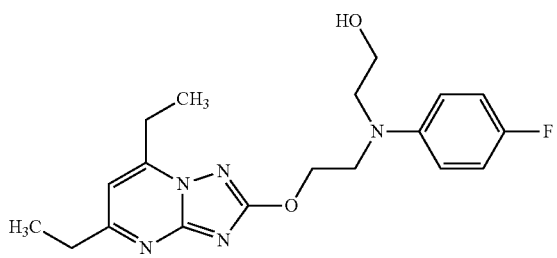

A mixture of 2-[(4-fluorophenyl)(2-hydroxyethyl)amino]ethan-1-ol (200 mg, 1.01 mmol) and tetrahydrofuran (5 mL) was added to a 50 mL RBF under a nitrogen atmosphere with a magnetic stirring bar. The flask was cooled in an ice bath. Sodium hydride (60% dispersion in mineral oil) (40 mg, 1.01 mmol) was added (Effervescence). The reaction was warmed to room temperature and stirred for 10 minutes before 2-methanesulfonyl-5,7-diethyl-[1,2,4]-triazolo[1,5-a]pyrimidine (213 mg, 0.84 mmol) was added (Effervescence). Progress of the reaction was monitored by analytical HPLC with UV detection at 215 nm. The title compound eluted with a retention time of 4.1 min. After 90 minutes the reaction was concentrated then partitioned between dichloromethane (30 mL) and water (5 mL). The aqueous layer was extracted once more with dichloromethane (20 mL). The combined organic layers were dried (Na$_2$SO$_4$), filtered and concentrated. The title crude material was purified by silica gel column chromatography using a gradient elution of 1-10% isopropanol in dichloromethane to afford the title compound as an oil that crystallized upon standing overnight (135 mg, 43% yield). $^1$H NMR (DMSO-d$_6$, 400 MHz) δ ppm: 7.09 (s, 1H), 6.99 (t, 2H), 6.78 (m, 2H), 4.69 (t, 1H), 4.48 (t, 2H), 3.77 (t, 2H), 3.53 (q, 2H), 3.43 (t, 2H), 3.01 (q, 2H), 2.82 (q, 2H), 1.32 (t, 3H), 1.26 (t, 3H). EM (calc.): 373.2; MS (ESI) m/e: 374.3 (M+H)$^+$.

Example 15

5,7-diethyl-2-[2-(4-fluorophenoxy)ethoxy]-[1,2,4]triazolo[1,5-a]pyrimidine

The title compound was prepared according to the experimentals described for Example 14 above from 2-methanesulfonyl-5,7-diethyl-[1,2,4]triazolo[1,5-a]pyrimidine and 2-(4-fluorophenoxy)ethan-1-ol in 70% yield. EM (calc.): 330.1; MS (ESI) m/e: 331.3 (M+H)$^+$.

Example 16

5,7-diethyl-2-[-2-(4-chlorophenoxy)ethoxy]-[1,2,4]triazolo[1,5-a]pyrimidine

The title compound was prepared according to the experimentals described for Example 14 above from 2-methanesulfonyl-5,7-diethyl-[1,2,4]triazolo[1,5-a]pyrimidine and 2-(4-chlorophenoxy)ethan-1-ol in 80% yield. EM (calc.): 346.1; MS (ESI) m/e: 347.3 (M+H)$^+$.

Example 17

2-{[2-({5,7-Diethyl-[1,2,4]triazolo[1,5-a]pyrimidin-2-yl}oxy)ethyl](phenyl)amino}ethan-1-ol The title compound was prepared according to the experimentals described for Example 14 above from 2-methanesulfonyl-5,7-diethyl-[1,2,4]-triazolo[1,5-a]pyrimidine and N-phenyldiethanolamine in 43% yield. EM (calc.): 355.2; MS (ESI) m/e: 356.3 (M+H)$^+$.

Example 18

5,7-diethyl-N-(2-phenoxyethyl)-[1,2,4]triazolo[1,5-a]pyrimidin-2-amine

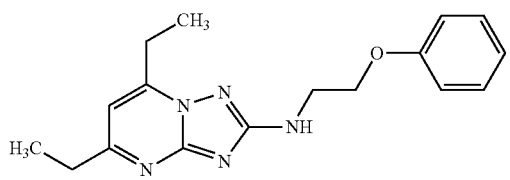 [SMILES: CCc1cc(CC)n2nc(NCCOc3ccccc3)nc2n1]

A mixture of 2-methanesulfonyl-5,7-diethyl-[1,2,4]-triazolo[1,5-a]pyrimidine (4.5 g, 17.7 mmol) and 2-phenoxyethylamine (24.3 g, 177.2 mmol) was added to a 100 mL RBF with a magnetic stirring bar, and the flask was fitted with a condenser. The mixture was allowed to stir at 110-120° C. for 72 hours. Progress of the reaction was monitored by analytical HPLC with UV detection where the title compound eluted with retention time of 5.1 min. The reaction was allowed to cool to room temperature and partitioned between dichloromethane (150 mL) and 2 N HCl (100 mL). The acidic layer was extracted with dichloromethane (100 mL), and the combined organic layers were washed with saturated aqueous NaCl (75 mL). The NaCl layer was extracted with dichloromethane (75 mL), and the combined organic layers were dried (Na$_2$SO$_4$), filtered, and concentrated under reduced pressure. The crude material was added to chloroform (25 mL) and methanol (0.5 mL), and a precipitate was removed by filtration. The material in the organic layer was purified by silica gel chromatography with a gradient elution of 0.75-3.0% ethanol in chloroform. Fractions were pooled and concentrated under reduced pressure, and the solid material was crystallized from hot ethanol (35 mL) to afford the title compound as an off white solid (3.26 g, 59% yield). $^1$H NMR (DMSO-d$_6$, 400 MHz) δ ppm: 7.27 (m, 2H), 7.03 (t, 1H), 6.96 (m, 3H), 6.85 (s, 1H), 4.13 (t, 2H), 3.61 (q, 2H), 2.96 (q, 2H), 2.75 (q, 2H), 1.31 (t, 3H), 1.24 (t, 3H). EM (calc.): 311.2; MS (ESI) m/e: 312.3 (M+H)$^+$.

Example 19

N-[2-(4-chlorophenoxy)ethyl]-5,7-dimethyl-[1,2,4]triazolo[1,5-a]pyrimidin-2-amine The title compound was prepared according to the experimentals described for Example 18 above from 2-methanesulfonyl-5,7-dimethyl-[1,2,4]-triazolo[1,5-a]pyrimidine and 2-(4-chlorophenoxy)ethylamine in 26% yield; EM (calc.): 317.1; MS (ESI) m/e: 318.2 (M+H)$^+$. $^1$H NMR (DMSO-d$_6$, 400 MHz) δ ppm: 7.31 (dt, 2H), 7.03 (d, 1H), 6.98 (dt, 2H), 6.85 (s, 1H), 4.13 (t, 2H), 3.60 (q, 2H), 2.57 (s, 3H), 2.45 (s, 3H).

Example 20

2-[(3-{5,7-diethyl-[1,2,4]triazolo[1,5-a]pyrimidin-2-yl}propyl)(4-fluorophenyl)amino]ethan-1-ol 2-[(4-Fluorophenyl)amino]ethan-1-ol

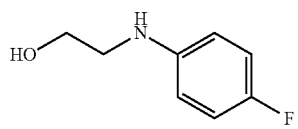 [SMILES: OCCNc1ccc(F)cc1]

A mixture of 4-fluoroaniline (1.0 g, 8.99 mmol), 2-bromoethanol (2.25 g, 17.99 mmol), potassium carbonate (2.49 g, 17.99 mmol), and anhydrous N,N-dimethylformamide (4 mL) was added to a 50 mL RBF with a magnetic stirring bar. The mixture was allowed to stir at 80° C. for 18 hours. Progress of the reaction was monitored by TLC using ethyl acetate:hexanes (1:1) (R$_f$ product=0.4). The reaction was partitioned using ethyl acetate (80 mL) and water (30 mL). The organic layer was washed with saturated aqueous NaCl (3×30 mL), dried (Na$_2$SO$_4$), filtered, and concentrated. The crude material was purified by silica gel column chromatography using a gradient elution of 30-100% ethyl acetate in hexanes to afford the title compound as an oil (0.75 g, 54% yield).

Methyl 4-[(4-fluorophenyl)(2-hydroxyethyl)amino]butanoate

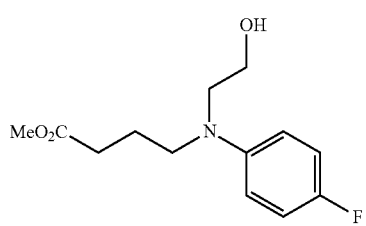 [SMILES: COC(=O)CCCN(CCO)c1ccc(F)cc1]

A mixture of 2-[(4-fluorophenyl)amino]ethan-1-ol (1.3 g, 8.39 mmol), methyl 4-bromobutyrate (2.28 g, 12.58 mmol), potassium carbonate (2.31 g, 16.77 mmol), and anhydrous N,N-dimethylformamide (6 mL) was added to a 50 mL RBF with a magnetic stirring bar. The mixture was allowed to stir at 80° C. for 16 hours. Progress of the reaction was monitored by TLC using ethyl acetate:hexanes (1:1) ($R_f$ product=0.5). Another aliquot of methyl 4-bromobutyrate (0.76 g, 4.20 mmol) was added and this was allowed to stir at 80° C. for 20 hours, until 2-[(4-fluorophenyl)amino]ethan-1-ol was consumed by TLC analysis. The reaction was partitioned using ethyl acetate (50 mL) and water (15 mL). The aqueous layer was extracted with ethyl acetate (20 mL). The combined organic layer was washed with saturated aqueous NaCl (3×10 mL), dried (Na$_2$SO$_4$), filtered and concentrated under reduced pressure. The crude material was purified by silica gel column chromatography using a gradient elution of 20-100% ethyl acetate in hexanes to afford the title compound as an oil (1.1 g, 52% yield).

2-{[3-(5-Amino-1H-1,2,4-triazol-3-yl)propyl](4-fluorophenyl)amino}ethan-1-ol

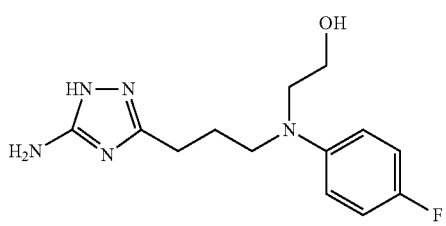 [SMILES: Nc1nc(CCCN(CCO)c2ccc(F)cc2)n[nH]1]

A mixture of methyl 4-[(4-fluorophenyl)(2-hydroxyethyl) amino]butanoate (1.1 g, 4.31 mmol), aminoguanidine bicarbonate (1.47 g, 10.78 mmol), and pyridine (12 mL) was added to a 200 mL RBF with a magnetic stirring bar. The flask was fitted with a condenser and heated to 125° C. using an oil bath. Progress of the reaction was monitored by TLC using chloroform:methanol: acetic acid (9:1:0.2) ($R_f$ starting material=0.8, $R_f$ product=0.1). During the course of heating, additional portions of aminoguanidine bicarbonate were added at 15 h and 22 h (2×1.0 g, 14.7 mmol total). After 37 hours of heating, the reaction was complete by TLC analysis and was allowed to cool to ambient temperature. The mixture was concentrated under reduced pressure and partitioned between ethyl acetate (60 mL) and water (30 mL). The aqueous layer was extracted with ethyl acetate (2×50 mL). The combined organic layers were washed with saturated aqueous NaCl (10 mL), dried (Na$_2$SO$_4$), filtered and concentrated. The crude material was purified by silica gel column chromatography using 100% ethyl acetate, followed by 10% methanol in dichloromethane to afford the title compound as an oil (0.55 g, 45% yield).

2-[(3-{5,7-Diethyl-[1,2,4]-triazolo[1,5-a]pyrimidin-2-yl}propyl)(4-fluorophenyl)amino]ethan-1-ol

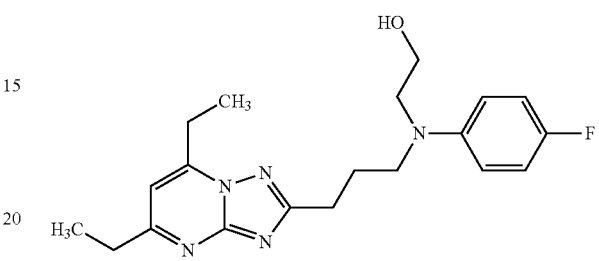

A mixture of 3,5-heptanedione (216 mg, 1.68 mmol), 2-{[3-(5-amino-1H-1,2,4-triazol-3-yl)propyl](4-fluorophenyl) amino}ethan-1-ol (470 mg, 1.68 mmol), and pyridine (3 mL) was added to a 50 mL RBF with a magnetic stirring bar. The flask was fitted with a condenser, and warmed in an oil bath to a gentle reflux at 125° C. Progress of the reaction was monitored by TLC using chloroform:methanol:acetic acid (9:1:0.2) ($R_f$ starting material=0.1, $R_f$ product=0.7). The solution was heated for 17 hours, and an additional portion of 3,5-heptanedione (95 mg, 0.74 mmol) was added. After an additional 6 hours of heating, the reaction was complete by TLC disappearance of the starting material. The mixture was allowed to cool to room temperature, concentrated under reduced pressure, and the crude material was purified by silica gel column chromatography using a gradient elution of 65-100% ethyl acetate in hexanes to afford the title compound as an oil (450 mg, 72% yield). $^1$H NMR (DMSO-d$_6$, 400 MHz) δ ppm: 7.11 (s, 1H), 6.95 (m, 2H), 6.70 (m, 2H), 4.66 (t, 1H), 3.50 (q, 2H), 3.40 (t, 2H), 3.35 (m, 2H), 3.09 (q, 2H), 2.86 (q, 4H), 1.99 (m, 2H), 1.34 (t, 3H), 1.28 (t, 3H). EM (calc.): 371.2; MS (ESI) m/e: 372.3 (M+H)$^+$.

Example 21

2-[(3-{5,7-diethyl-[1,2,4]triazolo[1,5-a]pyrimidin-2-yl}propyl)(4-fluorophenyl)amino]ethyl acetate

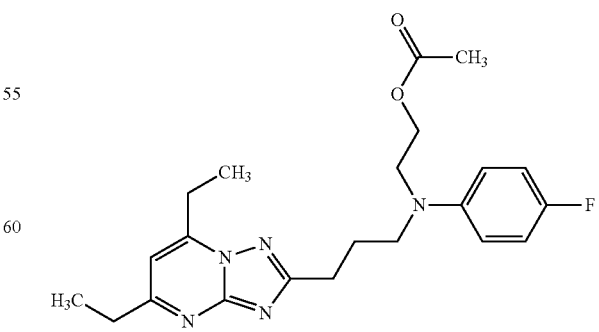

A mixture of 3,5-heptanedione (18.8 mg, 0.147 mmol), 2-{[3-(5-amino-1H-1,2,4-triazol-3-yl)propyl](4-fluorophenyl)amino}ethan-1-ol (50 mg, 0.179 mmol), and glacial acetic acid (1 mL) was added to a 50 mL RBF with a magnetic stirring bar. The flask was fitted with a condenser, and warmed in an oil bath to a gentle reflux at 135° C. for 18 h. Progress of the reaction was monitored by analytical HPLC with UV detection ($R_t$=5.5 min). The mixture was added to stirring ice/water (15 mL), and the pH was adjusted to basic with 1 N sodium hydroxide. The aqueous layer was extracted with ethyl acetate (2×20 mL). The combined organic layers were dried ($Na_2SO_4$), filtered and concentrated under reduced pressure. The crude material was purified by silica gel chromatography using a gradient elution of 65-100% ethyl acetate in hexanes. The material was concentrated under reduced pressure and the title compound was obtained (20 mg, 37%). EM (calc.): 413.2; MS (ESI) m/e: 414.2 $(M+H)^+$. $^1$H NMR (DMSO-$d_6$, 400 MHz) δ ppm: 7.11 (s, 1H), 6.97 (m, 2H), 6.75 (m, 2H), 4.12 (t, 2H), 3.54 (t, 2H), 3.40 (t, 2H), 3.10 (q, 2H), 2.88 (m, 4H), 1.99 (m, 2H), 1.95 (s, 3H), 1.35 (t, 3H), 1.28 (t, 3H).

Example 22

2-[3-(4-chlorophenoxy)propyl]-5-methyl-7-(trifluoromethyl)-[1,2,4]triazolo[1,5-a]pyrimidine Methyl 4-(4-chlorophenoxy)butanoate

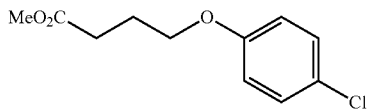 [SMILES: COC(=O)CCCOc1ccc(Cl)cc1]

A mixture of methyl 4-bromobutyrate (1.5 g, 8.29 mmol), 4-chlorophenol (1.17 g, 9.11 mmol), potassium carbonate (2.86 g, 20.7 mmol), and anhydrous N,N-dimethylformamide (5 mL) was added to a 25 mL RBF with a magnetic stirring bar. The mixture was allowed to stir at room temperature for 16 hours. Progress of the reaction was monitored by analytical HPLC with UV detection ($R_t$=6.5 min). The mixture was added to stirring ice/water (150 mL) and extracted with ethyl acetate (2×30 mL). The combined organic layers were washed with saturated aqueous NaCl (2×30 mL), dried ($Na_2SO_4$), filtered, and concentrated under reduced pressure. The crude material was purified by silica gel column chromatography using a gradient elution of 0-100% ethyl acetate in hexanes to afford the title compound as a clear oil (1.45 g, 76% yield).

3-[3-(4-chlorophenoxy)propyl]-1H-1,2,4-triazol-5-amine

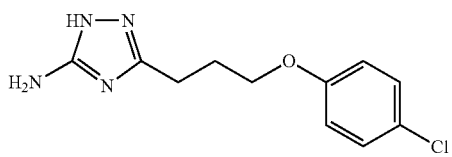 [SMILES: Nc1nc(CCCOc2ccc(Cl)cc2)n[nH]1]

A mixture of methyl 4-(4-chlorophenoxy)butanoate (1.4 g, 6.13 mmol), aminoguanidine bicarbonate (2.08 g, 15.3 mmol), and pyridine (12 mL) was added to a 100 mL RBF with a magnetic stirring bar. The flask was fitted with a condenser, and heated to 125° C. using an oil bath. Progress of the reaction was monitored by analytical HPLC with UV detection at 215 nm. The mixture was heated for 20 hours, and an additional portion of aminoguanidine bicarbonate (0.60 g, 4.4 mmol) was added. After an additional 22 hours of heating, the reaction was complete. The reaction allowed to cool to ambient temperature, concentrated under reduced pressure and partitioned between ethyl acetate (50 mL) and water (20 mL). The aqueous layer was extracted once more with ethyl acetate (30 mL). The combined organic layers were washed with saturated aqueous NaCl (2×15 mL), dried ($Na_2SO_4$), filtered and concentrated. Dichloromethane (5 mL) was added and a precipitate that formed was isolated by filtration, rinsed with dichloromethane (5 mL), and then dried under reduced pressure to afford the title compound as a white powder (1.12 g, 72% yield).

2-[3-(4-chlorophenoxy)propyl]-5-methyl-7-(trifluoromethyl)[1,2,4]triazolo[1,5-a]pyrimidine

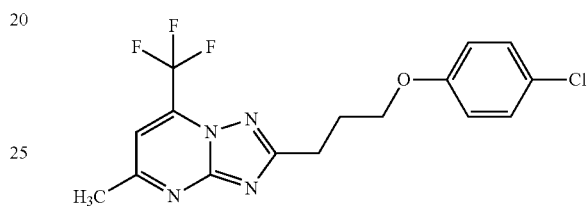

A mixture of 1,1,1-trifluoro-2,4-pentanedione (91 mg, 0.594 mmol), 3-[3-(4-chlorophenoxy)propyl]-1H-1,2,4-triazol-5-amine (150 mg, 0.594 mmol), and glacial acetic acid (2.0 mL) was added to a 50 mL RBF with a magnetic stirring bar. The flask was fitted with a condenser, and warmed in an oil bath to a gentle reflux at 135° C. Progress of the reaction was monitored by analytical HPLC with UV detection at 215 nm. The starting material elutes with retention time of 5.1 min, and the product elutes with retention time of 6.89 min. After 15 h, the solution was allowed to cool to room temperature and added to stirring ice/water (17 mL). Solid material was isolated by filtration, rinsed with 15 mL of water, and then dried under reduced pressure. The solid was dissolved in ethanol (3 mL) and water (1 mL) with gentle warming and allowed to cool. The needles that formed were isolated by filtration, washed with 3 mL of cold ethanol, and allowed to dry to afford the title compound (92 mg, 41% yield). $^1$H NMR (DMSO-$d_6$, 400 MHz) δ ppm: 7.83 (s, 1H), 7.31 (d, 2H), 6.95 (d, 2H), 4.09 (t, 2H), 3.03 (t, 2H), 2.70 (s, 3H), 2.21 (m, 2H).

Example 23

2-{[2-(4-chlorophenoxy)ethyl]sulfanyl}-5-methyl-7-(trifluoromethyl)-[1,2,4]-triazolo[1,5-a]pyrimidine 3-{[2-(4-chlorophenoxy)ethyl]sulfanyl}-1H-1,2,4-triazol-5-amine

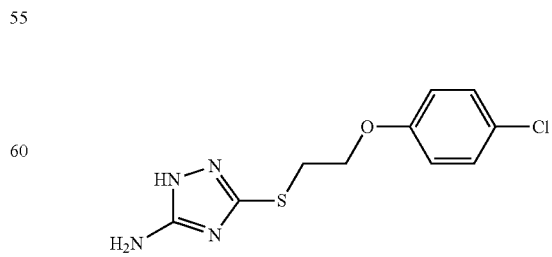

A mixture of 1-(2-bromoethoxy)-4-chlorobenzene (2.0 g, 8.49 mmol), 3-amino-5-mercapto-1,2,4-triazole (1.04 g, 8.92 mmol), potassium carbonate (2.34 g, 16.98 mmol), and anhydrous N,N-dimethylformamide (4 mL) was added to a 50 mL RBF with a magnetic stirring bar. The mixture was allowed to stir at ambient temperature for 3 days. Progress of the reaction was monitored by analytical HPLC with UV detection at 215 nm ($R_t$=6.04 min). The mixture was diluted with 40 mL of water and allowed to stir for 5 min. A precipitate was isolated by filtration, rinsed with 25 mL of water, and allowed to dry under reduced pressure. The solid material was >98% pure by analytical HPLC and afforded the title compound as a white powder (2.21 g, 96% yield). EM (calc.): 270.7; MS (ESI) m/e: 271.0 (M+H)$^+$. $^1$H NMR (DMSO-$d_6$, 400 MHz) δ ppm: 12.00 (br s, 1H), 7.32 (d, 2H), 7.00 (d, 2H), 6.04 (s, 2H), 4.19 (t, 2H), 3.30 (t, 2H).

2-{[2-(4-chlorophenoxy)ethyl]sulfanyl}-5-methyl-7-(trifluoromethyl)-[1,2,4]triazolo[1,5-a]pyrimidine

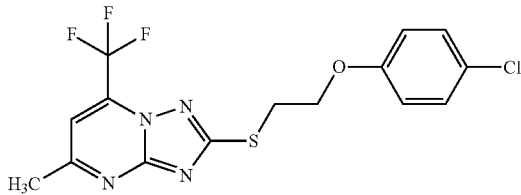

A mixture of 1,1,1-trifluoro-2,4-pentanedione (114 mg, 0.739 mmol), 3-{[2-(4-chlorophenoxy)ethyl]sulfanyl}-1H-1,2,4-triazol-5-amine (200 mg, 0.739 mmol), and glacial acetic acid (1.5 mL) was added to a 50 mL RBF with a magnetic stirring bar. The flask was fitted with a condenser and warmed in an oil bath to a gentle reflux at 135° C. The solution was heated for 15 hours. Progress of the reaction was monitored by analytical HPLC with UV detection at 215 and 254 nm. The starting material 3-{[2-(4-chlorophenoxy)ethyl]sulfanyl}-1H-1,2,4-triazol-5-amine elutes with retention time of 6.04 min, and the product elutes with retention time of 7.98 min. The solution was allowed to cool to room temperature and added into stirring ice/water (15 mL) to precipitate the product. Solids were isolated by filtration, rinsed with 20 mL of water, and then dried under reduced pressure. The solid was dissolved in 5 mL of ethanol with gentle warming and allowed to cool. The fine white needles that formed were isolated by filtration, washed with 3 mL of cold ethanol, and dried to afford the title compound as off-white crystals (186 mg, 65% yield). EM (calc.): 388.0; MS (ESI) m/e: 389.0 (M+H)$^+$. $^1$H NMR (DMSO-$d_6$, 400 MHz) δ ppm: 7.85 (s, 1H), 7.31 (d, 2H), 7.00 (d, 2H), 4.33 (t, 2H), 3.62 (t, 2H), 2.69 (s, 3H). $^{19}$F NMR (DMSO-$d_6$, 376 MHz) δ ppm: −67.56 (s).

Example 24

2-{[2-(4-chlorophenoxy)ethyl]sulfanyl}-5,7-bis(trifluoromethyl)-[1,2,4]-triazolo[1,5-a]pyrimidine The title compound was prepared according to the experimentals described for Example 23 above from 3-{[2-(4-chlorophenoxy)ethyl]sulfanyl}-1H-1,2,4-triazol-5-amine and hexafluoroacetylacetone in 32% yield; EM (calc.): 442.0; MS (ESI) m/e: 443.0 (M+H)$^+$. $^1$H NMR (DMSO-$d_6$, 400 MHz) δ ppm: 8.40 (s, 1H), 7.32 (d, 2H), 7.01 (d, 2H), 4.36 (t, 2H), 3.71 (t, 2H). $^{19}$F NMR (DMSO-$d_6$, 376 MHz) δ ppm: −66.84 (s), −67.45 (s).

Example 25

2-{[2-(4-chlorophenoxy)ethyl]sulfanyl}-[1,2,4]-triazolo[1,5-a]pyrimidine

The title compound was prepared according to the experimentals described for Example 23 above from 3-{[2-(4-chlorophenoxy)ethyl]sulfanyl}-1H-1,2,4-triazol-5-amine and malonaldehyde bis(diethyl acetal) in 42% yield; EM (calc.): 306.0; MS (ESI) m/e: 307.0 (M+H)$^+$. $^1$H NMR (DMSO-$d_6$, 400 MHz) δ ppm: 9.33 (dd, 1H), 8.81 (dd, 1H), 7.31 (m, 3H), 7.02 (dt, 2H), 4.33 (t, 2H), 3.62 (t, 2H).

Example 26

2-{[2-(4-chlorophenoxy)ethyl]sulfanyl}-5-methyl-[1,2,4]triazolo[1,5-a]pyrimidine and Example 27

2-{[2-(4-chlorophenoxy)ethyl]sulfanyl}-7-methyl-[1,2,4]-triazolo[1,5-a]pyrimidine The title compound was prepared according to the experimentals described for Example 23 above from 3-{[2-(4-chlorophenoxy)ethyl]sulfanyl}-1H-1,2,4-triazol-5-amine and acetylacetaldehyde dimethyl acetal. The two regioisomers were separated by silica gel chromatography. 2-{[2-(4-chlorophenoxy)ethyl]sulfanyl}-5-methyl-[1,2,4]triazolo[1,5-a]pyrimidine was obtained as off white crystals in 25% yield: EM (calc.): 320.0; MS (ESI) m/e: 321.0 (M+H)$^+$. $^1$H NMR (CDCl$_3$, 400 MHz) δ ppm: 8.53 (d, 1H, J=6.8 Hz), 7.22 (d, 2H), 6.90 (d, 1H, J=6.8 Hz), 6.87 (d, 2H), 4.34 (t, 2H), 3.63 (t, 2H), 2.70 (s, 3H).
2-{[2-(4-chlorophenoxy)ethyl]sulfanyl}-7-methyl-[1,2,4]triazolo[1,5-a]pyrimidine was obtained as off white crystals in 15% yield: EM (calc.): 320.0; MS (ESI) m/e: 321.0 (M+H)$^+$. $^1$H NMR (CDCl$_3$, 400 MHz) δ ppm: 8.61 (d, 1H, J=4.4 Hz), 7.22 (d, 2H), 6.90 (d, 2H), 6.88 (d, 1H, J=4.4 Hz), 4.36 (t, 2H), 3.67 (t, 2H), 2.80 (s, 3H).

Example 28

2-[3-(4-chlorophenoxy)propyl]-5,7-diethyl-[1,2,4]triazolo[1,5-a]pyrimidine

The title compound was prepared according to the experimentals described for Example 22 above from 3-[3-(4-chlorophenoxy)propyl]-1H-1,2,4-triazol-5-amine and 3,5-heptanedione in 44% yield; $^1$H NMR (DMSO-$d_6$, 400 MHz) δ ppm: 7.31 (dd, 1H), 7.29 (dd, 1H), 7.11 (s, 1H), 6.96 (dd, 1H), 6.94 (dd, 1H), 4.08 (t, 2H), 3.07 (q, 2H), 2.97 (t, 2H), 2.86 (q, 2H), 2.20 (m, 2H), 1.33 (t, 3H), 1.27 (t, 3H).

Example 29

2-[3-(4-fluorophenoxy)propyl]-5,7-bis(propan-2-yl)-[1,2,4]triazolo[1,5-a]pyrimidine The title compound was prepared according to the experimentals described for Example 22 above from 3-[3-(4-fluorophenoxy)propyl]-1H-1,2,4-triazol-5-amine and 2,6-dimethyl-3,5-heptanedione in 61% yield. The reagent 3-[3-(4-fluorophenoxy)propyl]-1H-1,2,4-triazol-5-amine was prepared by a similar procedure for the synthesis of 3-[3-(4-chlorophenoxy)propyl]-1H-1,2,4-triazol-5-amine in Example 22 above, beginning from 4-fluorophenol instead of 4-chlorophenol. EM (calc.): 356.2; MS (ESI) m/e: 357.4 (M+H)+.

Example 30

5,7-bis(difluoromethyl)-2-[3-(4-fluorophenoxy)propyl]-[1,2,4]triazolo[1,5-a]pyrimidine The title compound was prepared according to the experimentals described for Example 22 above from 3-[3-(4-fluorophenoxy)propyl]-1H-1,2,4-triazol-5-amine and 1,1,5,5-tetrafluoropentane-2,4-dione in 72% yield. The reagent 3-[3-(4-fluorophenoxy)propyl]-1H-1,2,4-triazol-5-amine was prepared by a similar procedure for the synthesis of 3-[3-(4-chlorophenoxy)propyl]-1H-1,2,4-triazol-5-amine in Example 22 above, beginning from 4-fluorophenol instead of 4-chlorophenol. $^1$H NMR (DMSO-$d_6$, 400 MHz) δ ppm: 7.83 (s, 1H), 7.63 (t, 1H), 7.18 (t, 1H), 7.09 (m, 2H), 6.95 (m, 2H), 4.08 (t, 2H), 3.11 (t, 2H), 2.24 (m, 2H).

Example 31

4-[2-({5,7-dimethyl-[1,2,4]triazolo[1,5-a]pyrimidin-2-yl}sulfanyl)ethoxy]pyridine 2-({5,7-dimethyl-[1,2,4]-triazolo[1,5-a]pyrimidin-2-yl}sulfanyl)ethan-1-ol

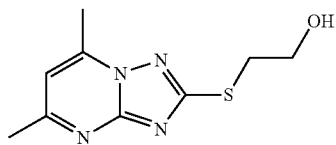

The compound of the first step was prepared according to the experimentals described for Example 1 above from of 5,7-dimethyl-[1,2,4]triazolo[1,5-a]pyrimidine-2-thiol and 2-bromoethanol in 84% yield; EM (calc.): 224.1; MS (ESI) m/e: 225.0 (M+H)+. $^1$H NMR (DMSO-$d_6$, 400 MHz) δ ppm: 7.09 (s, 1H), 5.05 (s, 1H), 3.70 (t, 2H), 3.30 (t, 2H), 2.66 (s, 3H), 2.54 (s, 3H).

4-[2-({5,7-dimethyl-[1,2,4]-triazolo[1,5-a]pyrimidin-2-yl}sulfanyl)ethoxy]pyridine

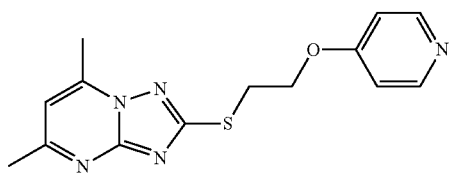 [SMILES: Cc1cc(C)n2nc(SCCOc3ccncc3)nc2n1]

A mixture of 2-({5,7-dimethyl-[1,2,4]triazolo[1,5-a]pyrimidin-2-yl}sulfanyl)ethan-1-ol (100 mg, 0.446 mmol), triphenylphosphine (175 mg, 0.670 mmol), 4-hydroxypyridine (55 mg, 0.58 mmol), and tetrahydrofuran (0.5 mL) was added to a 20 mL scintillation vial. The mixture was placed in a sonicating bath, and diisopropyl azodicarboxylate (0.133 mL, 0.67 mmol) was added dropwise. Sonication was allowed to continue for 15 min, and progress of the reaction was monitored by HPLC with UV detection at 215 nm. Water (5 mL) was added to the mixture, stirred, and decanted. The oily residue was dissolved in 50 mL of ethyl acetate and extracted with 3 mL of 1 M aqueous HCl. The acidic layer was separated, and the pH was adjusted to basic with saturated aqueous sodium bicarbonate. The basic layer was extracted with 4 mL of ethyl acetate which was dried (Na$_2$SO$_4$), filtered, and concentrated under reduced pressure. The crude material was purified by silical gel chromatography using a gradient elution of 0-10% methanol in dichloromethane. The title compound was obtained as a white powder (0.025 g, 19% yield). EM (calc.): 301.1; MS (ESI) m/e: 302.1 (M+H)+. $^1$H NMR (DMSO-$d_6$, 400 MHz) δ ppm: 8.38 (dd, 2H), 7.13 (s, 1H), 7.04 (dd, 2H), 4.43 (t, 2H), 3.62 (t, 2H), 2.67 (s, 3H), 2.55 (s, 3H).

Example 32

(2-{4-[2-({5,7-dimethyl-[1,2,4]triazolo[1,5-a]pyrimidin-2-yl}sulfanyl)ethoxy]phenyl}ethyl)-dimethylamine The title compound was prepared according to the experimentals described for Example 31 above from of 2-(5,7-dimethyl-[1,2,4]triazolo[1,5-a]pyrimidin-2-yl sulfanyl) ethan-1-ol and N,N-dimethyltyramine in 48% yield; EM (calc.): 371.2; MS (ESI) m/e: 372.2 (M+H)+.

Example 33

2-{[2-(cyclohexyloxy)ethyl]sulfanyl}-5,7-dimethyl-[1,2,4]triazolo[1,5-a]pyrimidine 2-Bromoethoxy cyclohexane

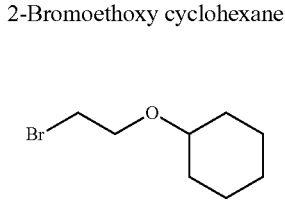

A mixture of 2-(cyclohexyloxy)ethanol (0.5 g, 3.47 mmol), carbon tetrabromide (1.49 g, 4.51 mmol), and dichloromethane (6 mL) was placed in a 20 mL scintillation vial with a magnetic stirring bar and cooled on an ice-water bath. Triphenylphosphine (1.18 g, 4.51 mmol) was added in three portions over 5 min with stirring. The mixture was allowed to warm to ambient temperature and progress was monitored with TLC using ethyl acetate:hexanes (1:1) ($R_f$ starting material=0.6, $R_f$ product=0.9). The mixture was concentrated under reduced pressure. Hexanes (5 mL) and ethyl ether (10 mL) were added twice and removed by decanting, leaving an oily residue that was purified by silical gel chromatography using hexanes as eluant. The title compound was obtained as a yellow oil (0.189 g, 26% yield).

2-{[2-(cyclohexyloxy)ethyl]sulfanyl}-5,7-dimethyl-[1,2,4-]triazolo[1,5-a]pyrimidine

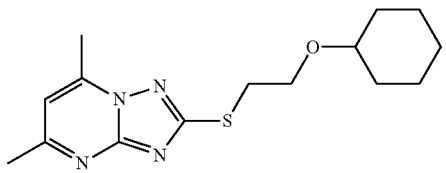 [SMILES: Cc1cc(C)n2nc(SCCOC3CCCCC3)nc2n1]

The title compound was prepared according to the experimentals described for Example 1 above from 5,7-dimethyl-

[1,2,4]triazolo[1,5-a]pyrimidine-2-thiol and 2-bromoethoxy cyclohexane in 78% yield; EM (calc.): 306.2; MS (ESI) m/e: 307.2 (M+H)+.

Example 34

3-[2-({5,7-dimethyl-[1,2,4]triazolo[1,5-a]pyrimidin-2-yl}sulfanyl)ethyl]-1H-indole The title compound was prepared according to the experimentals described for Example 9 above from 5,7-dimethyl-[1,2,4]triazolo[1,5-a]pyrimidine-2-thiol and 2-(1H-indol-3-yl)ethanol in 54% yield; EM (calc.): 323.1; MS (ESI) m/e: 324.1 (M+H)+.

Example 35

2-{2-[(4-chlorophenyl)sulfanyl]ethoxy}-5,7-dimethyl-[1,2,4]triazolo[1,5-a]pyrimidine The title compound was prepared according to the experimentals described for Example 11 above from 2-methanesulfonyl-5,7-dimethyl-[1,2,4]triazolo[1,5-a]pyrimidine and 2-[(4-chlorophenyl)sulfanyl]ethan-1-ol in 38% yield. $^1$H NMR (DMSO-$d_6$, 400 MHz) δ ppm: 7.47 (dd, 1H), 7.45 (dd, 1H), 7.39 (dd, 1H), 7.37 (dd, 1H), 7.08 (s, 1H), 4.51 (t, 2H), 3.45 (t, 2H), 2.62 (s, 3H), 2.52 (s, 3H).

Example 36

Pharmaceutical Composition Examples

The following are representative pharmaceutical formulations containing a compound of Formula I.

Tablet Formulation

The following ingredients are mixed intimately and pressed into single scored tablets:

| Ingredient | Quantity per tablet (mg) |
| --- | --- |
| Compound described herein | 400 |
| Cornstarch | 50 |
| Croscarmellose sodium | 25 |
| Lactose | 120 |
| Magnesium stearate | 5 |

Capsule Formulation

The following ingredients are mixed intimately and loaded into a hard-shell gelatin capsule:

| Ingredient | Quantity per tablet (mg) |
| --- | --- |
| Compound described herein | 200 |
| Lactose | 148 |
| Spray-dried magnesium stearate | 2 |

Suspension Formulation

The following ingredients are mixed to form a suspension for oral administration:

| Ingredient | Amount |
| --- | --- |
| Compound described herein | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 mL |
| Colorings | 0.5 mg |
| Distilled water | q.s. to 100 mL |

Injectable Formulation

The following ingredients are mixed to form an injectable formulation:

| Ingredient | Amount |
| --- | --- |
| Compound described herein | 1.2 g |
| Sodium acetate buffer solution | 2.0 mL of 0.4M |
| HCI (1N) or NaOH (1M) | q.s. to suitable pH |
| Water (distilled, sterile) | q.s. to 20 mL |

All of the above ingredients, except water, are combined and heated to 60-70° C. with stirring. A sufficient quantity of water at 60° C. is then added with vigorous stirring to emulsify the ingredients, and water then added q.s. to 100 g.

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| Ingredient | Quantity per tablet (mg) |
| --- | --- |
| Compound described herein | 500 |
| Witepsol ® H-15 | balance |

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled. All patents, patent applications and publications cited in this application are hereby incorporated by reference in their entirety for all purposes to the same extent as if each individual patent, patent application or publication were so individually denoted.

Example 37

Neuroprotective activities of the EPO mimetic compounds of the invention were demonstrated using neuronal cell lines in vitro. FIG. 1 shows the neuroprotective effect of Compound 1 in vitro using PC12 neural cells (ATCC, catalog No. CRL-1721). PC12 cells were cultured in DMEM supplemented with 10% fetal calf serum and 5% horse serum. EPO mimetics or rhEPO were added after removal of serum and the cells were subsequently cultured for an additional 72 hours under serum-free conditions. Cell survival of the serum-starved cells was analyzed by CellTiter-Glo® reagent luminescence reading. Compound 1 protected PC12 cells with significant effect observed at concentration of 1 uM, with at least a comparable effect on cell viability as rhEPO (FIG. 1). Compound 1 concentration of 5 uM provided even higher level of protection than rhEPO at 10 U/ml.

Figure 2:
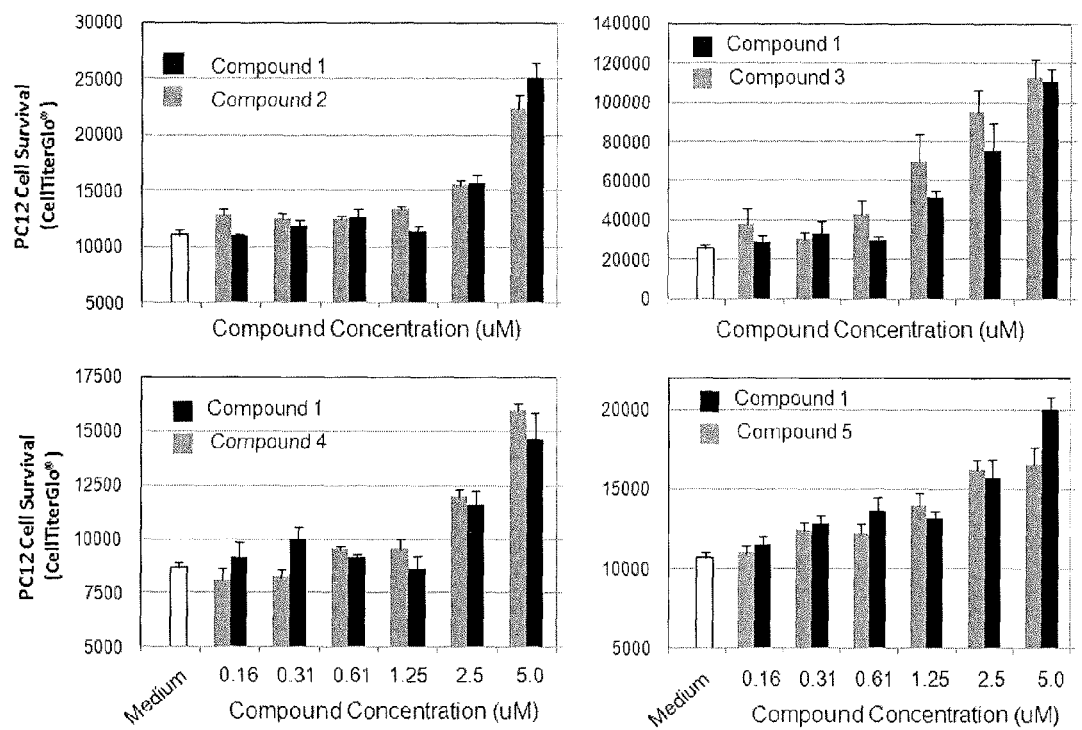
FIG. 2 shows the effects of EPO mimetics, Compounds 1-5, on protection of rat PC12 cells from cell death upon serum starvation. PC12 cells were cultured in DMEM supplemented with 10% fetal calf serum and 5% horse serum. EPO mimetics or rhEPO were added and the cells were cultured in triplicate for 72 hours under serum-free conditions. Cell viability was analyzed by CellTiter-Glo® reagent (Promega).

FIG. 2 illustrates neuroprotective effects of Compounds 1-5 when tested in PC12 cell protection assays. PC12 cells were subjected to serum deprivation as described under FIG. 1. Compounds 1-5 demonstrated potent activities and enhanced PC12 cell survival at levels comparable to those observed in the presence of Compound 1 (FIG. 2).

Example 38

Figure 3:
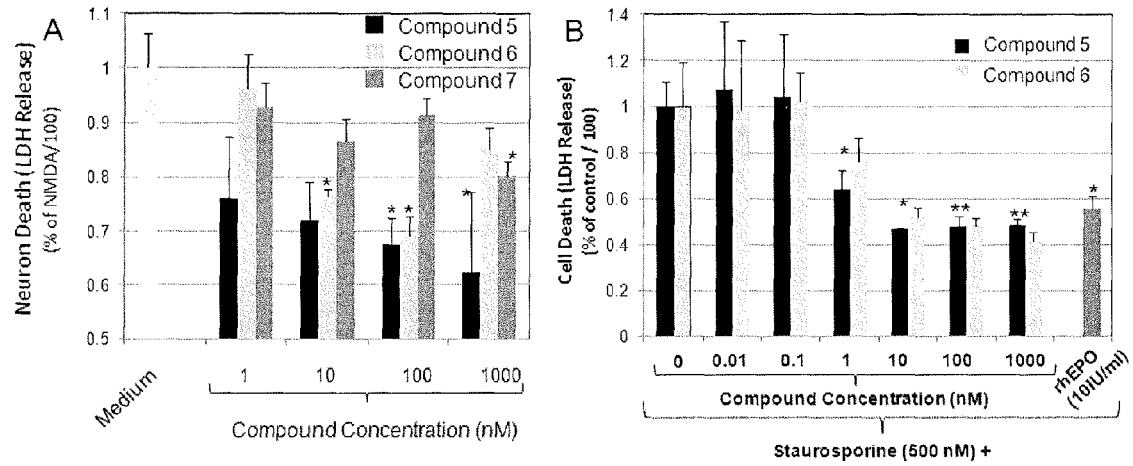
FIG. 3 shows the neuroprotective effects of EPO mimtetics, Compounds 5-7, using primary rat cortical neurons (12 days in vitro) (FIG. 3A), and primary human neurons (47 days in culture) (FIG. 3B).

Neuroprotective effects of the compounds were demonstrated using primary neurons. FIG. 3 shows neuroprotective effects of Compounds 5-7 using primary rat and human cortical neurons. Significant protective effects of the compounds were observed (FIG. 3). A) Primary rat cortical neurons were isolated from micro-surgically dissected regions of day 18 embryonic rat brain (Brain Bits, LLC, Springfield, Ill.) and cultured for 12 days in vitro. Then, Compounds 5-7 were added for 24 h. Next, NMDA (50 uM) was added and the cells were cultured for an additional 24 hours. Cells cultured without the insult were considered to represent 0% neuron death. The data represent mean±SEM of six replicate cultures and * indicates P value ≤0.05. B) Primary micro-dissected fetal brain tissue was obtained from a commercial source (Advanced Bioscience Resources, Inc., Alameda, Calif.). Primary human neurons (47 days in culture) were cultured in the presence and absence of rhEPO or Compound 5 or Compound 6 for 24 h. Staurosporine (500 nM) was added and the cells were cultured for an additional 24 hours. Cells cultured without the insult were considered to represent 0% neuron death. The data represent mean±SEM of six replicate cultures and * indicates P value ≤0.05.

Example 39

Figure 4:
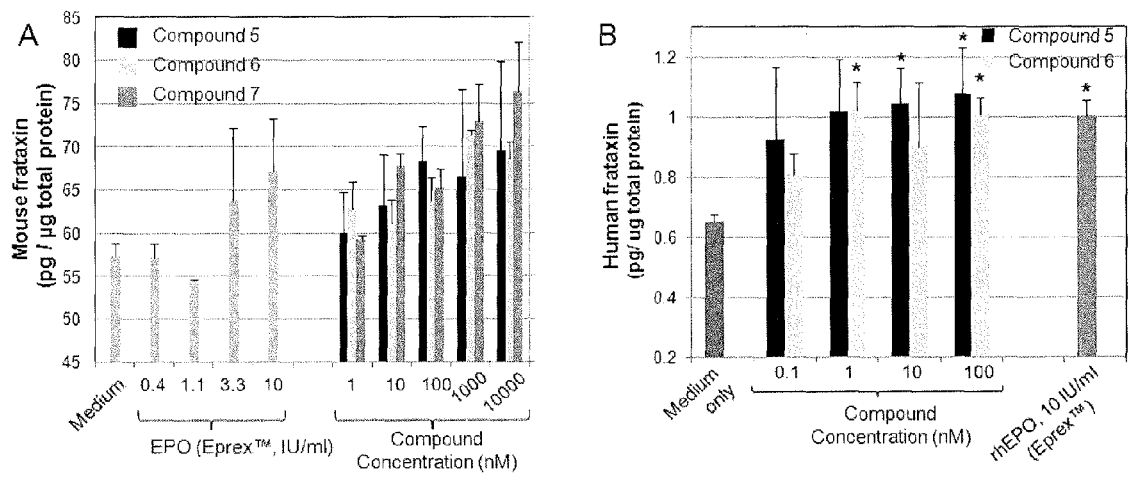
FIG. 4 shows the effects of EPO mimetics, Compounds 5-7, on frataxin protein levels in vitro using embryonic mouse cell line P19 (FIG. 4A) and Primary human fetal neurons (28 days in culture) (FIG. 4B).

The effects of the compounds on frataxin protein levels in cells were analyzed. FIG. 4 demonstrates increased frataxin protein levels in response to Compounds 5-7 (A) or Compounds 5 and 6 (B). Embryonic mouse cell line P19 was differentiated into neuronal cells in the presence of retinoic acid and frataxin levels were measured (FIG. 4A). Frataxin levels were measured after 24 h by multi-species frataxin-ELISA (MitoSciences) and compared to total protein levels. The data represent mean±SEM. Primary human fetal neurons (28 days in culture) were also incubated for 24 h in the presence of the compounds, and human frataxin levels were measured by ELISA (MitoSciences) and compared to total protein levels (FIG. 4B). The data represent mean±SEM of triplicate measurements. Compounds were also tested for their effects on frataxin levels in cells derived from patients with FRDA. Cultures of patient peripheral blood mononuclear cells (PBMCs) were also used to test the EPO mimetic compounds for frataxin enhancement in frataxin-deficient cells. Compound 1 and Compounds 5-6 enhanced frataxin levels in these patient cells at concentration 1 uM or lower. The level of frataxin enhancement in the presence of the compounds was comparable to that observed in the presence of rhEPO at 10 U/ml.

Example 40

Figure 5:
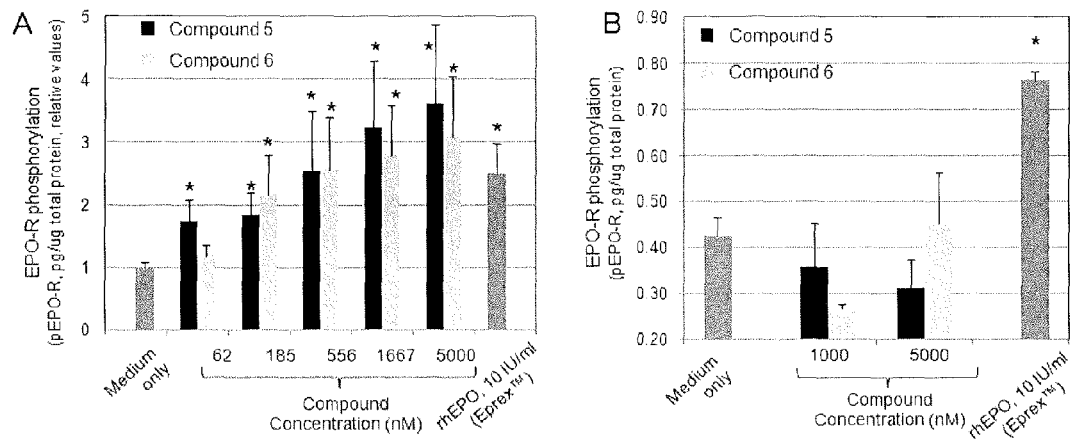
FIG. 5 shows the effects of EPO mimetics, Compounds 5 and 6, on EPO receptor activation in neuronal cells in vitro.

EPO receptor activation in response to compounds was demonstrated in neuronal cells. Primary micro-dissected fetal brain tissue was obtained from a commercial source (Advanced Bioscience Resources, Inc., Alameda, Calif.). Cultured primary human fetal neural cells (3 h, 1 day, 17 days, or 26 days in culture) were incubated with Compound 5, Compound 6, or controls for 10 min (FIG. 5A). Phospho-EPOR was detected by ELISA (R&D Systems). Compound 5 and Compound 6 increased EPO receptor phosphorylation in a dose-dependent manner (FIG. 5A; mean±SEM from four independent experiments). The level of receptor activation was comparable to that induced by recombinant human EPO (10 IU/ml). The same compounds did not activate EPO receptor in erythroleukemia cell line TF-1 (FIG. 5B), while positive control recombinant EPO was effective. Human erythropoietic cell line TF-1 was cultured for 10 min in the presence of Compound 5, Compound 6, or the controls, and phospho-EPOR was detected by ELISA (R&D Systems). The data represent mean±SEM of triplicate cultures. The results indicate an increased ratio of EPO receptor activation on neuronal cells when compared to erythropoietic cells. The receptor activation results were consistent with functional cell based assays using primary human CD34+ bone marrow progenitor cells and erythroleukemia cell line TF-1. Compound 5 and Compound 6 did not induce proliferation of TF-1 cells at concentrations that provided significant neuroprotective effects.

Example 41

Figure 6:
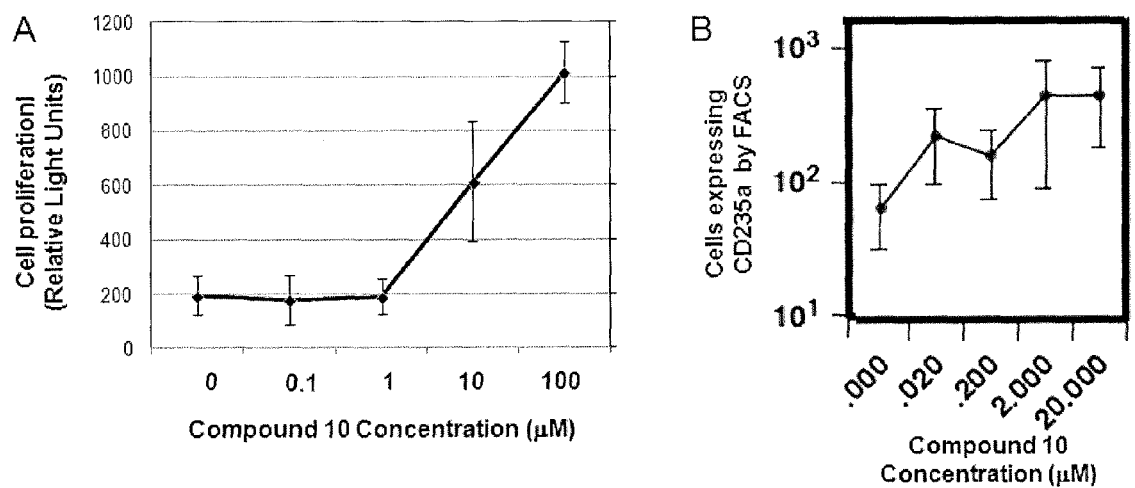
FIG. 6 shows effects of an EPO mimetic, Compound 10, on proliferation and differentiation of primary human CD34+ cells.

Compound 10 was tested at different concentrations for its ability to induce proliferation and differentiation of human CD34+ hematopoietic stem cells. Human CD34+ cells were purified by (FIG. 6A) immunomagnetic beads (>90% purity, purchased from Stem Cell Technologies) or (FIG. 6B) cell sorting (at Blood Systems Research Institute) and the cells were cultured in the presence of compounds for eight (FIG. 6A) or eleven (FIG. 6B) days. (FIG. 6A) The level of cell growth and survival was measured based on ATP levels (Cell-TiterGlo reagent), or (FIG. 6B) the expression level of CD235a was analyzed by flow cytometry as a marker for cell maturation. Cell survival was analyzed using the CellTiter-Glo reagent to measure ATP levels as a marker of metabolically active cells that have not undergone apoptosis, and expression of CD235a as a marker of erythroid cell differentiation and as a specific marker for EPO-like erythropoietic activity. FIG. 6 demonstrates dose-dependent induction of CD34+ progenitor cell proliferation, as well as differentiation into erythroid cells expressing CD235a. These data further illustrate an EPO-like erythropoietic activity of Compound 10.

Example 42

Figure 7:
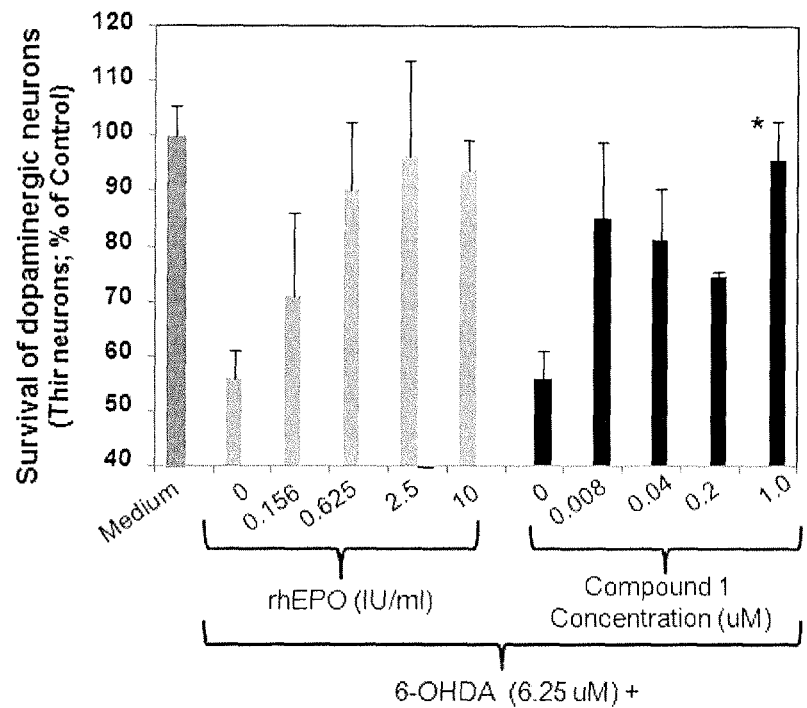
FIG. 7 shows the effects of and EPO mimetic, Compound 1, on protecting primary dopaminergic neurons as measured by staining for tyrosine hydroxylase-immunoreactive (THir) neurons. Dissociated embryonic D14 rat ventral mesencephalic cells were used.

Dopaminergic neurons play a key role in the pathogenesis of Parkinson's disease and compounds enhancing survival of these cells have significant therapeutic potential. Dissociated embryonic D14 rat ventral mesencephalic cells were used to test the potential of EPO mimetic compounds to protect primary dopaminergic neurons. Both recombinant EPO (10 IU/ml) and Compound 1 (1 uM) significantly protected dopaminergic neurons from the toxicity of 6-hydroxydopamine (6-OHDA) (FIG. 7). The cells were plated in 48-well poly-D-lysine coated plates using a microisland technique. The microislands were seeded into dry plates in 10 uL aliquots of 3000 cells/uL and incubated at 37° C. for 1 h to allow for adhesion. The wells were flooded with hormone supplemented serum-free media alone, Compound 1, or rhEPO. On day 3, the medium was replaced with 6.25 uM 6-hydroxydopamine (6-OHDA, Sigma) for a 40 minute incubation. The toxin was then removed and the cells were cultured for an additional 2 days. On day 5, the cells were fixed, permeabilized and stained for tyrosine hydroxylase-immunoreactive (THir) neurons.

Example 43

Figure 8:
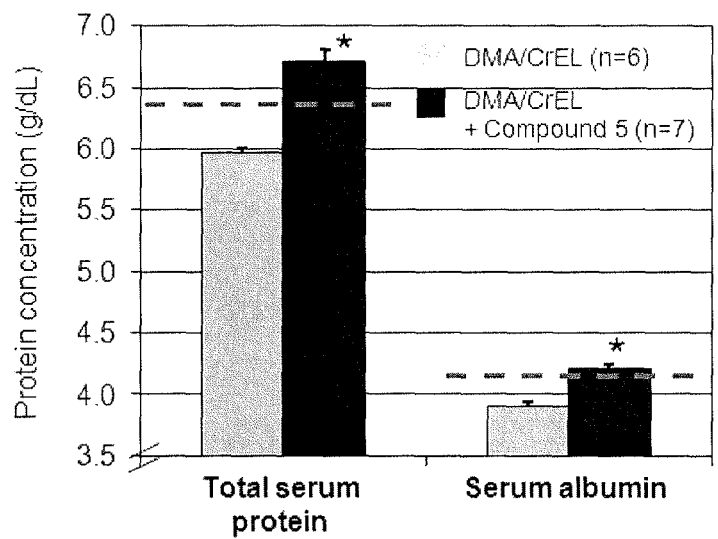
FIG. 8 shows the kidney protective effects of an EPO mimetic, Compound 5, in vivo in rats as measured by reduced hypoproteinemia in serum.

Kidney and CNS protective effects of Compound 5 were demonstrated in vivo in rats. High-dose N,N-dimethylacetamide (DMA)+Cremophor EL (CrEL) (2.5 mL/kg each, IP) was used to induce acute CNS and organ toxicity, and the potential of Compound 5 to protect the rats was studied. Kidney-protective effects, as measured by reduced hypoproteinemia in serum, were observed (FIG. 8). Compound 5 also prevented the CNS toxicity of DMA/CrEL and normalized the response of the rats to formalin injection. The results indicate beneficial protective effects of Compound 5 in multiple organs in vivo.

Example 44

Effects of the EPO mimetic compounds of the invention on neuronal cell survival were demonstrated using PC12 cell line in vitro (ATCC, catalog No. CRL-1721). PC12 cells were cultured in DMEM supplemented with 10% fetal calf serum and 5% horse serum. EPO mimetics or rhEPO were added after removal of serum and the cells were subsequently cultured for an additional 72 hours under serum-free conditions. Cell survival of the serum-starved cells was analyzed by CellTiter-Glo® reagent luminescence reading (relative light units, "RLU"). Compound concentrations are shown at which >25% increase in RLU was demonstrated when compared to medium control. "NS" indicates RLU increased <25% when compounds were tested at 5 uM.

TABLE 1

| Example Number (Compound Number from FIGS. 1-8) | PC12 cell proliferation (CellTiter-Glo ®) Concentration at which RLU increased >25% compared to medium control |
| --- | --- |
| 1 (Compound 1) | <5 uM |
| 2 | <5 uM |
| 3 | <5 uM |
| 4 | <5 uM |
| 5 | <5 uM |
| 6 | <5 uM |
| 7 | <5 uM |
| 8 | <5 uM |
| 9 (Compound 2) | <5 uM |
| 10 (Compound 10) | NS |
| 11 (Compound 5) | <5 uM |
| 12 | <5 uM |
| 13 (Compound 6) | <5 uM |
| 14 | <5 uM |
| 15 | <5 uM |
| 16 | <5 uM |
| 17 | <5 uM |
| 18 (Compound 7) | <5 uM |
| 19 | <5 uM |
| 20 (Compound 4) | <5 uM |
| 21 | <5 uM |
| 22 | <5 uM |
| 23 | <5 uM |
| 24 | <5 uM |

TABLE 1-continued

| Example Number (Compound Number from FIGS. 1-8) | PC12 cell proliferation (CellTiter-Glo ®) Concentration at which RLU increased >25% compared to medium control |
| --- | --- |
| 25 | <5 uM |
| 26 | <5 uM |
| 27 | <5 uM |
| 28 (Compound 3) | <5 uM |
| 29 | <5 uM |
| 30 | <5 uM |
| 31 | NS |
| 32 | NS |
| 33 | NS |
| 34 | <5 uM |
| 35 | <5 uM |

What is claimed is:

1. A compound of formula (I)

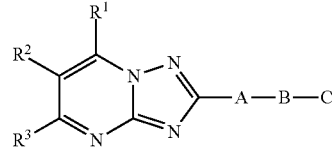

and/or pharmaceutically acceptable salts, solvates, and/or esters thereof, wherein:

A is O, $NR^4$, $C(R^5R^6)_n$, or bond;

B is a member selected from substituted or unsubstituted alkylene, substituted or unsubstituted alkyleneoxy, substituted or unsubstituted alkylenesulfanyl, substituted or unsubstituted alkylenesulfinyl, substituted or unsubstituted alkylenesulfonyl, substituted or unsubstituted alkyleneamino, and substituted or unsubstituted alkylenecarbonylamino;

C is a member selected from substituted or unsubstituted alkyl, substituted or unsubstituted cycloalkyl, and substituted or unsubstituted aryl;

$R^1$ is a member selected from hydrogen, halo, substituted or unsubstituted alkyl, substituted or unsubstituted haloalkyl, substituted or unsubstituted alkoxy, substituted or unsubstituted cycloalkyl, and substituted or unsubstituted heterocycloalkyl;

$R^2$ is a member selected from hydrogen, halo, hydroxy, and substituted or unsubstituted alkyl;

$R^3$ is a member selected from hydrogen, halo, substituted or unsubstituted alkyl, substituted or unsubstituted haloalkyl, substituted or unsubstituted alkoxy, substituted or unsubstituted cycloalkyl, and substituted or unsubstituted heterocycloalkyl;

Each $R^4$, $R^5$, and $R^6$ is independently selected from hydrogen, substituted or unsubstituted alkyl, substituted or unsubstituted haloalkyl, substituted or unsubstituted hydroxyalkyl, substituted or unsubstituted alkoxyalkyl, substituted or unsubstituted aminoalkyl, substituted or unsubstituted alkylaminoalkyl, and substituted or unsubstituted dialkylaminoalkyl; and n is 0 to 3.

2. A compound of formula I,

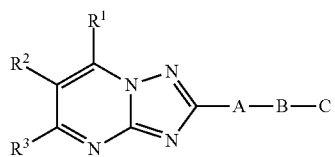

or pharmaceutically acceptable salts, solvates, and/or esters thereof, wherein:
A is O, $NR^4$, $C(R^5R^6)_n$, or bond;
B is a member selected from substituted or unsubstituted $C_2$-$C_8$ alkylene, substituted or unsubstituted $C_2$-$C_8$ alkyleneoxy, substituted or unsubstituted $C_2$-$C_8$ alkylenesulfanyl, substituted or unsubstituted $C_2$-$C_8$ alkylenesulfinyl, substituted or unsubstituted $C_2$-$C_8$ alkylenesulfonyl, and substituted or unsubstituted $C_2$-$C_8$ alkyleneamino;
C is a member selected from substituted or unsubstituted $C_3$-$C_{12}$ cycloalkyl, and substituted or unsubstituted $C_6$-$C_{12}$ aryl;
$R^1$ is a member selected from hydrogen, halo, substituted or unsubstituted alkyl, substituted or unsubstituted haloalkyl, substituted or unsubstituted alkoxy, substituted or unsubstituted cycloalkyl, and substituted or unsubstituted heterocycloalkyl;
$R^2$ is a member selected from hydrogen, halo, hydroxy, and substituted or unsubstituted alkyl;
$R^3$ is a member selected from hydrogen, halo, substituted or unsubstituted alkyl, substituted or unsubstituted haloalkyl, substituted or unsubstituted alkoxy, substituted or unsubstituted cycloalkyl, and substituted or unsubstituted heterocycloalkyl; and
Each $R^4$, $R^5$, and $R^6$ is independently selected from hydrogen, substituted or unsubstituted alkyl, substituted or unsubstituted haloalkyl, substituted or unsubstituted hydroxyalkyl, substituted or unsubstituted alkoxyalkyl, substituted or unsubstituted aminoalkyl, substituted or unsubstituted alkylaminoalkyl, and substituted or unsubstituted dialkylaminoalkyl; and
n is 0 to 3.

3. The compound according to claim 2, or pharmaceutically acceptable salts, solvates, and/or esters thereof, wherein:
A is O, NH, $N(CH_3)$, $N(CH_2CH_3)$, or $N(CH_2CH_2OH)$;
B is a member selected from substituted or unsubstituted $C_2$-$C_8$ alkylene, substituted or unsubstituted $C_2$-$C_8$ alkyleneoxy, substituted or unsubstituted $C_2$-$C_8$ alkylenesulfanyl, substituted or unsubstituted $C_2$-$C_8$ alkylenesulfinyl, substituted or unsubstituted $C_2$-$C_8$ alkylenesulfonyl, and substituted or unsubstituted $C_2$-$C_8$ alkyleneamino;
C is a member selected from substituted or unsubstituted $C_3$-$C_{12}$ cycloalkyl, and substituted or unsubstituted $C_6$-$C_{12}$ aryl;
$R^1$ is a member selected from hydrogen, halo, substituted or unsubstituted alkyl, substituted or unsubstituted haloalkyl, substituted or unsubstituted alkoxy, substituted or unsubstituted cycloalkyl, and substituted or unsubstituted heterocycloalkyl;
$R^2$ is a member selected from hydrogen, halo, hydroxy, and substituted or unsubstituted alkyl; and
$R^3$ is a member selected from hydrogen, halo, substituted or unsubstituted alkyl, substituted or unsubstituted haloalkyl, substituted or unsubstituted alkoxy, substituted or unsubstituted cycloalkyl, and substituted or unsubstituted heterocycloalkyl.

4. The compound according to claim 2, or pharmaceutically acceptable salts, solvates, and/or esters thereof, wherein:
A is bond;
B is a member selected from substituted or unsubstituted $C_3$-$C_8$ alkylene, substituted or unsubstituted $C_3$-$C_8$ alkyleneoxy, substituted or unsubstituted $C_3$-$C_8$ alkylenesulfanyl, substituted or unsubstituted $C_3$-$C_8$ alkylenesulfinyl, substituted or unsubstituted $C_3$-$C_8$ alkylenesulfonyl, and substituted or unsubstituted $C_3$-$C_8$ alkyleneamino;
C is a member selected from substituted or unsubstituted $C_3$-$C_{12}$ cycloalkyl, and substituted or unsubstituted $C_6$-$C_{12}$ aryl;
$R^1$ is a member selected from hydrogen, halo, substituted or unsubstituted alkyl, substituted or unsubstituted haloalkyl, substituted or unsubstituted alkoxy, substituted or unsubstituted cycloalkyl, and substituted or unsubstituted heterocycloalkyl;
$R^2$ is a member selected from hydrogen, halo, hydroxy, and substituted or unsubstituted alkyl; and
$R^3$ is a member selected from hydrogen, halo, substituted or unsubstituted alkyl, substituted or unsubstituted haloalkyl, substituted or unsubstituted alkoxy, substituted or unsubstituted cycloalkyl, and substituted or unsubstituted heterocycloalkyl.

5. The compound of claim 2, wherein:
A is O;
B is —$(CH_2)_2$—O—, —$(CH_2)_2$—S—, or —$(CH_2)_2$—N$(CH_2CH_2OH)$—;
C is unsubstituted phenyl, or phenyl substituted with alkyl, alkoxy, or halo;
$R^1$ and $R^3$ are each methyl, ethyl, or isopropyl; and
$R^2$ is hydrogen.

6. The compound of claim 2, wherein:
A is NH or $N(CH_3)$;
B is —$(CH_2)_2$—O—;
C is unsubstituted phenyl, or phenyl substituted with alkyl, alkoxy, or halo;
$R^1$ and $R^3$ are each methyl, ethyl, or isopropyl; and
$R^2$ is hydrogen.

7. The compound of claim 2, wherein:
A is bond;
B is —$(CH_2)_3$—O—, —$(CH_2)_4$—O—, —$(CH_2)_3$—N$(CH_2CH_2OH)$—, or —$(CH_2)_3$—N$(CH_2CH_2OC(O)CH_3)$—;
C is unsubstituted phenyl, or phenyl substituted with alkyl, alkoxy, or halo;
$R^1$ and $R^3$ are each methyl, ethyl, isopropyl, or —$CF_3$; and
$R^2$ is hydrogen.

8. A pharmaceutical composition comprising: at least one compound of claim 2 and at least one pharmaceutically acceptable excipient.

9. A method of treating a disorder, symptom, or disease by administering a pharmacological dose of a compound of claim 2 to an animal; and a method wherein the said animal is human; wherein the disorder, symptom, or disease is selected from a group consisting of anemia, Alzheimer's disease, Parkinson's disease, multiple sclerosis, Friedreich's ataxia, spinal muscular atrophy, Amyotrophic lateral sclerosis, Huntington's disease, spinal cord injury, traumatic brain injury, ischemic or hemorrhagic stroke, myocardial infarction, heart failure, peripheral nerve injury or blood vessel injury, kidney injury, liver injury, soft-tissue injury, skin injury, bone fracture, glaucoma, optic nerve injury, age-related macular degeneration, chronic diabetic macular edema, retinopathy, peripheral neuropathy, transplantation, alcohol addiction, substance abuse, bipolar disorder, schizophrenia, depression and diabetes.

10. The compound of claim 2 or pharmaceutically acceptable salts, solvates, and/or esters thereof, selected from the group consisting of:
2-[3-(4-chlorophenoxyl)propyl]-5,7-diethyl-[1,2,4]triazolo[1,5-a]pyrimidine;
2-[(3-{5,7-diethyl-[1,2,4]triazolo[1,5-a]pyrimidin-2-yl}propyl)(4-fluorophenyl)amino]ethan-1-ol;
2-[2-(4-chlorophenoxyl)ethoxy]-5,7-dimethyl-[1,2,4]triazolo[1,5-a]pyrimidine;
2-{[2-({5,7-dimethyl-[1,2,4]triazolo[1,5-a]pyrimidin-2-yl}oxy)ethyl]-(phenyl)amino}ethan-1-ol;
2-{[2-({5,7-diethyl-[1,2,4]triazolo[1,5-a]pyrimidin-2-yl}oxy)ethyl]-(4-fluorophenyl)amino}ethan-1-ol;
2-{[2-({5,7-diethyl-[1,2,4]triazolo[1,5-a]pyrimidin-2-yl}oxy)ethyl]-(phenyl)amino}ethan-1-ol;
5,7-diethyl-N-(2-phenoxyethyl)-[1,2,4]triazolo[1,5-a]pyrimidin-2-amine;
2-[3-(4-chloro-3-fluorophenoxy)propyl]-5,7-bis(propan-2-yl)-[1,2,4]triazolo[1,5-a]pyrimidine;
2-[3-(4-fluorophenoxyl)propyl]-5,7-bis(propan-2-yl)-[1,2,4]triazolo[1,5-a]pyrimidine;
2-[2-(4-chlorophenoxyl)ethoxy]-5,7-diethyl-[1,2,4]triazolo[1,5-a]pyrimidine;
2-[2-(4-fluorophenoxyl)ethoxy]-5,7-diethyl-[1,2,4]triazolo[1,5-a]pyrimidine;
2-{2-[(4-chlorophenyl)sulfanyl]ethoxy}-5,7-diethyl-[1,2,4]triazolo[1,5-a]pyrimidine; and
2-[3-(4-chlorophenoxyl)propyl]-5-methyl-7-(trifluoromethyl)-[1,2,4]triazolo[1,5-a]pyrimidine.

11. A compound of formula I

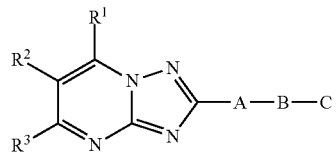

(I)

or pharmaceutically acceptable salts, solvates, and/or esters thereof,
wherein:
A is O, NR⁴, C(R⁵R⁶)$_n$, or bond;
B is a member selected from alkyleneoxy, alkylenesulfanyl, alkylenesulfinyl, alkylenesulfonyl, alkyleneamino, alkylene(2-hydroxyethyl)amino, alkylene(2-acetyloxyethyl)amino, and alkylenecarbonylamino;
C is a member selected from substituted or unsubstituted alkyl, substituted or unsubstituted cycloalkyl, and substituted or unsubstituted aryl;
R¹ is a member selected from hydrogen, halo, substituted or unsubstituted alkyl, substituted or unsubstituted haloalkyl, substituted or unsubstituted alkoxy, substituted or unsubstituted cycloalkyl, and substituted or unsubstituted heterocycloalkyl;
R² is a member selected from hydrogen, halo, hydroxy, and substituted or unsubstituted alkyl;
R³ is a member selected from hydrogen, halo, substituted or unsubstituted alkyl, substituted or unsubstituted haloalkyl, substituted or unsubstituted alkoxy, substituted or unsubstituted cycloalkyl, and substituted or unsubstituted heterocycloalkyl;
Each R⁴, R⁵, and R⁶ is independently selected from hydrogen, substituted or unsubstituted alkyl, substituted or unsubstituted haloalkyl, substituted or unsubstituted hydroxyalkyl, substituted or unsubstituted alkoxyalkyl, substituted or unsubstituted aminoalkyl, substituted or unsubstituted alkylaminoalkyl, and substituted or unsubstituted dialkylaminoalkyl; and
n is 0 to 3.

12. The compound of claim 11 in which:
A is O, NR⁴, or CH₂;
B is a member selected from alkyleneoxy, alkylenesulfanyl, alkylenesulfinyl, alkylenesulfonyl, alkyleneamino, alkylene(2-hydroxyethyl)amino, and alkylene(2-acetylcarboxyethyl)amino;
C is a member selected from substituted or unsubstituted alkyl, substituted or unsubstituted cycloalkyl, and substituted or unsubstituted aryl;
R¹ is a member selected from hydrogen, halo, substituted or unsubstituted alkyl, substituted or unsubstituted haloalkyl, and substituted or unsubstituted alkoxy;
R² is a member selected from hydrogen, halo, hydroxy, and substituted or unsubstituted alkyl;
R³ is a member selected from hydrogen, halo, substituted or unsubstituted alkyl, substituted or unsubstituted haloalkyl, and substituted or unsubstituted alkoxy; and
R⁴ is hydrogen or alkyl.

13. The compound of claim 12 in which R¹ is methyl, trifluoromethyl, ethyl or isopropyl, R² is hydrogen, R³ is methyl, trifluoromethyl, ethyl or isopropyl, A is O, NH, or CH₂, B is ethyleneoxy or ethylene(2-hydroxyethyl)amino, and C is phenyl optionally substituted with 1-3 groups selected from halo, methoxy, and isopropyl.

14. The compound of claim 13 selected from:
2-[2-(4-chlorophenoxyl)ethoxy]-5,7-dimethyl-[1,2,4]triazolo[1,5-a]pyrimidine;
2-{[2-({5,7-dimethyl-[1,2,4]triazolo[1,5-a]pyrimidin-2-yl}oxy)ethyl](phenyl)amino}ethan-1-ol;
2-{[2-({5,7-diethyl-[1,2,4]triazolo[1,5-a]pyrimidin-2-yl}oxy)ethyl](4-fluorophenyl)amino}ethan-1-ol;
5,7-diethyl-2-[2-(4-fluorophenoxyl)ethoxy]-[1,2,4]triazolo[1,5-a]pyrimidine;
5,7-diethyl-2-[2-(4-chlorophenoxyl)ethoxy]-[1,2,4]triazolo[1,5-a]pyrimidine;
2-{[2-({5,7-diethyl-[1,2,4]triazolo[1,5-a]pyrimidin-2-yl}oxy)ethyl](phenyl)amino}ethan-1-ol;
5,7-diethyl-N-(2-phenoxyethyl)-[1,2,4]triazolo[1,5-a]pyrimidin-2-amine;
2-[(3-{5,7-diethyl-[1,2,4]triazolo[1,5-a]pyrimidin-2-yl}propyl)(4-fluorophenyl)amino]ethan-1-ol;
2-[3-(4-chlorophenoxyl)propyl]-5,7-diethyl-[1,2,4]triazolo[1,5-a]pyrimidine; and
2-[3-(4-fluorophenoxyl)propyl]-5,7-bis(propan-2-yl)-[1,2,4]triazolo[1,5-a]pyrimidine;
and/or pharmaceutically acceptable salts, solvates, and/or esters thereof.

15. The compound of claim 14 selected from:
2-[2-(4-chlorophenoxyl)ethoxy]-5,7-dimethyl-[1,2,4]triazolo[1,5-a]pyrimidine;
2-{[2-({5,7-dimethyl-[1,2,4]triazolo[1,5-a]pyrimidin-2-yl}oxy)ethyl](phenyl)amino}ethan-1-ol; and
5,7-diethyl-N-(2-phenoxyethyl)-[1,2,4]triazolo[1,5-a]pyrimidin-2-amine;
and/or pharmaceutically acceptable salts, solvates, and/or esters thereof.

16. A pharmaceutical composition comprising at least one compound of claim 11 and at least one pharmaceutically acceptable excipient.

17. A method of treating a disorder, symptom, or disease by administering a pharmacological dose of at least one compound of claim 11 to an animal; and the method wherein said animal is human; wherein the disorder, symptom, or disease is selected from a group consisting of anemia, Alzheimer's disease, Parkinson's disease, multiple sclerosis, Friedreich's ataxia, spinal muscular atrophy, Amyotrophic lateral sclerosis, Huntington's disease, spinal cord injury, traumatic brain injury, ischemic or hemorrhagic stroke, myocardial infarction, heart failure, peripheral nerve injury or blood vessel injury, kidney injury, liver injury, soft-tissue injury, skin injury, bone fracture, glaucoma, optic nerve injury, age-related macular degeneration, chronic diabetic macular edema, retinopathy, peripheral neuropathy, transplantation alcohol addiction substance abuse bipolar disorder schizophrenia, depression and diabetes.

18. A method of treating a disorder, symptom, or disease by administering a pharmacological dose of at least one compound of claim 14, wherein the disorder, symptom, or disease is selected from a group consisting of anemia, Alzheimer's disease, Parkinson's disease, multiple sclerosis, Friedreich's ataxia, spinal muscular atrophy, Amyotrophic lateral sclerosis, Huntington's disease, spinal cord injury, traumatic brain injury, ischemic or hemorrhagic stroke, myocardial infarction, heart failure, peripheral nerve injury or blood vessel injury, kidney injury, liver injury, soft-tissue injury, skin injury, bone fracture, glaucoma, optic nerve injury, age-related macular degeneration, chronic diabetic macular edema, retinopathy, peripheral neuropathy, transplantation, alcohol addiction, substance abuse, bipolar disorder, schizophrenia, depression and diabetes.

19. A compound of formula I

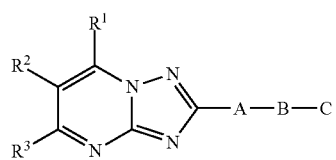

or pharmaceutically acceptable salts, solvates, and/or esters thereof,
wherein:
A is a member selected from O, $NR^4$, $C(R^5R^6)_n$, or bond;
B is a member selected from $C_2$-$C_4$ alkyleneoxy, $C_2$-$C_4$ alkylenesulfanyl, and $C_2$-$C_4$ alkyleneamino;
C is substituted or unsubstituted $C_6$-$C_{12}$ aryl;
$R^1$ is a member selected from hydrogen or unsubstituted or substituted alkyl;
$R^2$ is hydrogen or unsubstituted or substituted alkyl;
$R^3$ is a member selected from hydrogen or unsubstituted or substituted alkyl;
Each $R^4$, $R^5$, and $R^6$ is independently selected from hydrogen or unsubstituted or substituted alkyl; and
n is 0 to 3.

20. The compound according to claim 19, wherein A is a member selected from O, NH, and $CH_2$.

21. The compound according to claim 19 wherein B is a member selected from alkyleneoxy, alkylenesulfanyl, alkyleneamino, alkylene(2-hydroxyethyl)amino, and alkylene(2-acetyloxyethyl)amino.

22. The compound according to claim 19 wherein B is a member selected from unsubstituted ethyleneoxy, unsubstituted propyleneoxy, unsubstituted ethyleneamino, ethylene (2-hydroxyethyl)amino, and unsubstituted ethylenesulfanyl.

23. The compound according to claim 19 wherein A is a member selected from 0, $NH_2$, and $CH_2$; and B is a member selected from —(CH2)$_2$-O—, —(CH$_2$)$_2$—NH—, and —(CH$_2$)$_2$—N(CH$_2$CH$_2$OH)—.

24. The compound according to claim 19 wherein: A is O; B is —(CH$_2$)$_2$—O—, —(CH$_2$)$_2$—S—, or —(CH$_2$)$_2$—N(CH$_2$CH$_2$OH)—; C is unsubstituted phenyl, or phenyl substituted with alkyl, alkoxy, or halo; $R^1$ and $R^3$ are each methyl, ethyl, or isopropyl; and $R^2$ is hydrogen.

25. The compound according to claim 19 wherein: A is O; B is —(CH$_2$)$_2$—O—; C is phenyl substituted with chloro or fluoro; $R^1$ and $R^3$ are each methyl; and $R^2$ is hydrogen.

26. The compound according to claim 19 wherein: A is NH or N(CH$_3$); B is —(CH$_2$)$_2$—O—; C is unsubstituted phenyl, or phenyl substituted with alkyl, alkoxy, or halo; $R^1$ and $R^3$ are each methyl, ethyl, or isopropyl; and $R^2$ is hydrogen.

27. The compound according to claim 19 wherein: A is bond; B is —(CH$_2$)$_3$—O—, —(CH$_2$)$_4$—O—, —(CH$_2$)$_3$—N(CH$_2$CH$_2$OH)—, or —(CH$_2$)$_3$—N(CH$_2$CH$_2$OC(O)CH$_3$)—; C is unsubstituted phenyl, or phenyl substituted with alkyl, alkoxy, or halo; $R^1$ and $R^3$ are each methyl, ethyl, isopropyl, or —CF$_3$; and $R^2$ is hydrogen.

28. The compound according to claim 19 wherein: each $R^1$ and $R^3$ is independently selected from hydrogen, methyl, ethyl, —CH(CH$_3$)$_2$, —CF$_3$, and —CHF$_2$.

29. The compound according to claim 19 wherein: each $R^1$ and $R^3$ is independently selected from hydrogen, methyl, ethyl, and —CH(CH$_3$)$_2$; $R^2$ is hydrogen; and C is substituted or unsubstituted phenyl.

30. The compound according to claim 19 wherein C is substituted phenyl.

31. The compound according to claim 19 wherein: C is phenyl substituted with one to three members selected from —F, —Cl, —Br, —I, methyl, ethyl, isopropyl, tert-butyl, methoxy, —(CH$_2$)$_2$—OH, or —(CH$_2$)$_2$—N(CH$_3$)$_2$.

32. The compound according to claim 19 wherein C is a member selected from:

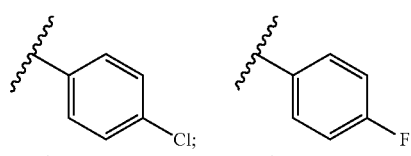

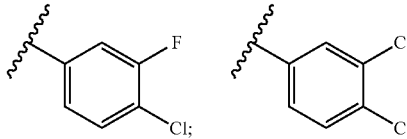

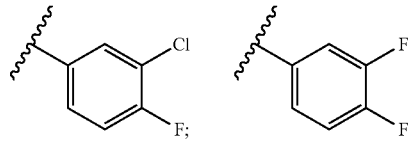

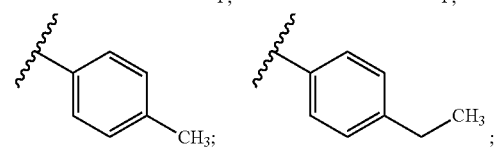

-continued

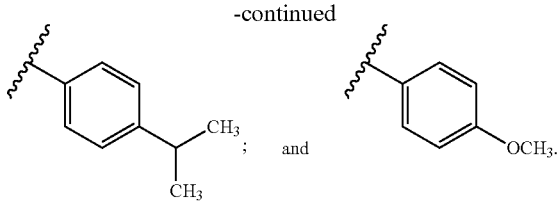

33. The compound according to claim 19 in which A is O or NH; B is ethyleneoxy, ethyleneamino, ethylene(2-hydroxyethyl)amino, or ethylenesulfanyl; C is phenyl substituted with 1-3 groups selected from halo, methoxy, and isopropyl; $R^1$ is methyl, difluoromethyl, trifluoromethyl, ethyl or isopropyl; $R^2$ is hydrogen; and $R^3$ is methyl, difluoromethyl, trifluoromethyl, ethyl or isopropyl.

34. The compound, or pharmaceutically acceptable salts and/or solvates, thereof, named:
   2-{[2-(4-chlorophenoxyl)ethyl]sulfanyl}-5,7-dimethyl-[1,2,4]triazolo[1,5-a]pyrimidine;
   2-{[2-(4-chlorophenoxyl)ethyl]sulfanyl}-5-methyl-[1,2,4]triazolo[1,5-a]pyrimidine;
   2-{[2-(4-chlorophenoxyl)ethyl]sulfanyl}-7-methyl-[1,2,4]triazolo[1,5-a]pyrimidine;
   2-{[2-(4-chloro-3-fluorophenoxy)ethyl]sulfanyl}-5,7-dimethyl-[1,2,4]triazolo[1,5-a]pyrimidine;
   2-{[2-(4-fluorophenoxyl)ethyl]sulfanyl}-5,7-dimethyl-[1,2,4]triazolo[1,5-a]pyrimidine;
   2-{[2-(3,4-dichlorophenoxyl)ethyl]sulfanyl}-5,7-dimethyl-[1,2,4]triazolo[1,5-a]pyrimidine;
   2-{[2-(3-chloro-4-fluorophenoxy)ethyl]sulfanyl}-5,7-dimethyl-[1,2,4]triazolo[1,5-a]pyrimidine;
   2-{[2-(3,4-difluorophenoxyl)ethyl]sulfanyl}-5,7-dimethyl-[1,2,4]triazolo[1,5-a]pyrimidine;
   2-{[2-(4-ethylphenoxyl)ethyl]sulfanyl}-5,7-dimethyl-[1,2,4]triazolo[1,5-a]pyrimidine;
   2-{[2-(4-chlorophenoxyl)ethyl]sulfanyl}-5-methyl-7-(trifluoromethyl)-[1,2,4]triazolo[1 a]pyrimidine;
   2-{[2-(4-chlorophenoxyl)ethyl]sulfanyl}-5,7-bis(trifluoromethyl)-[1,2,4]triazolo[1,5-a]pyrimidine;
   2-{[2-{5,7-dimethyl-[1,2,4]triazolo[1,5-a]pyrimidin-2-yl}sulfanyl)ethyl]-(phenyl)amino}ethan-1-ol;
   (2-{4-[2-({5,7-dimethyl-[1,2,4]triazolo[1,5-a]pyrimidin-2-yl}sulfanyl)ethoxy]phenyl}ethyl)-dimethylamine;
   4-[2-({5,7-dimethyl-[1,2,4]triazolo[1,5-a]pyrimidin-2-yl}sulfanyl)ethoxy]pyridine;
   2-{[2-(cyclohexyloxy)ethyl]sulfanyl}-5,7-dimethyl-[1,2,4]triazolo pyrimidine;
   3-[2-({5,7-dimethyl-[1,2,4]triazolo[1,5-a]pyrimidin-2-yl}sulfanyl)ethyl]-1H-indole; and/or pharmaceutically acceptable salts, solvates, and/or esters thereof.

35. The compound of claim 19 selected from:
   2-[2-(4-chlorophenoxyl)ethoxy]-5,7-dimethyl-[1,2,4]triazolo[1,5-a]pyrimidine;
   2-{[2-({5,7-dimethyl-[1,2,4]triazolo[1,5-a]pyrimidin-2-yl}oxy)ethyl](phenyl)amino}ethan-1-ol;
   2-{[2-({5,7-diethyl-[1,2,4]triazolo[1,5-a]pyrimidin-2-yl}oxy)ethyl](4-fluorophenyl)amino}ethan-1-ol;
   5,7-diethyl-2-[2-(4-fluorophenoxyl)ethoxy]-[1,2,4]triazolo[1,5-a]pyrimidine;
   5,7-diethyl-2-[2-(4-chlorophenoxyl)ethoxy]-[1,2,4]triazolo[1,5-a]pyrimidine;
   2-{[2-({5,7-diethyl-[1,2,4]triazolo[1,5-a]pyrimidin-2-yl}oxy)ethyl](phenyl)amino}ethan-1-ol;
   5,7-diethyl-N-(2-phenoxyethyl)-[1,2,4]triazolo[1,5-a]pyrimidin-2-amine;
   N-[2-(4-chlorophenoxyl)ethyl]-5,7-dimethyl-[1,2,4]triazolo[1,5-a]pyrimidin-2-amine;
   2-[(3-{5,7-diethyl-[1,2,4]triazolo[1,5-a]pyrimidin-2-yl}propyl)(4-fluorophenyl)amino]ethan-1-ol;
   2-[(3-{5,7-diethyl-[1,2,4]triazolo[1,5-a]pyrimidin-2-yl}propyl)(4-fluorophenyl)amino]ethyl acetate
   2-[3-(4-chlorophenoxyl)propyl]-5-methyl-7-(trifluoromethyl)-[1,2,4]triazolo[1,5-a]pyrimidine;
   2-[3-(4-chlorophenoxyl)propyl]-5,7-diethyl-[1,2,4]triazolo[1,5-a]pyrimidine;
   2-[3-(4-fluorophenoxyl)propyl]-5,7-bis(propan-2-yl)-[1,2,4]triazolo[1,5-a]pyrimidine;
   5,7-bis(difluoromethyl)-2-[3-(4-fluorophenoxyl)propyl]-[1,2,4]triazolo[1,5-a]pyrimidine;
   2-{2-[(4-chlorophenyl)sulfanyl]ethoxy}-5,7-dimethyl-[1,2,4]triazolo[1,5-a]pyrimidine;
   and/or pharmaceutically acceptable salts, solvates, and/or esters thereof.

36. The compound of claim 35 selected from:
   2-[2-(4-chlorophenoxyl)ethoxy]-5,7-dimethyl-[1,2,4]triazolo[1,5-a]pyrimidine;
   2-{[2-({5,7-dimethyl-[1,2,4]triazolo[1,5-a]pyrimidin-2-yl}oxy)ethyl](phenyl)amino}ethan-1-ol;
   5,7-diethyl-N-(2-phenoxyethyl)-[1,2,4]triazolo[1,5-a]pyrimidin-2-amine;
   and/or pharmaceutically acceptable salts, solvates, and/or esters thereof.

37. A pharmaceutical composition comprising at least one compound of claim 19 and at least one pharmaceutically acceptable excipient.

38. An oral composition comprising at least one compound of claim 19 having an active drug component being combined with an oral pharmaceutically acceptable inert carrier.

39. A method of treating a disorder, symptom, or disease by administering a pharmacological dose of at least one compound of claim 19 to an animal; and the method wherein said animal is human; wherein the disorder, symptom, or disease is selected from a group consisting of anemia, Alzheimer's disease, Parkinson's disease, multiple sclerosis, Friedreich's ataxia, spinal muscular atrophy, Amyotrophic lateral sclerosis, Huntington's disease, spinal cord injury, traumatic brain injury, ischemic or hemorrhagic stroke, myocardial infarction, heart failure, peripheral nerve injury or blood vessel injury, kidney injury, liver injury, soft-tissue injury, skin injury, bone fracture, glaucoma, optic nerve injury, age-related macular degeneration, chronic diabetic macular edema, retinopathy, peripheral neuropathy, transplantation, alcohol addiction, substance abuse, bipolar disorder, schizophrenia, depression and diabetes.

40. The compound, or pharmaceutically acceptable salts and/or solvates, thereof, named:
   2-[2-(4-chlorophenoxyl)ethoxy]-5,7-dimethyl-[1,2,4]triazolo[1,5-a]pyrimidine;
   2-{[2({5,7-dimethyl-[1,2,4]triazolo[1,5-a]pyrimidin-2-yl}oxy)ethyl](phenyl)amino}ethan-1-ol; and
   5,7-diethyl-N-(2-phenoxyethyl)-[1,2,4]triazolo[1,5-a]pyrimidin-2-amine.

41. A pharmaceutical composition comprising at least one compound of claim 40 and at least one pharmaceutically acceptable excipient.

42. An oral composition comprising at least one compound of claim 40 having an active drug component being combined with an oral pharmaceutically acceptable inert carrier.

43. A method of treating a disorder, symptom, or disease by administering a pharmacological dose of at least one compound of claim 40 to an animal; and the method wherein said animal is human; wherein the disorder, symptom, or disease is selected from a group consisting of anemia, Alzheimer's disease, Parkinson's disease, multiple sclerosis, Friedreich's ataxia, spinal muscular atrophy, Amyotrophic lateral sclerosis, Huntington's disease, spinal cord injury, traumatic brain injury, ischemic or hemorrhagic stroke, myocardial infarction, heart failure, peripheral nerve injury or blood vessel injury, kidney injury, liver injury, soft-tissue injury, skin injury, bone fracture, glaucoma, optic nerve injury, age-related macular degeneration, chronic diabetic macular edema, retinopathy, peripheral neuropathy, transplantation, alcohol addiction, substance abuse, bipolar disorder, schizophrenia, depression and diabetes.

* * * * *